(12) United States Patent
Kavazov

(10) Patent No.: US 8,597,270 B2
(45) Date of Patent: *Dec. 3, 2013

(54) AUTOMATED FILLING SYSTEMS AND METHODS

(75) Inventor: Julian D. Kavazov, Arcadia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 13/163,548

(22) Filed: Jun. 17, 2011

(65) Prior Publication Data

US 2011/0247719 A1    Oct. 13, 2011

Related U.S. Application Data

(62) Division of application No. 12/107,580, filed on Apr. 22, 2008, now Pat. No. 7,963,954.

(60) Provisional application No. 60/927,032, filed on Apr. 30, 2007.

(51) Int. Cl.
```
A61B 19/00    (2006.01)
B65B 1/04     (2006.01)
B65B 3/04     (2006.01)
B67C 3/00     (2006.01)
B65B 3/00     (2006.01)
```

(52) U.S. Cl.
USPC ........... 604/403; 604/407; 141/329; 141/330; 141/346

(58) Field of Classification Search
USPC .......................................... 604/403, 411–415
See application file for complete search history.

(56) References Cited

U.S. PATENT DOCUMENTS

| | | |
|---|---|---|
| 1,948,982 A | 2/1934 | Cutter |
| 2,064,815 A | 12/1936 | Armstrong |
| 2,570,625 A | 10/1951 | Zimmerman et al. |

(Continued)

FOREIGN PATENT DOCUMENTS

| | | |
|---|---|---|
| DE | 10 2004 055 870 A1 | 5/2006 |
| DE | 20 2007 006 363 U1 | 8/2007 |
| EP | 1 462 134 A1 | 9/2004 |
| EP | 1 527 792 A1 | 5/2005 |

(Continued)

OTHER PUBLICATIONS

U.S. Notice of Allowance from related U.S. Appl. No. 12/111,751, mailed Mar. 4, 2013.

(Continued)

*Primary Examiner* — Susan Su
(74) *Attorney, Agent, or Firm* — Foley & Lardner LLP

(57) ABSTRACT

Various embodiments of the present invention are directed to transferring fluidic media from a vial to a reservoir. In various embodiments, fluidic media may be transferred from the vial to the reservoir by moving a housing portion to move a plunger head located in the reservoir to draw fluidic media from the vial to the reservoir. In other embodiments, fluidic media may be transferred from the vial to the reservoir while the reservoir is held by a holding unit and vibrated by a vibrator to remove air from the fluidic media. In some embodiments, fluidic media may be transferred from the vial to the reservoir by moving a handle operatively connected to a bias member for assisting with the transfer of fluidic media. In other embodiments, the transfer of fluidic media may be assisted by a bias member and a needle connecting atmosphere and the vial.

22 Claims, 26 Drawing Sheets

(56) References Cited

U.S. PATENT DOCUMENTS

| | | | |
|---|---|---|---|
| 2,627,857 A * | 2/1953 | Marcelli | 604/407 |
| 2,644,450 A | 7/1953 | Krewson | |
| RE24,918 E | 1/1961 | Mills | |
| 2,973,758 A | 3/1961 | Murrish | |
| 3,223,289 A | 12/1965 | Bouet | |
| 3,342,180 A | 9/1967 | Ellsworth et al. | |
| 3,343,422 A | 9/1967 | McSmith | |
| 3,572,552 A | 3/1971 | Guinn | |
| 3,623,474 A | 11/1971 | Heilman et al. | |
| 3,650,093 A | 3/1972 | Rosenberg | |
| 3,662,753 A | 5/1972 | Tassell | |
| 3,729,032 A | 4/1973 | Tischlinger et al. | |
| 3,802,430 A | 4/1974 | Schwebel et al. | |
| 3,963,151 A | 6/1976 | North, Jr. | |
| 3,993,061 A | 11/1976 | O'Leary | |
| 4,064,879 A | 12/1977 | Leibinsohn | |
| 4,089,624 A | 5/1978 | Nichols et al. | |
| 4,117,841 A | 10/1978 | Perrotta et al. | |
| 4,215,701 A | 8/1980 | Raitto | |
| 4,219,055 A | 8/1980 | Wright | |
| 4,234,108 A | 11/1980 | Diamond | |
| 4,373,535 A | 2/1983 | Martell | |
| 4,392,850 A | 7/1983 | Elias et al. | |
| 4,434,820 A | 3/1984 | Glass | |
| 4,448,206 A | 5/1984 | Martell | |
| 4,493,704 A | 1/1985 | Beard et al. | |
| 4,568,336 A | 2/1986 | Cooper | |
| 4,572,210 A | 2/1986 | McKinnon | |
| 4,585,435 A | 4/1986 | Vaillancourt | |
| 4,684,365 A | 8/1987 | Reinicke | |
| 4,684,366 A | 8/1987 | Denny et al. | |
| 4,703,763 A | 11/1987 | McAlister et al. | |
| 4,743,249 A | 5/1988 | Loveland | |
| 4,744,955 A | 5/1988 | Shapiro | |
| 4,759,756 A | 7/1988 | Forman et al. | |
| 4,838,857 A | 6/1989 | Strowe et al. | |
| 4,865,592 A | 9/1989 | Rycroft | |
| 4,883,101 A | 11/1989 | Strong | |
| 4,913,703 A | 4/1990 | Pasqualucci et al. | |
| 4,957,637 A | 9/1990 | Cornell | |
| 4,976,696 A | 12/1990 | Sanderson et al. | |
| 4,986,820 A | 1/1991 | Fischer | |
| 4,994,034 A | 2/1991 | Botich et al. | |
| 5,002,527 A | 3/1991 | Reller et al. | |
| 5,045,096 A | 9/1991 | Quang et al. | |
| 5,049,129 A | 9/1991 | Zdeb et al. | |
| 5,053,001 A | 10/1991 | Reller et al. | |
| 5,062,834 A | 11/1991 | Gross et al. | |
| 5,090,963 A | 2/1992 | Gross et al. | |
| 5,115,948 A | 5/1992 | Johnson | |
| 5,156,591 A | 10/1992 | Gross et al. | |
| 5,176,502 A | 1/1993 | Sanderson et al. | |
| 5,186,805 A | 2/1993 | Gross et al. | |
| 5,190,522 A | 3/1993 | Wojcicki et al. | |
| 5,203,506 A | 4/1993 | Gross et al. | |
| 5,232,449 A | 8/1993 | Stern et al. | |
| 5,242,406 A | 9/1993 | Gross et al. | |
| 5,242,408 A | 9/1993 | Jhuboo et al. | |
| 5,246,147 A | 9/1993 | Gross | |
| 5,254,096 A | 10/1993 | Rondelet et al. | |
| 5,259,732 A | 11/1993 | Stern | |
| 5,261,884 A | 11/1993 | Stern et al. | |
| 5,275,582 A | 1/1994 | Wimmer | |
| 5,284,570 A | 2/1994 | Savage et al. | |
| 5,292,318 A | 3/1994 | Haber et al. | |
| 5,295,966 A | 3/1994 | Stern et al. | |
| 5,295,967 A | 3/1994 | Rondelet et al. | |
| 5,308,333 A | 5/1994 | Skakoon | |
| 5,312,364 A | 5/1994 | Jacobs | |
| 5,356,632 A | 10/1994 | Gross et al. | |
| 5,367,891 A | 11/1994 | Furuyama | |
| 5,385,559 A | 1/1995 | Mannix | |
| 5,387,450 A | 2/1995 | Stewart | |
| 5,407,434 A | 4/1995 | Gross | |
| 5,409,236 A | 4/1995 | Therrien | |
| 5,425,706 A | 6/1995 | Gross et al. | |
| 5,496,285 A | 3/1996 | Schumacher et al. | |
| 5,527,288 A | 6/1996 | Gross et al. | |
| 5,533,964 A | 7/1996 | Halperin et al. | |
| 5,697,916 A | 12/1997 | Schraga | |
| 5,704,520 A | 1/1998 | Gross | |
| 5,800,420 A | 9/1998 | Gross et al. | |
| 5,807,375 A | 9/1998 | Gross et al. | |
| 5,820,622 A | 10/1998 | Gross et al. | |
| 5,848,991 A | 12/1998 | Gross et al. | |
| 5,851,549 A | 12/1998 | Svec | |
| 5,858,001 A | 1/1999 | Tsals et al. | |
| 5,865,803 A | 2/1999 | Major | |
| 5,871,125 A | 2/1999 | Gross | |
| 5,887,752 A | 3/1999 | Strother | |
| 5,933,287 A | 8/1999 | Muller | |
| 5,951,523 A | 9/1999 | Osterlind et al. | |
| 5,954,697 A | 9/1999 | Srisathapat et al. | |
| 5,957,889 A | 9/1999 | Poulsen et al. | |
| 5,984,894 A | 11/1999 | Poulsen et al. | |
| 5,997,501 A | 12/1999 | Gross et al. | |
| 6,003,736 A | 12/1999 | Ljunggren | |
| 6,033,377 A | 3/2000 | Rasmussen et al. | |
| 6,067,906 A | 5/2000 | Ryan et al. | |
| 6,088,608 A | 7/2000 | Schulman et al. | |
| 6,099,504 A | 8/2000 | Gross et al. | |
| 6,117,107 A | 9/2000 | Chen | |
| 6,119,028 A | 9/2000 | Schulman et al. | |
| 6,126,643 A | 10/2000 | Vaillancouert | |
| 6,186,982 B1 | 2/2001 | Gross et al. | |
| 6,229,584 B1 | 5/2001 | Chuo et al. | |
| 6,242,665 B1 | 6/2001 | Malowaniec | |
| 6,248,093 B1 | 6/2001 | Moberg | |
| 6,261,272 B1 | 7/2001 | Gross et al. | |
| 6,275,717 B1 | 8/2001 | Gross et al. | |
| 6,277,095 B1 | 8/2001 | Kriesel et al. | |
| 6,312,409 B1 | 11/2001 | Gross | |
| 6,314,317 B1 | 11/2001 | Willis | |
| 6,346,095 B1 | 2/2002 | Gross et al. | |
| 6,364,865 B1 | 4/2002 | Lavi et al. | |
| 6,375,047 B1 | 4/2002 | Herda et al. | |
| 6,406,455 B1 | 6/2002 | Willis et al. | |
| 6,423,035 B1 | 7/2002 | Das et al. | |
| 6,440,096 B1 | 8/2002 | Lastovich et al. | |
| 6,450,993 B1 | 9/2002 | Lin | |
| 6,461,329 B1 | 10/2002 | Van Antwerp et al. | |
| 6,474,219 B2 | 11/2002 | Klitmose et al. | |
| 6,474,375 B2 | 11/2002 | Spero et al. | |
| 6,478,771 B1 | 11/2002 | Lavi et al. | |
| 6,485,461 B1 | 11/2002 | Mason et al. | |
| 6,485,465 B2 | 11/2002 | Moberg et al. | |
| 6,490,483 B2 | 12/2002 | Willis | |
| 6,503,225 B1 | 1/2003 | Kirsch et al. | |
| 6,508,788 B2 | 1/2003 | Preuthun | |
| 6,537,251 B2 | 3/2003 | Klitmose | |
| 6,551,285 B1 | 4/2003 | Bierman | |
| 6,572,600 B1 | 6/2003 | Roe et al. | |
| 6,585,707 B2 | 7/2003 | Cabiri et al. | |
| 6,589,229 B1 | 7/2003 | Connelly et al. | |
| 6,595,956 B1 | 7/2003 | Gross et al. | |
| 6,607,509 B2 | 8/2003 | Bobroff et al. | |
| 6,607,513 B1 | 8/2003 | Down et al. | |
| 6,613,019 B2 | 9/2003 | Munk | |
| 6,616,627 B2 | 9/2003 | Willis et al. | |
| 6,626,874 B1 | 9/2003 | Duchamp | |
| 6,641,565 B1 | 11/2003 | Lavi et al. | |
| 6,641,566 B2 | 11/2003 | Douglas et al. | |
| 6,645,181 B1 | 11/2003 | Lavi et al. | |
| 6,656,147 B1 | 12/2003 | Gertsek et al. | |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,689,100 B2 | 2/2004 | Connelly et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,195 B2 | 4/2004 | Nolan et al. | |
| 6,719,734 B1 | 4/2004 | Harkless | |

(56) References Cited

U.S. PATENT DOCUMENTS

| | | |
|---|---|---|
| 6,723,068 B2 | 4/2004 | Lavi et al. |
| 6,723,072 B2 | 4/2004 | Flaherty et al. |
| 6,740,059 B2 | 5/2004 | Flaherty |
| 6,740,072 B2 | 5/2004 | Starkweather et al. |
| 6,749,587 B2 | 6/2004 | Flaherty |
| 6,767,188 B2 | 7/2004 | Vrane et al. |
| 6,768,425 B2 | 7/2004 | Flaherty et al. |
| 6,786,246 B2 | 9/2004 | Ohms et al. |
| 6,796,965 B2 | 9/2004 | Dumaresq-Lucas et al. |
| 6,808,506 B2 | 10/2004 | Lastovich et al. |
| 6,827,702 B2 | 12/2004 | Lebel et al. |
| 6,830,558 B2 | 12/2004 | Flaherty et al. |
| 6,830,560 B1 | 12/2004 | Gross et al. |
| 6,886,724 B2 | 5/2005 | Hung |
| 6,899,699 B2 | 5/2005 | Enggaard |
| 6,915,147 B2 | 7/2005 | Lebel et al. |
| 6,918,887 B1 | 7/2005 | Gremel et al. |
| 6,936,006 B2 | 8/2005 | Sabra |
| 6,939,324 B2 | 9/2005 | Gonnelli et al. |
| 6,948,522 B2 | 9/2005 | Newbrough et al. |
| 6,948,918 B2 | 9/2005 | Hansen |
| 6,952,604 B2 | 10/2005 | Denuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 7,220,245 B2 | 5/2007 | Kriesel |
| 7,220,889 B2 | 5/2007 | Sigurjonsson et al. |
| 7,318,816 B2 | 1/2008 | Bobroff et al. |
| 7,323,142 B2 | 1/2008 | Pendo et al. |
| 7,390,294 B2 | 6/2008 | Hassler, Jr. |
| 7,399,484 B2 | 7/2008 | Ellefson et al. |
| 7,621,429 B2 | 11/2009 | Wu et al. |
| 7,686,787 B2 | 3/2010 | Moberg et al. |
| 7,858,112 B2 | 12/2010 | Hatanaka et al. |
| 7,981,085 B2 | 7/2011 | Ethelfeld |
| 8,409,143 B2 | 4/2013 | Lanigan et al. |
| 2001/0041869 A1 | 11/2001 | Causey et al. |
| 2002/0040208 A1 | 4/2002 | Flaherty et al. |
| 2002/0072733 A1 | 6/2002 | Flaherty |
| 2002/0104584 A1 | 8/2002 | Spero et al. |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2003/0023206 A1 | 1/2003 | Bausmith et al. |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0104032 A1 | 6/2003 | Sawhney et al. |
| 2003/0125672 A1 | 7/2003 | Adair et al. |
| 2003/0167035 A1 | 9/2003 | Flaherty et al. |
| 2003/0167036 A1 | 9/2003 | Flaherty |
| 2003/0199824 A1 | 10/2003 | Mahoney et al. |
| 2003/0199825 A1 | 10/2003 | Flaherty |
| 2003/0212364 A1 | 11/2003 | Mann et al. |
| 2003/0229310 A1 | 12/2003 | Flaherty et al. |
| 2003/0233069 A1 | 12/2003 | Gillespie et al. |
| 2004/0002682 A1 | 1/2004 | Kovelman et al. |
| 2004/0010207 A1 | 1/2004 | Flaherty et al. |
| 2004/0011866 A1 | 1/2004 | Saad |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0073095 A1 | 4/2004 | Causey et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0140327 A1 | 7/2004 | Osborne et al. |
| 2004/0158207 A1 | 8/2004 | Hunn et al. |
| 2004/0199140 A1 | 10/2004 | Rue et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0236201 A1 | 11/2004 | Lebel et al. |
| 2004/0260233 A1 | 12/2004 | Garibotto et al. |
| 2005/0022274 A1 | 1/2005 | Campbell et al. |
| 2005/0065760 A1 | 3/2005 | Murtfeldt et al. |
| 2005/0101920 A1 | 5/2005 | Keane et al. |
| 2005/0119618 A1 | 6/2005 | Gonnelli |
| 2005/0137530 A1 | 6/2005 | Campbell et al. |
| 2006/0184119 A1 | 8/2006 | Remde et al. |
| 2006/0253085 A1 | 11/2006 | Geismar et al. |
| 2006/0264835 A1 | 11/2006 | Nielsen et al. |
| 2006/0264894 A1 | 11/2006 | Moberg et al. |
| 2007/0062068 A1 | 3/2007 | Li |
| 2007/0066939 A1 | 3/2007 | Krulevitch et al. |
| 2007/0073235 A1 | 3/2007 | Estes et al. |
| 2007/0293826 A1 | 12/2007 | Wall et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051710 A1 | 2/2008 | Moberg et al. |
| 2008/0051711 A1 | 2/2008 | Mounce et al. |
| 2008/0051714 A1 | 2/2008 | Moberg et al. |
| 2008/0051716 A1 | 2/2008 | Stutz |
| 2008/0051718 A1 | 2/2008 | Kavazov et al. |
| 2008/0051727 A1 | 2/2008 | Moberg et al. |
| 2008/0051730 A1 | 2/2008 | Bikovsky |
| 2008/0051738 A1 | 2/2008 | Griffin |
| 2008/0051765 A1 | 2/2008 | Mounce |
| 2008/0077081 A1 | 3/2008 | Mounce et al. |
| 2008/0097291 A1 | 4/2008 | Hanson et al. |
| 2008/0097321 A1 | 4/2008 | Mounce et al. |
| 2008/0097326 A1 | 4/2008 | Moberg et al. |
| 2008/0097327 A1 | 4/2008 | Bente et al. |
| 2008/0097328 A1 | 4/2008 | Moberg et al. |
| 2008/0097375 A1 | 4/2008 | Bikovsky |
| 2008/0097381 A1 | 4/2008 | Moberg et al. |
| 2008/0257916 A1 | 10/2008 | Chang |
| 2008/0269682 A1 | 10/2008 | Kavazov et al. |
| 2009/0206111 A1 | 8/2009 | Conrardy et al. |

FOREIGN PATENT DOCUMENTS

| | | |
|---|---|---|
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 1 646 412 | 3/2007 |
| EP | 1 095 668 | 4/2007 |
| FR | 1496026 | 9/1967 |
| GB | 1 452 104 | 10/1976 |
| GB | 2 176 711 A0 | 1/1987 |
| GB | 2 207 652 A0 | 2/1989 |
| WO | WO-95/32015 | 11/1995 |
| WO | WO-96/26702 | 9/1996 |
| WO | WO-97/44078 | 11/1997 |
| WO | WO-97/46203 | 12/1997 |
| WO | WO-99/48546 | 9/1999 |
| WO | WO-99/59665 | 11/1999 |
| WO | WO-00/47254 A1 | 8/2000 |
| WO | WO-00/69488 | 11/2000 |
| WO | WO-01/70307 A1 | 9/2001 |
| WO | WO-01/76684 A1 | 10/2001 |

(56) References Cited

FOREIGN PATENT DOCUMENTS

| WO | WO-02/02165 A2 | 1/2002 |
| WO | WO-02/20073 A2 | 3/2002 |
| WO | WO-02/28454 A2 | 4/2002 |
| WO | WO-02/40083 A2 | 5/2002 |
| WO | WO-02/49509 A2 | 6/2002 |
| WO | WO-02/068015 A2 | 9/2002 |
| WO | WO-03/006090 A1 | 1/2003 |
| WO | WO-03/024504 A2 | 3/2003 |
| WO | WO-03/026728 A1 | 4/2003 |
| WO | WO-03/033051 A1 | 4/2003 |
| WO | WO-03/059372 A3 | 7/2003 |
| WO | WO-03/072172 A2 | 9/2003 |
| WO | WO-03/074121 A1 | 9/2003 |
| WO | WO-03/090509 A2 | 11/2003 |
| WO | WO-03/090819 A2 | 11/2003 |
| WO | WO-03/090838 A1 | 11/2003 |
| WO | WO-03/103758 A1 | 12/2003 |
| WO | WO-03/103763 A1 | 12/2003 |
| WO | WO-2004/006981 A2 | 1/2004 |
| WO | WO-2004/006982 A2 | 1/2004 |
| WO | WO-2004/030716 A2 | 4/2004 |
| WO | WO-2004/030717 A2 | 4/2004 |
| WO | WO-2004/047641 A2 | 6/2004 |
| WO | WO-2004/060436 A2 | 7/2004 |
| WO | WO-2004/093648 A2 | 11/2004 |
| WO | WO-2004/098390 A2 | 11/2004 |
| WO | WO-2004/098454 A2 | 11/2004 |
| WO | WO-2004/098683 A1 | 11/2004 |
| WO | WO-2004/110526 A1 | 12/2004 |
| WO | WO-2005/000382 A2 | 1/2005 |
| WO | WO-2005/072795 A2 | 8/2005 |
| WO | WO-2005/094920 A1 | 10/2005 |
| WO | WO-2005/097237 A1 | 10/2005 |
| WO | WO-2006/015922 A1 | 2/2006 |
| WO | WO-2006/018425 A3 | 2/2006 |
| WO | WO-2006/018447 A3 | 2/2006 |
| WO | WO-2006/024671 A1 | 3/2006 |
| WO | WO-2006/024672 A1 | 3/2006 |
| WO | WO-2006/032692 A1 | 3/2006 |
| WO | WO-2006/042811 A3 | 4/2006 |
| WO | WO-2006/058435 A2 | 6/2006 |
| WO | WO-2006/072416 A2 | 7/2006 |
| WO | WO-2006/075016 A1 | 7/2006 |
| WO | WO-2006/077262 A1 | 7/2006 |
| WO | WO-2006/077263 A1 | 7/2006 |
| WO | WO-2006/084464 A1 | 8/2006 |
| WO | WO-2006/086980 A1 | 8/2006 |
| WO | WO-2006/089547 A1 | 8/2006 |
| WO | WO-2006/089548 A1 | 8/2006 |
| WO | WO-2006/089965 A1 | 8/2006 |
| WO | WO-2006/096746 A1 | 9/2006 |
| WO | WO-2006/097453 A1 | 9/2006 |
| WO | WO-2006/104806 A2 | 10/2006 |
| WO | WO-2006/108775 A2 | 10/2006 |
| WO | WO-2006/108809 A1 | 10/2006 |
| WO | WO-2006/116997 A1 | 11/2006 |
| WO | WO-2006/120253 A2 | 11/2006 |
| WO | WO-2006/125692 A1 | 11/2006 |
| WO | WO-2007/000425 A2 | 1/2007 |
| WO | WO-2007/000426 A2 | 1/2007 |
| WO | WO-2007/000427 A1 | 1/2007 |
| WO | WO-2007/038091 A2 | 4/2007 |
| WO | WO-2007/062068 A2 | 5/2007 |
| WO | WO-2007/071255 A1 | 6/2007 |
| WO | WO-2007/076641 A1 | 7/2007 |
| WO | WO-2007/087808 A1 | 8/2007 |
| WO | WO-2007/130809 A2 | 11/2007 |
| WO | WO-2008/024614 A2 | 2/2008 |
| WO | WO-2008/093063 A2 | 8/2008 |
| WO | WO-2008/151241 A2 | 12/2008 |

OTHER PUBLICATIONS

International Search Report and Written Opinion for PCT application No. PCT/US2008/082193 dated Jun. 29, 2010.
International Search Report and Written Opinion for related PCT Application No. PCT/US2007/076641 dated Feb. 27, 2008.
International Search Report dated May 15, 2008 for related PCT Application No. PCT/US2007/076679.
Office Action dated Apr. 10, 2009 from related U.S. Appl. No. 11/588,832.
Office Action dated Apr. 30, 2009 from related U.S. Appl. No. 12/027,963.
Office Action dated Aug. 4, 2009 from related U.S. Appl. No. 12/411,247.
Office Action dated Dec. 22, 2010 from related U.S. Appl. No. 12/111,815.
Office Action dated Dec. 30, 2010 from related U.S. Appl. No. 12/107,580.
Office Action dated Dec. 9, 2010 from related U.S. Appl. No. 12/099,738.
Office Action dated Jan. 14, 2010 from related U.S. Appl. No. 12/411,247.
Office Action dated Jan. 29, 2009 from related U.S. Appl. No. 11/604,172.
Office Action dated Jan. 7, 2010 from related U.S. Appl. No. 11/964,649.
Office Action dated Jul. 10, 2009 from related U.S. Appl. No. 12/411,236.
Office Action dated Jul. 21, 2010 from related U.S. Appl. No. 12/099,738.
Office Action dated Jul. 8, 2009 from related U.S. Appl. No. 11/964,649.
Office Action dated Jun. 16, 2010 from related U.S. Appl. No. 12/027,963.
Office Action dated Mar. 4, 2010 from related U.S. Appl. No. 12/099,738.
Office Action dated Nov. 10, 2009 from related U.S. Appl. No. 12/099,738.
Office Action Dated Nov. 24, 2008 from related U.S. Appl. No. 11/759,725.
Office Action dated Oct. 23, 2009 from related U.S. Appl. No. 12/411,236.
Office Action dated Sep. 24, 2009 from related U.S. Appl. No. 12/027,963.
Partial PCT Search Report dated Feb. 2, 2009 for related PCT application No. PCT/US2008/082186.
Partial PCT Search Report dated Mar. 5, 2009 from related PCT application number: PCT/US2008/082187.
Search Report dated Apr. 28, 2009 from related PCT application No. PCT/US2008/082186.
Search Report dated Feb. 3, 2009 from related PCT application No. PCT/US2008/082185.
U.S. Office Action dated Mar. 8, 2011 from related U.S. Appl. No. 12/411,247.
US Notice of Allowance dated Mar. 3, 2011 from related U.S. Appl. No. 12/107,580.
US Office Action dated Aug. 18, 2010 from related U.S. Appl. No. 12/107,580.
US Office Action dated Feb. 23, 2011 from U.S. Appl. No. 12/411,236.
US Office Action dated Mar. 29, 2011 from related U.S. Appl. No. 11/964,649.
US Office Action dated Oct. 1, 2010 U.S. Appl. No. 12/411,247.
US Office Action dated Oct. 15, 2010 from related U.S. Appl. No. 12/027,963.
US Office Action dated Sep. 28, 2010 from related U.S. Appl. No. 12/411,236.
International Search Report dated Jun. 5, 2009 from PCT Application No. PCT/US2008/082187.
Office Action from related U.S. Appl. No. 12/111,751, mailed Nov. 21, 2012, 13 pages.
US Office Action from related U.S. Appl. No. 12/099,738, mailed Dec. 20, 2012, 27 pages.
US Office Action from related U.S. Appl. No. 13/083,512, mailed Nov. 28, 2012, 18 pages.
US Notice of Allowance dated Jul. 27, 2011 from related U.S. Appl. No. 12/411,247.

(56) References Cited

OTHER PUBLICATIONS

U.S. Notice of Allowance dated Apr. 29, 2013 from related U.S. Appl. No. 12/497,345.

U.S. Notice of Allowance dated May 8, 2013 from related U.S. Appl. No. 11/515,225.

U.S. Notice of Allowance dated Jul. 30, 2013 from related U.S. Appl. No. 13/083,512.

U.S. Notice of Allowance dated Aug. 21, 2013 from related U.S. Appl. No. 12/099,738.

* cited by examiner

_US 8,597,270 B2_

AUTOMATED FILLING SYSTEMS AND METHODS

CROSS-REFERENCE TO RELATED PATENT APPLICATIONS

This application is a Divisional of U.S. application Ser. No. 12/107 580, filed Apr. 22, 2008, incorporated herein by reference in its entirety, which is a non-provisional application of U.S. Provisional Application Ser. No. 60/927,032, filed Apr. 30, 2007, entitled "Needle Inserting, Reservoir Filling, Bubble Management, Fluid Flow Connections and Infusion Medium Delivery Systems and Methods with Same," the contents of which are incorporated herein by reference in its entirety, and which is a basis for a claim of priority. Embodiments of the present invention relate to PCT International Application No. PCT/US2007/076641, filed Aug. 23, 2007, the contents of which are incorporated herein by reference in its entirety, and which claims the benefit of U.S. Provisional Application Ser. No. 60/927,032, filed Apr. 30, 2007.

BACKGROUND OF THE INVENTION

1. Field of The Invention

Embodiments of the present invention relate generally to systems and methods with reservoirs and, in specific embodiments, to systems and methods allowing for automated filling of reservoirs.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient.

Pump type delivery devices have been configured in external devices, which connect to a patient, and have also been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may contain reservoirs of fluidic media, such as, but is not limited to, insulin. External pump type delivery devices may be connected in fluid flow communication to a patient or user, for example, through a suitable hollow tubing. The hollow tubing may be connected to a hollow needle that is designed to pierce the skin of the patient and to deliver fluidic media there through. Alternatively, the hollow tubing may be connected directly to the patient as through a cannula, or the like.

Examples of some external pump type delivery devices are described in the following references: (i) Published PCT Application WO 01/70307 (PCT/US01/09139), entitled "Exchangeable Electronic Cards for Infusion Devices"; (ii) Published PCT Application WO 04/030716 (PCT/US2003/028769), entitled "Components and Methods for Patient Infusion Device"; (iii) Published PCT Application WO 04/030717 (PCT/US2003/029019), entitled "Dispenser Components and Methods for Infusion Device"; (iv) U.S. Patent Application Pub. No. 2005/0065760, entitled "Method for Advising Patients Concerning Doses Of Insulin"; and (v) U.S. Pat. No. 6,589,229, entitled "Wearable Self-Contained Drug Infusion Device", each of which is incorporated by reference herein in its entirety.

As compared to syringes and insulin pens, pump type delivery devices can be significantly more convenient to a patient, in that doses of insulin may be calculated and delivered automatically to a patient at any time during the day or night. Furthermore, when used in conjunction with glucose sensors or monitors, insulin pumps may be automatically controlled to provide appropriate doses of fluidic media at appropriate times of need, based on sensed or monitored levels of blood glucose. As a result, pump type delivery devices have become an important aspect of modern medical treatments of various types of medical conditions, such as diabetes, and the like. As pump technologies improve and doctors and patients become more familiar with such devices, external medical infusion pump treatments are expected to increase in popularity and are expected to increase substantially in number over the next decade.

SUMMARY OF THE INVENTION

Various embodiments of the present invention are directed to automated and/or assisted filling systems and methods. A system for transferring fluidic media in accordance with an embodiment of the present invention may include, but is not limited to, a first housing portion and a second housing portion. The first housing portion may have a latitudinal dimension. The second housing portion may be operatively connected to the first housing portion. The second housing portion may be for moving relative to the latitudinal dimension of the first housing portion. One of the first and second housing portions may be removably connectable to a transfer guard. The transfer guard may be for providing a fluid path from a vial to a reservoir. The other of the first and second housing portions from said one of the first and second housing portions may be operatively engageable to a plunger head positioned in the reservoir. The first and second housing portions may be configured such that fluidic media is transferred from the vial to the reservoir in a case where the one of the first and second housing portions is connected to the transfer guard, and the other of the first and second housing portions is operatively engaged to the plunger head, and the second housing portion is moved relative to the latitudinal dimension of the first housing portion.

In various embodiments, the first housing portion may have at least one tab insertable into at least one aperture of the transfer guard. The system may further include a plunger arm and a handle. The plunger arm may have a first end and a second end. The first end of the plunger arm may be connectable to the plunger head. The handle may be connected to the second end of the plunger arm.

In various embodiments, the second housing portion may have a recess. The handle may be insertable into the recess of the second housing portion. The other of the first and second housing portions from said one of the first and second housing portions may be operatively engaged to the plunger head when the handle is inserted into the recess of the second housing portion.

In various embodiments, the system may further include a fill volume control device. The fill volume control device may be supported by the one of the first and second housing portions that is removably connectable to the transfer guard. The fill volume control device may have a plurality of selectable positions, wherein each selectable position of the plurality of selectable positions may correspond to a volume of fluidic media to be transferred from the vial to the reservoir when the second housing portion moves relative to the latitudinal dimension of the first housing portion. The plunger head may be moveable in the reservoir until the handle contacts the fill volume control device.

In various embodiments, the fill volume control device may further include at least one fill volume tab. The handle may contact the fill volume control device when the handle contacts one of the at least one fill volume tab. The handle may have at least one aperture. At least one of the at least one fill volume tab may be insertable into the at least one aperture of the handle. In some embodiments, each tab of the at least one tab may be of varying lengths. In some embodiments, each fill volume tab of the at least one fill volume tab may correspond to a selectable position of the plurality of selectable positions. In some embodiments, the at least one fill volume tab may have a plurality of edges. Each edge of the plurality of edges may correspond to a selectable position of the plurality of selectable positions. In further embodiments, the fill volume control device may be at least partially rotatable about the one of the first and second housing portions that is removably connectable to the transfer guard.

In various embodiments, the system may further include a second handle connected to the fill volume control device. The second handle may be for rotating the fill volume control device to select a position of the plurality of selectable positions. In some embodiments, the one of the first and second housing portions that is removably connectable to the transfer guard may have an abutment for inhibiting advancement of the second handle beyond the abutment. In some embodiments, the system may include protrusions located at each of the plurality of selectable positions. The protrusions may be for at least partially inhibiting movement of the second handle.

In various embodiments, the system may include a door operatively connected to the second housing portion. In further embodiments, the system may further include at least one handle grip located on at least one of the second housing portion and the door of the second housing portion. In some embodiments, the system may include a door operatively connected to the first housing portion. In further embodiments, the system may further include at least one handle grip located on at least one of the first housing portion and the door of the first housing portion.

In various embodiments, the system may include a base located on a bottom end of the first housing portion. The system may further include an adhesive pad located on a bottom surface of the base. In other embodiments, the system may include a friction pad located on a bottom surface of the base. In some embodiments, the friction pad may comprise a rubber material.

In various embodiments, the system may include a pressure control valve for providing an air path between the vial and atmosphere.

In various embodiments, the transfer guard may comprise a needle for connecting the vial and the reservoir. The transfer guard may include a first end for at least partially surrounding a port of the vial when the needle of the transfer guard pierces a septum in the port of the vial. In some embodiments, the transfer guard may include a second end for at least partially surrounding a port of the reservoir when the needle of the transfer guard pierces a septum in the port of the reservoir. In further embodiments, the transfer guard may further include at least one tab located in at least one of the first end and the second end for securing at least one of the vial and the reservoir in the at least one of the first end and the second end of the transfer guard. In some embodiments, at least one of the first end and the second end may have a plurality of apertures. At least one of the vial and the reservoir may include a plurality of tabs located on the corresponding port. The plurality of tabs may be insertable into the plurality of apertures of the at least one of the first end and the second end of the transfer guard. In some embodiments, at least one of the vial and the reservoir may be at least partially rotatable about the at least one of the first end and the second end. At least one tab of the plurality of tabs may be rotatable from a position within at least one aperture of the plurality of apertures to a locked position. In further embodiments, the system may further include at least one abutment for locking at least one tab of the plurality of tabs into the locked position.

In various embodiments, the system may include at least one seal member positioned between the plunger head and the reservoir.

In various embodiments, the second housing portion may have a threaded portion. The transfer guard may have a threaded portion for engaging the threaded portion of the second housing portion when the transfer guard is connected to the second housing portion. The system may include a threaded member supported by the first housing portion. The plunger head may have a threaded portion for engaging the threaded member when the plunger head is connected to the threaded member of the first housing portion.

In various embodiments, the second housing portion may be moveable relative to the latitudinal dimension of the first housing portion between at least a first position and a second position. The transfer guard may be connectable to the second housing portion while the second housing portion is in the second position.

In various embodiments, the system may include a bias member arranged to impart a bias force on the second housing portion. The bias member may comprise a spring. The system may further include a latch for supporting the second housing portion when the second housing portion is in the second position and the latch is in a first latch position and for allowing the second housing portion to move to the first position when the latch is in a second latch position. In a case where the latch is in the first latch position, the bias member may be biased toward an expanded position and is held compressed by the second housing portion. In a case where the latch is in the second latch position, the bias member may push on the second housing portion so as to move the second housing portion to the first position. In some embodiments, the system may further include a first button for moving the latch between the first latch position and the second latch position. The first button may be for moving the latch between the second latch position and the first latch position. In further embodiments, the system may further include a second button for moving the latch between the second latch position and the first latch position.

A method for transferring fluidic media in accordance with an embodiment of the present invention, the method may include, but is not limited to, (i) providing a first housing portion having a latitudinal dimension, (ii) locating a second housing portion operatively connected to the first housing portion, the second housing portion for moving relative to the latitudinal dimension of the first housing portion, (iii) configuring one of the first and second housing portions to be removably connectable to a transfer guard, the transfer guard for providing a fluid path from a vial to a reservoir, (iv) configuring the other of the first and second housing portions from said one of the first and second housing portions to be operatively engagable to a plunger head positioned in the reservoir, and (v) configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the latitudinal dimension of the first housing portion.

In an embodiment for a system for transferring fluidic media, the system may include, but is not limited to, a holding unit and a vibrator. The holding unit may be for holding a reservoir. The holding unit may be configured such that a plunger arm that is connected to a plunger head that is within the reservoir is moveable when the holding unit is holding the reservoir and the reservoir is being filled with fluidic media. The vibrator may be for vibrating the holding unit so as to vibrate the reservoir.

In various embodiments, the vibrator may be configured to vibrate the holding unit when the holding unit is holding the reservoir and the reservoir is being filled with fluidic media, so as to vibrate the reservoir and cause air bubbles within the fluidic media to travel upwards within the reservoir. In some embodiments, the vibrator may be configured to shake the holding unit sufficiently when the holding unit is holding the reservoir and the reservoir is being filled with fluidic media so as to shake air bubbles free in the fluidic media.

In various embodiments, the system may further include a first holder and a second holder. The plunger arm may be moveable within a space between the first holder and the second holder when the reservoir is being held by the first holder and the second holder and the reservoir is being filled with fluidic media. The first holder and the second holder may be connected to the vibrator. In some embodiments, the space may be also at least partially between the plunger arm and the vibrator.

In various embodiments, the holding unit may be configured such that, when the holding unit is holding the reservoir, fluidic media is fillable into the reservoir through a port of the reservoir that is located to an opposite side of said plunger head from said plunger arm. In yet further embodiments, the holding unit may be configured such that the plunger arm is moveable in a direction toward the vibrator when the holding unit is holding the reservoir and the reservoir is being filled with fluidic media.

In various embodiments, the system may further include one or more latches for preventing the plunger arm from being moved when the holding unit is holding the reservoir and prior to a time when the reservoir is being filled with fluidic media. In further embodiments, the system may include a transfer guard for transferring fluidic media from a vial to the reservoir when the holding unit is holding the reservoir. The transfer guard may include a first end for at least partially surrounding a port of the reservoir when a needle of the transfer guard pierces a septum in the port of the reservoir. In yet further embodiments, the holding unit may be configured such that a handle connected to the plunger arm is moveable within a space between the reservoir and the vibrator when the holding unit is holding the reservoir and the reservoir is being filled with fluidic media.

A method for transferring fluidic media in accordance with an embodiment of the present invention may include, but is not limited to, (i) providing a holding unit for holding a reservoir, the holding unit configured such that a plunger arm that is connected to a plunger head that is within the reservoir is moveable when the holding unit is holding the reservoir and the reservoir is being filled with fluidic media, and (ii) locating a vibrator for vibrating the holding unit so as to vibrate the reservoir.

In an embodiment for a system for transferring fluidic media, the system may include, but is not limited to, a housing portion and a bias member. The housing portion may have a latitudinal dimension. The housing portion may be for supporting a reservoir connectable to a transfer guard for providing a fluid path from a vial to the reservoir. The bias member may be operatively engageable with a handle that is operatively engageable to a plunger head positioned in a reservoir. The bias member may be for moving the handle relative to the latitudinal dimension of the housing portion. The housing portion and the bias member may be configured such that fluidic media is transferred from the vial to the reservoir in a case where the housing portion is supporting the reservoir, the bias member is operatively engaged with the handle, the handle is operatively engaged with the plunger head, and the handle is moved relative to the latitudinal dimension of the housing portion.

In various embodiments, the system may further include a latch for supporting the handle when the latch is in a first position, and for releasing the handle to allow the handle to move when the latch is moved to a second position. The bias member may be biased toward an expanded position and held compressed by the handle in a case where the latch is in the first position and the latch is supporting the handle. The bias member may push on the handle so as to move the handle in a case where the latch is moved to the second position to release the handle. The bias member may comprise a spring.

In various embodiments, the system may include a plunger arm having a first end and a second end. The first end of the plunger arm may be connectable to the plunger head. The second end of the plunger arm may be connectable to the handle. In some embodiments, the bias member may be operatively connected between the housing portion and the handle. In other embodiments, the bias member may be operatively connected between the reservoir and the handle.

A method for transferring fluidic media in accordance with an embodiment of the present invention may include, but is not limited to, (i) providing a housing portion having a latitudinal dimension, the housing portion for supporting a reservoir connectable to a transfer guard for providing a fluid path from a vial to the reservoir, (ii) locating a bias member operatively engagable with a handle that is operatively engagable to a plunger head positioned in a reservoir, the bias member for moving the handle relative to the latitudinal dimension of the housing portion, and (iii) configuring the housing portion and the bias member such that fluidic media is transferred from the vial to the reservoir in a case where the housing portion is supporting the reservoir, the bias member is operatively engaged with the handle, the handle is operatively engaged with the plunger head, and the handle is moved relative to the latitudinal dimension of the housing portion.

A system for automated pressure equalization may include, but is not limited to, a transfer guard and a bias member. The transfer guard may include a first needle and a second needle. The first needle may have a fluid path for transferring fluidic media from an interior volume of a vial to an interior volume of a reservoir. The second needle may have a fluid path for communicating between atmosphere and the interior volume of the vial. The bias member may be connected between an end of the reservoir and a plunger head positioned in the reservoir. The bias member may be for providing a retaining force behind the plunger head as the plunger head is moved within the reservoir to transfer fluidic media from the interior volume of the vial to the interior volume of the reservoir. The bias member and the transfer guard may be configured to equalize pressure relative to atmosphere in the interior volume of the vial in a case where the second needle communicates between atmosphere and the interior volume of the vial and the plunger head is moved within the reservoir to transfer fluidic media from the interior volume of the vial to the interior volume of the reservoir.

In various embodiments, the system may include a membrane located in the fluid path of the second needle. The membrane may be for substantially preventing addition of water vapor through the second needle to the interior volume of the vial. The membrane may comprise one of a hydrophobic membrane and a hydrophilic membrane. In some embodiments, the system may include a filter located in the fluid path of the first needle. The filter may be for degassing fluidic media transferred from the interior volume of the vial to the interior volume of the reservoir. The filter may comprise one of a hydrophobic filter and a hydrophilic filter. In some embodiments, the bias member may comprise a spring.

A method for automated pressure equalization in accordance with an embodiment of the present invention may include, but is not limited to, (i) providing a transfer guard, said providing may include locating a first needle having a fluid path for transferring fluidic media from an interior volume of a vial to an interior volume of a reservoir, and locating a second needle having a fluid path for communicating between atmosphere and the interior volume of the vial, (ii) locating a bias member connected between an end of the reservoir and a plunger head positioned in the reservoir, the bias member for providing a retaining force behind the plunger head as the plunger head is moved within the reservoir to transfer fluidic media from the interior volume of the vial to the interior volume of the reservoir, and (iii) configuring the bias member and the transfer guard to equalize pressure relative to atmosphere in the interior volume of the vial in a case where the second needle communicates between atmosphere and the interior volume of the vial, and the plunger head is moved within the reservoir to transfer fluidic media from the interior volume of the vial to the interior volume of the reservoir.

DETAILED DESCRIPTION OF THE PREFERRED EMBODIMENTS

Figure 1:
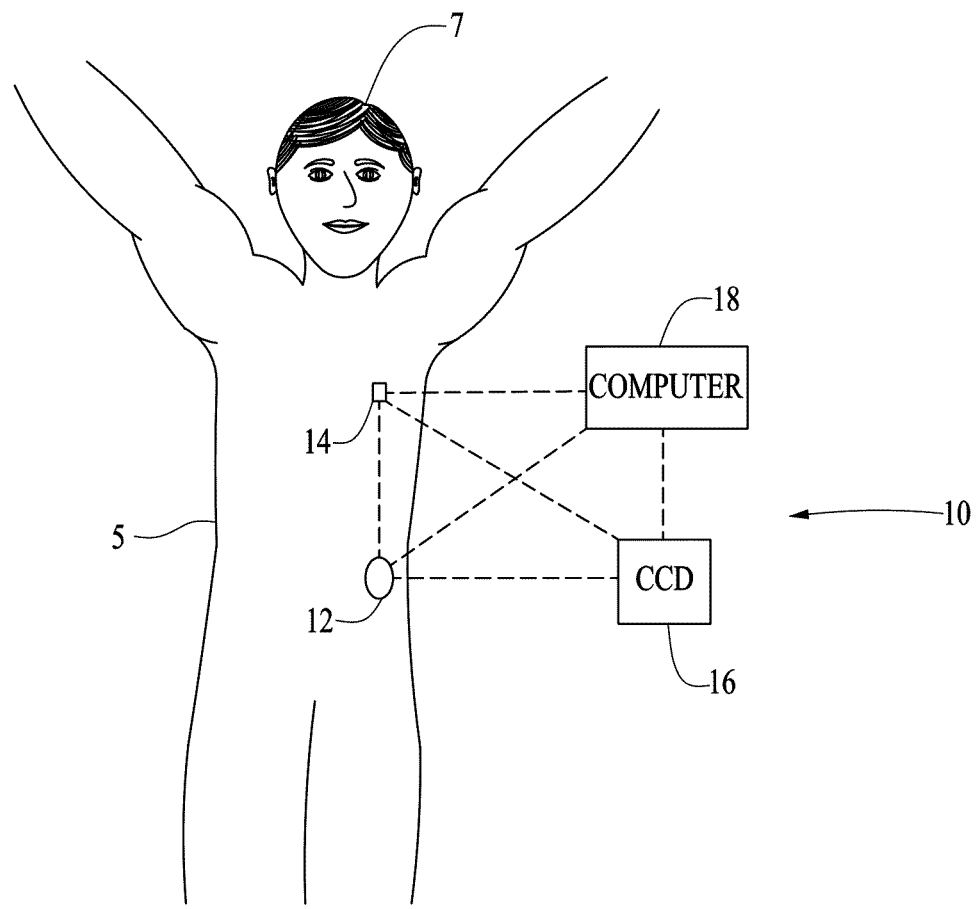
FIG. 1 illustrates a generalized representation of a system in accordance with an embodiment of the present invention.

FIG. 1 illustrates a generalized representation of a system 10 in accordance with an embodiment of the present invention. The system 10 includes a delivery device 12. The system 10 may further include a sensing device 14, a command control device (CCD) 16, and a computer 18. In various embodiments, the delivery device 12 and the sensing device 14 may be secured at desired locations on the body 5 of a patient or user-patient 7. The locations at which the delivery device 12 and the sensing device 14 are secured to the body 5 of the user-patient 7 in FIG. 1 are provided only as representative, non-limiting, examples.

Figure 7:
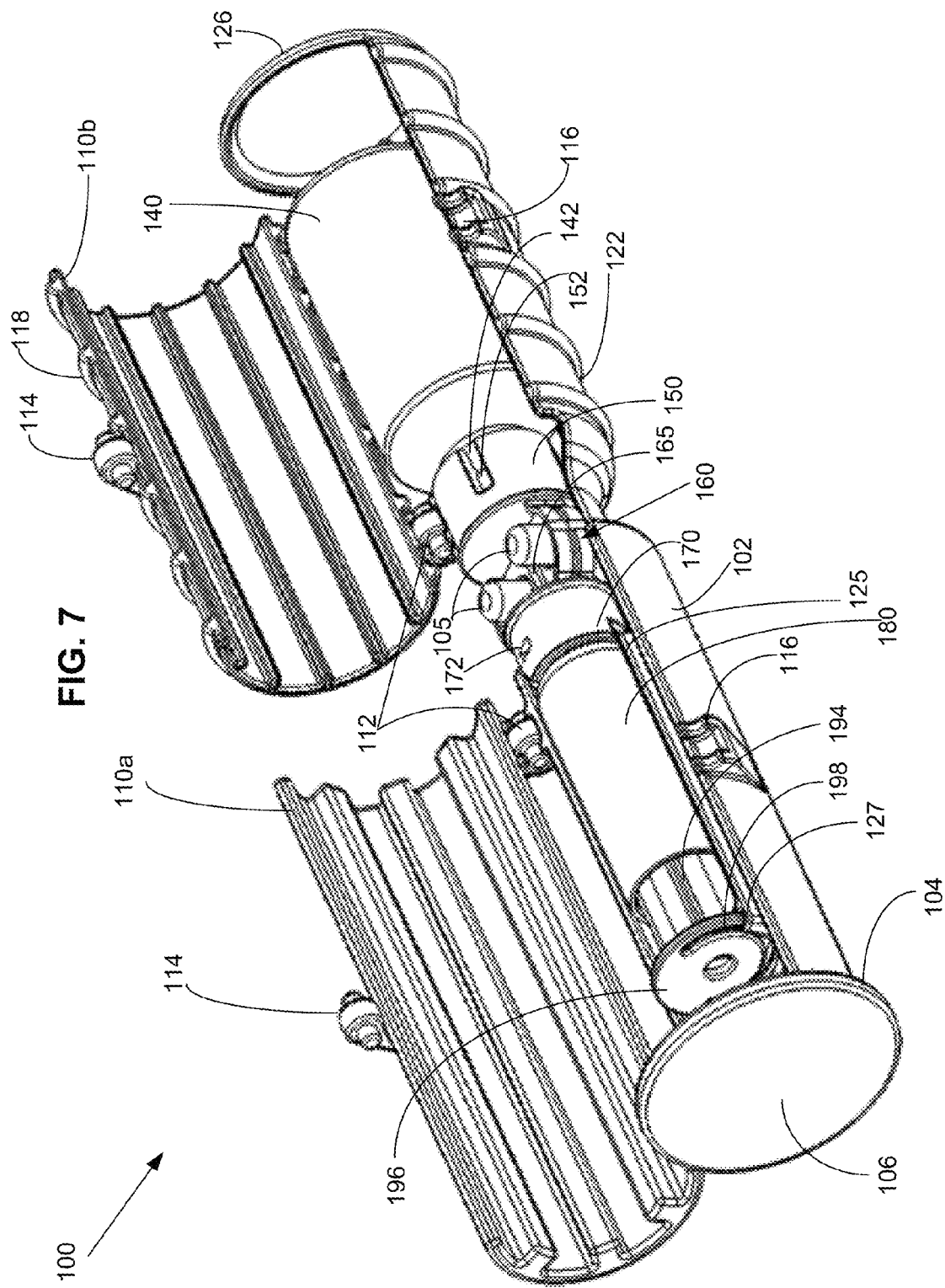
FIG. 7 illustrates a system for transferring fluidic media in accordance with an embodiment of the present invention.
Figure 8:
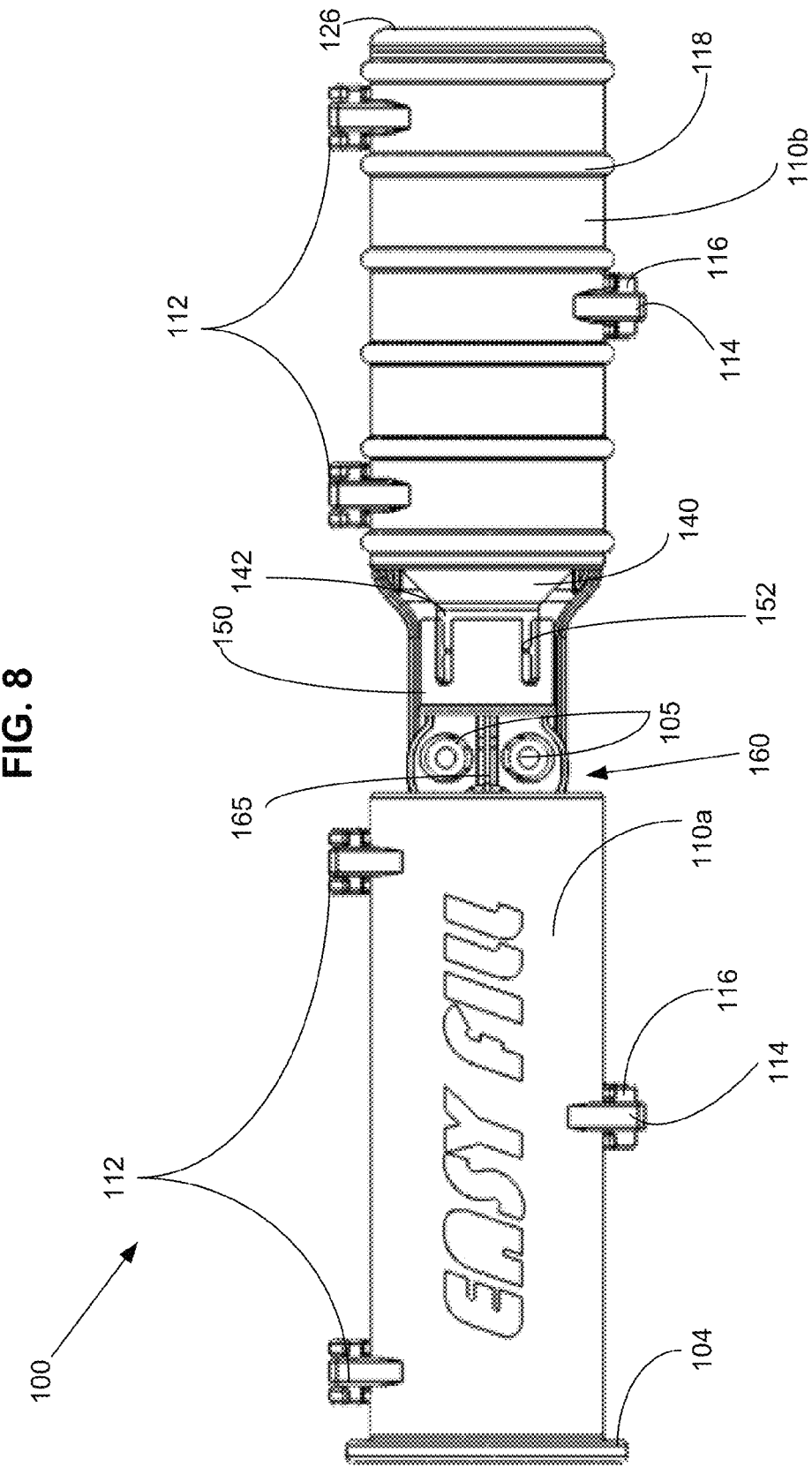
FIG. 8 illustrates a system for transferring fluidic media in accordance with an embodiment of the present invention.
Figure 9:
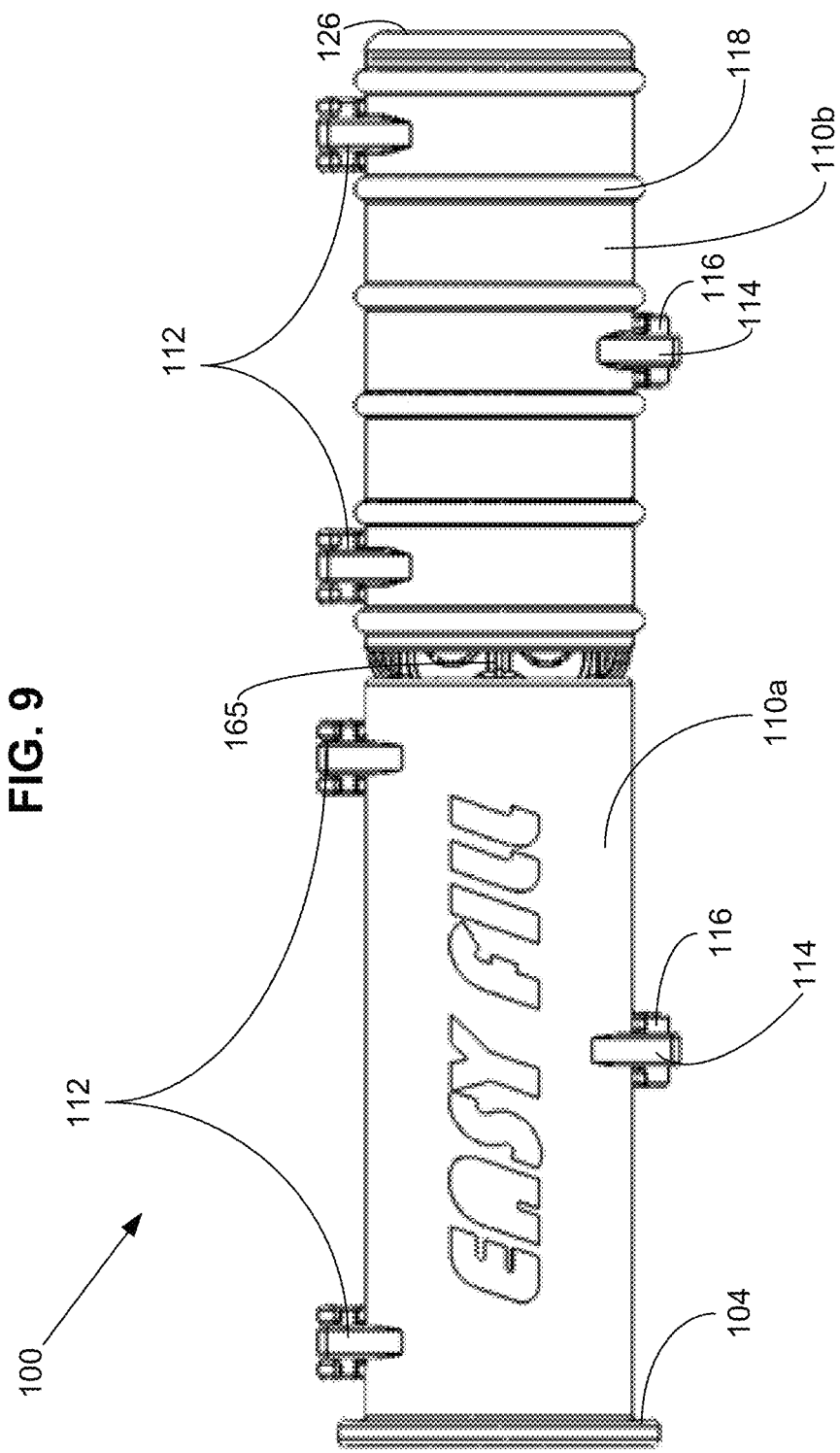
FIG. 9 illustrates a system for transferring fluidic media in accordance with an embodiment of the present invention.
Figure 10:
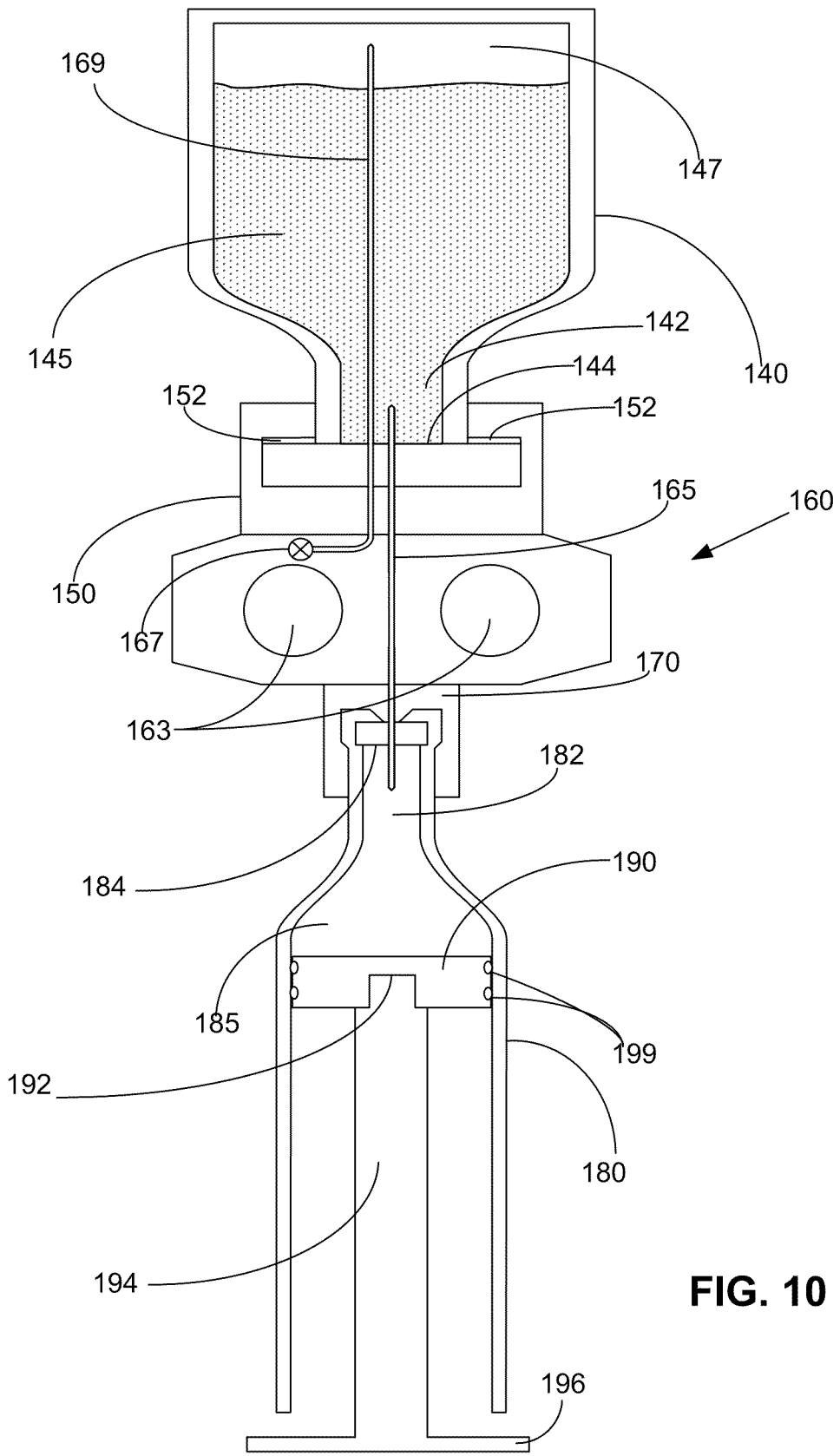
FIG. 10 illustrates a cross-sectional view of a transfer guard, a vial, and a reservoir for use with a system for transferring fluidic media in accordance with an embodiment of the present invention.

The system 10, delivery device 12, sensing device 14, CCD 16 and computer 18 may be similar to those described in the following U.S. Patent Applications that were assigned to the assignee of the present invention, however, with a reservoir and plunger configuration such as described herein with reference to FIGS. 7-8C, where each of following patent applications is incorporated herein by reference in its entirety: (i) U.S. patent application Ser. No. 11/211,095, filed Aug. 23, 2005, "Infusion Device And Method With Disposable Portion"; (ii) U.S. patent application Ser. No. 11/515,225, filed Sep. 1, 2006, "Infusion Medium Delivery Device And Method With Drive Device For Driving Plunger In Reservoir"; (iii) U.S. patent application Ser. No. 11/588,875, filed Oct. 27, 2006, "Systems And Methods Allowing For Reservoir Filling And Infusion Medium Delivery"; (iv) U.S. patent application Ser. No. 11/588,832, filed Oct. 27, 2006, "Infusion Medium Delivery Device And Method With Drive Device For Driving Plunger In Reservoir"; (v) U.S. patent application Ser. No. 11/588,847, filed Oct. 27, 2006, "Infusion Medium Delivery Device And Method With Compressible Or Curved Reservoir Or Conduit"; (vi) U.S. patent application Ser. No. 11/589,323, filed Oct. 27, 2006, "Infusion Pumps And Methods And Delivery Devices And Methods With Same"; (vii) U.S. patent application Ser. No. 11/602,173, filed Nov. 20, 2006, "Systems And Methods Allowing For Reservoir Filling And Infusion Medium Delivery"; (viii) U.S. patent application Ser. No. 11/602,052, filed Nov. 20, 2006, "Systems And Methods Allowing For Reservoir Filling And Infusion Medium Delivery"; (ix) U.S. patent application Ser. No. 11/602,428, filed Nov. 20, 2006, "Systems And Methods Allowing For Reservoir Filling And Infusion Medium Delivery"; (x) U.S. patent application Ser. No. 11/602,113, filed Nov. 20, 2006, "Systems And Methods Allowing For Reservoir Filling And Infusion Medium Delivery"; (xi) U.S. patent application Ser. No. 11/604,171, filed Nov. 22, 2006, "Infusion Medium Delivery Device And Method With Drive Device For Driving Plunger In Reservoir"; (xii) U.S. patent application Ser. No. 11/604,172, filed Nov. 22, 2006, "Infusion Medium Delivery Device And Method With Drive Device For Driving Plunger In Reservoir"; (xiii) U.S. patent application Ser. No. 11/606,703, filed Nov. 30, 2006, "Infusion Pumps And Methods And Delivery Devices And Methods With Same"; (xiv) U.S. patent application Ser. No. 11/606,836, filed Nov. 30, 2006, "Infusion Pumps And Methods And Delivery Devices And Methods With Same"; U.S. patent application Ser. No. 11/636,384, filed Dec. 8, 2006, "Infusion Medium Delivery Device And Method With Compressible Or Curved Reservoir Or Conduit"; (xv) U.S. patent application Ser. No. 11/645,993, filed Dec. 26, 2006, "Infusion Medium Delivery Device And Method With Compressible Or Curved Reservoir Or Conduit"; U.S. patent application Ser. No. 11/645,972, filed Dec. 26, 2006, "Infusion Medium Delivery System, Device And Method With Needle Inserter And Needle Inserter Device And Method"; (xvi) U.S. patent application Ser. No. 11/646,052, filed Dec. 26, 2006, "Infusion Medium Delivery System, Device And Method With Needle Inserter And Needle Inserter Device And Method"; (xvii) U.S. patent application Ser. No. 11/645,435, filed Dec. 26, 2006, "Infusion Medium Delivery System, Device And Method With Needle Inserter And Needle Inserter Device And Method"; (xviii) U.S. patent application Ser. No. 11/646,000, filed Dec. 26, 2006, "Infusion Medium Delivery System, Device And Method With Needle Inserter And Needle Inserter Device And Method"; and (xix) U.S. patent application Ser. No. 11/759,725, filed Jun. 7, 2007, "Infusion Medium Delivery Device And Method With Drive Device For Driving Plunger In Reservoir". In other embodiments, the system 10, delivery device 12, sensing device 14, CCD 16, and computer 18 may have other suitable configurations.

The delivery device 12 is configured to deliver fluidic media to the body 5 of the user-patient 7. In various embodiments, fluidic media includes a liquid, a fluid, a gel, or the like. In some embodiments, fluidic media includes a medicine or a drug for treating a disease or a medical condition. For example, fluidic media may include insulin for treating diabetes, or may include a drug for treating pain, cancer, a pulmonary disorder, HIV, or the like. In some embodiments, fluidic media includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user-patient 7. For example, the sensing device 14 may include electronics and enzymes reactive to a biological condition, such as a blood glucose level, or the like, of the user-patient 7. In various embodiments, the sensing device 14 may be secured to the body 5 of the user-patient 7 or embedded in the body 5 of the user-patient 7 at a location that is remote from the location at which the delivery device 12 is secured to the body 5 of the user-patient 7. In various other embodiments, the sensing device 14 may be incorporated within the delivery device 12.

In further embodiments, the sensing device 14 and/or the delivery device 12 may utilize a closed-loop system. Examples of sensing devices and/or delivery devices utilizing closed-loop systems may be found at, but are not limited to, the following references: (i) U.S. Pat. No. 6,088,608, entitled "Electrochemical Sensor And Integrity Tests Therefor"; (ii) U.S. Pat. No. 6,119,028, entitled "Implantable Enzyme-Based Monitoring Systems Having Improved Longevity Due To Improved Exterior Surfaces"; (iii) U.S. Pat. No. 6,589,229, entitled "Implantable Enzyme-Based Monitoring Systems Adapted for Long Term Use"; (iv) U.S. Pat. No. 6,740,072, entitled "System And Method For Providing Closed Loop Infusion Formulation Delivery"; (v) U.S. Pat. No. 6,827,702, entitled "Safety Limits For Closed-Loop Infusion Pump Control"; (vi) U.S. Pat. No. 7,323,142, entitled "Sensor Substrate And Method Of Fabricating Same"; (vii) U.S. patent application Ser. No. 09/360,342, filed Jul. 22, 1999, entitled "Substrate Sensor"; and (viii) U.S. Provisional Patent Application Ser. No. 60/318,060, filed Sep. 7, 2001, entitled "Sensing Apparatus and Process", all of which are incorporated herein by reference in their entirety.

In such embodiments, the sensing device 14 may be configured to sense a condition of the user-patient 7, such as, but not limited to, blood glucose level, or the like. The delivery device 12 may be configured to deliver fluidic media in response to the condition sensed by the sensing device 14. In turn, the sensing device 14 may continue to sense a new condition of the user-patient, allowing the delivery device 12 to deliver fluidic media continuously in response to the new condition sensed by the sensing device 14 indefinitely. In other embodiments, the sensing device 14 and/or the delivery device 12 may be configured to utilize the closed-loop system only for a portion of the day, for example only when the user-patient is asleep or awake.

Each of the delivery device 12, the sensing device 14, the CCD 16, and the computer 18 may include transmitter, receiver, or transceiver electronics that allow for communication with other components of the system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver fluidic media to the body 5 of the user-patient 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18.

Examples of the types of communications and/or control capabilities, as well as device feature sets and/or program options may be found in the following references: (i) U.S. patent application Ser. No. 10/445,477, filed May 27, 2003, entitled "External Infusion Device with Remote Programming, Bolus Estimator and/or Vibration Alarm Capabilities"; (ii) U.S. patent application Ser. No. 10/429,385, filed May 5, 2003, entitled "Handheld Personal Data Assistant (PDA) with a Medical Device and Method of Using the Same"; and (iii) U.S. patent application Ser. No. 09/813,660, filed Mar. 21, 2001, entitled "Control Tabs for Infusion Devices and Methods of Using the Same", all of which are incorporated herein by reference in their entirety.

Figure 2:
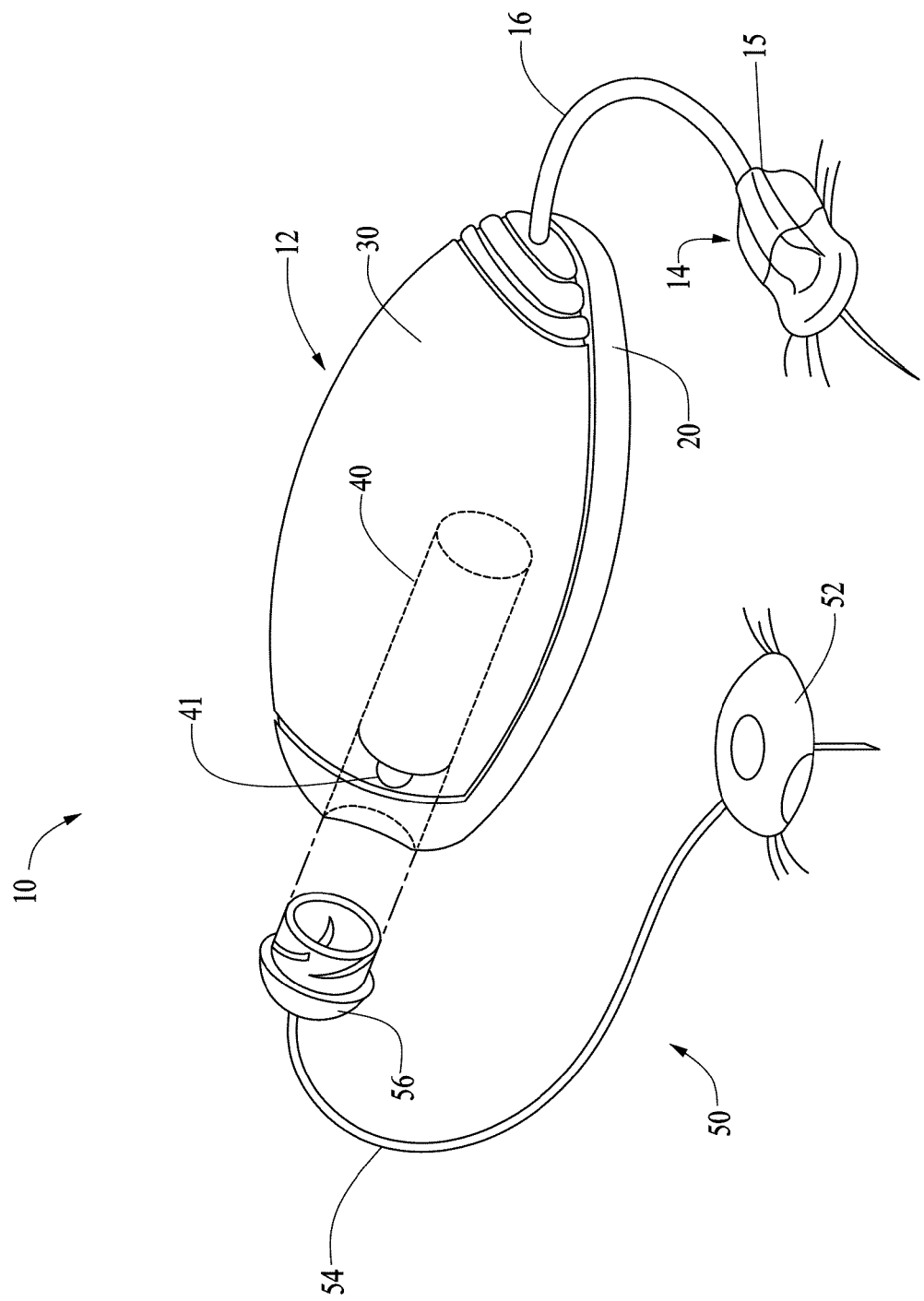
FIG. 2 illustrates an example of a system in accordance with an embodiment of the present invention.

FIG. 2 illustrates an example of the system 10 in accordance with an embodiment of the present invention. The system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir system 40. The delivery device 12 may further include an infusion path 50.

Elements of the delivery device 12 that ordinarily contact the body of a user-patient or that ordinarily contact fluidic media during operation of the delivery device 12 may be considered as a disposable portion of the delivery device 12. For example, a disposable portion of the delivery device 12 may include the disposable housing 20 and the reservoir system 40. The disposable portion of the delivery device 12 may be recommended for disposal after a specified number of uses.

On the other hand, elements of the delivery device 12 that do not ordinarily contact the body of the user-patient or fluidic media during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user-patient or fluidic media during normal operation of the delivery device 12 and, thus, may be retained for re-use with replaced disposable portions of the delivery device 12.

In various embodiments, the disposable housing 20 supports the reservoir system 40 and has a bottom surface (facing downward and into the page in FIG. 2) that is configured to secure to the body of a user-patient. An adhesive may be employed at an interface between the bottom surface of the disposable housing 20 and the skin of a user-patient, so as to adhere the disposable housing 20 to the skin of the user-patient. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the user-patient, for example against the skin of the user-patient. Thus in some embodiments, the delivery device 12 may be attached to the skin of the user-patient.

In other embodiments, the disposable housing 20 and/or the remaining portions of the delivery device 12 may be worn or otherwise attached on or underneath clothing of the user-patient. Similarly, the delivery device 12 may be supported by any suitable manner, such as, but not limited to, on a belt, in a pocket, and the like. Representative examples of such delivery devices 12 may include, but is not limited to, the MiniMed Paradigm 522 Insulin Pump, MiniMed Paradigm 722 Insulin Pump, MiniMed Paradigm 515 Insulin Pump, MiniMed Paradigm 715 Insulin Pump, MiniMed Paradigm 512R Insulin Pump, MiniMed Paradigm 712R Insulin Pump, MiniMed 508 Insulin Pump, MiniMed 508R Insulin Pump, and any other derivatives thereof.

The reservoir system 40 is configured for containing or holding fluidic media, such as, but not limited to insulin. In various embodiments, the reservoir system 40 includes a hollow interior volume for receiving fluidic media, such as, but not limited to, a cylinder-shaped volume, a tubular-shaped volume, or the like. In some embodiments, the reservoir system 40 may be provided as a cartridge or canister for containing fluidic media. In various embodiments, the reservoir system 40 is able to be refilled with fluidic media. In further embodiments, the reservoir system 40 is pre-filled with fluidic media.

The reservoir system 40 may be supported by the disposable housing 20 in any suitable manner. For example, the disposable housing 20 may be provided with projections or struts (not shown), or a trough feature (not shown), for holding the reservoir system 40. In some embodiments, the reservoir system 40 may be supported by the disposable housing 20 in a manner that allows the reservoir system 40 to be removed from the disposable housing 20 and replaced with another reservoir. Alternatively, or in addition, the reservoir system 40 may be secured to the disposable housing 20 by a suitable adhesive, a strap, or other coupling structure.

In various embodiments, the reservoir system 40 includes a port 41 for allowing fluidic media to flow into and/or flow out of the interior volume of the reservoir system 40. In some embodiments, the infusion path 50 includes a connector 56, a tube 54, and a needle apparatus 52. The connector 56 of the infusion path 50 may be connectable to the port 41 of the reservoir system 40. In various embodiments, the disposable housing 20 is configured with an opening near the port 41 of the reservoir system 40 for allowing the connector 56 of the infusion path 50 to be selectively connected to and disconnected from the port 41 of the reservoir system 40.

In various embodiments, the port 41 of the reservoir system 40 is covered with or supports a septum (not shown in FIG. 2), such as a self-sealing septum, or the like. The septum may be configured to prevent fluidic media from flowing out of the reservoir system 40 through the port 41 when the septum is not pierced. Also, in various embodiments, the connector 56 of the infusion path 50 includes a needle for piercing the septum covering the port 41 of the reservoir system 40 so as to allow fluidic media to flow out of the interior volume of the reservoir system 40.

Examples of needle/septum connectors can be found in U.S. patent application Ser. No. 10/328,393, filed Dec. 22, 2003, entitled "Reservoir Connector", which is incorporated herein by reference in its entirety. In other alternatives, non-septum connectors such as Luer locks, or the like may be used. In various embodiments, the needle apparatus 52 of the infusion path 50 includes a needle that is able to puncture the skin of a user-patient. Also, in various embodiments, the tube 54 connects the connector 56 with the needle apparatus 52 and is hollow, such that the infusion path 50 is able to provide a path to allow for the delivery of fluidic media from the reservoir system 40 to the body of a user-patient.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts.

In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to fluidic media within the reservoir system 40 to force fluidic media out of the reservoir system 40 and into an infusion path, such as the infusion path 50, for delivery to a user-patient. For example, in some embodiments, an electrically driven motor may be mounted within the durable housing 30 with appropriate linkage for operatively coupling the motor to a plunger arm (not shown in FIG. 2) connected to a plunger head (not shown in FIG. 2) that is within the reservoir system 40 and to drive the plunger head in a direction to force fluidic media out of the port 41 of the reservoir system 40 and to the user-patient.

Also, in some embodiments, the motor may be controllable to reverse direction so as to move the plunger arm and the plunger head to cause fluid to be drawn into the reservoir system 40 from a patient. The motor may be arranged within the durable housing 30 and the reservoir system 40 may be correspondingly arranged on the disposable housing 20, such that the operable engagement of the motor with the plunger head, through the appropriate linkage, occurs automatically upon the user-patient connecting the durable housing 30 with the disposable housing 20 of the delivery device 12. Further examples of linkage and control structures may be found in U.S. patent application Ser. No. 09/813,660, filed Mar. 21, 2001, entitled "Control Tabs for Infusion Devices and Methods of Using the Same", which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user-patient, a greater level of user-patient comfort may be achieved when the disposable housing 20 is secured to the skin of the user-patient. Also, a flexible disposable housing 20 may result in an increase in site options on the body of the user-patient at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

In some embodiments, the sensor 15 may include a continuous glucose sensor. The continuous glucose sensor may be implantable within the body of the user-patient. In other embodiments, the continuous glucose sensor may be located externally, for example on the skin of the user-patient, or attached to clothing of the user-patient. In such embodiments, fluid may be drawn continually from the user-patient and sensed by the continuous glucose sensor. In various embodiments, the continuous glucose sensor may be configured to sense and/or communicate with the CCD 16 continuously. In other embodiments, the continuous glucose sensor may be configured to sense and/or communicate with the CCD 16 intermittently, for example sense glucose levels and transmit information every few minutes. In various embodiments, the continuous glucose sensor may utilize glucose oxidase.

The sensor 15 may be an external sensor that secures to the skin of a user-patient or, in other embodiments, may be an implantable sensor that is located in an implant site within the body of the user-patient. In further alternatives, the sensor may be included with as a part or along side the infusion cannula and/or needle, such as for example as shown in U.S. patent application Ser. No. 11/149,119, filed Jun. 8, 2005, entitled "Dual Insertion Set", which is incorporated herein by reference in its entirety. In the illustrated example of FIG. 2, the sensor 15 is an external sensor having a disposable needle pad that includes a needle for piercing the skin of the user-patient and enzymes and/or electronics reactive to a biological condition, such as blood glucose level or the like, of the user-patient. In this manner, the delivery device 12 may be provided with sensor data from the sensor 15 secured to the user-patient at a site remote from the location at which the delivery device 12 is secured to the user-patient.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide fluidic media delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user-patient.

Figure 3:
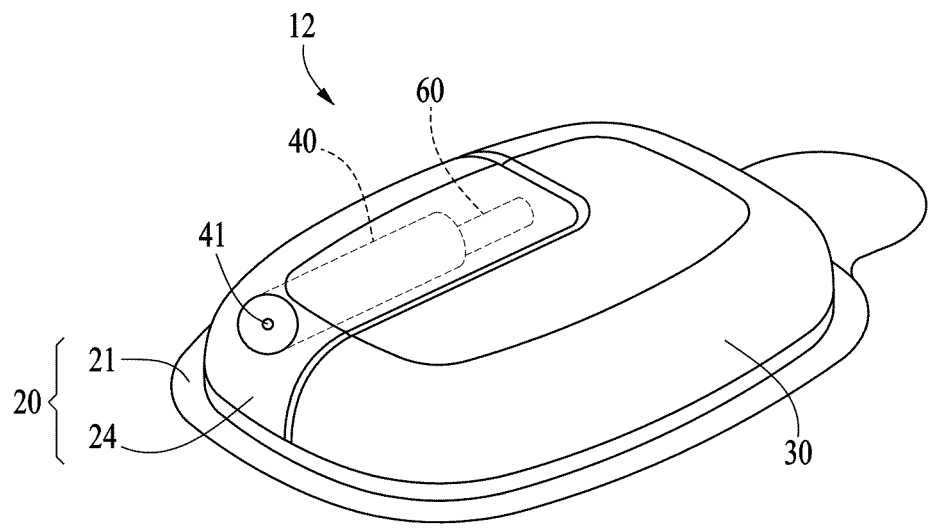
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir system 40, the delivery device 12 in the embodiment of FIG. 3 provides for the durable housing 30 to secure to the disposable housing 20 without covering the reservoir system 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user-patient. The reservoir retaining portion 24 of the disposable housing 20 is configured to house the reservoir system 40. The reservoir retaining portion 24 of the disposable housing 20 may be configured to have an opening to allow for the port 41 of the reservoir system 40 to be accessed from outside of the reservoir retaining portion 24 while the reservoir system 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger arm 60 that is connected to or that is connectable to a plunger head (not shown in FIG. 3) within the reservoir system 40.

Figure 4:
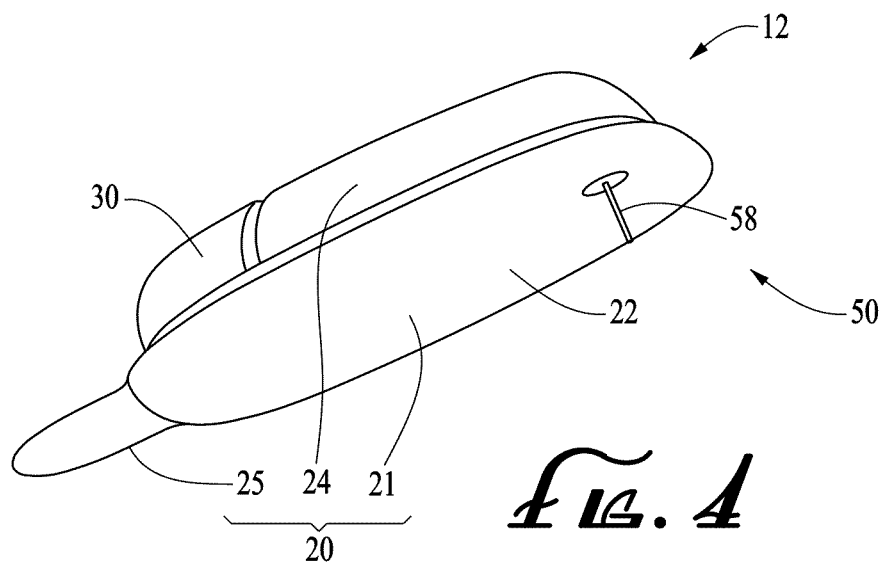
FIG. 4 illustrates a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user-patient to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user-patient under the base 21, when extended. In this manner, the needle 58 may be used to pierce the skin of the user-patient and deliver fluidic media to the user-patient.

Alternatively, the needle 58 may be extended through a hollow cannula (not shown in FIG. 4), such that upon piercing the skin of the user-patient with the needle 58, an end of the hollow cannula is guided through the skin of the user-patient by the needle 58. Thereafter, the needle 58 may be removed, leaving the hollow cannula in place, with one end of the cannula located within the body of the user-patient and the other end of the cannula in fluid flow connection with fluidic media within the reservoir system 40, to convey pumped infusion media from the reservoir system 40 to the body of the user-patient.

Figure 5A:
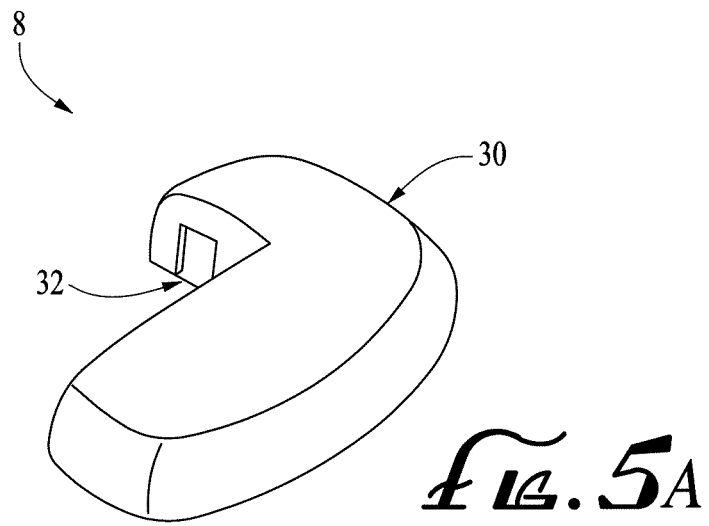
FIG. 5A illustrates a durable portion of a delivery device in accordance with an embodiment of the present invention.
Figure 5B:
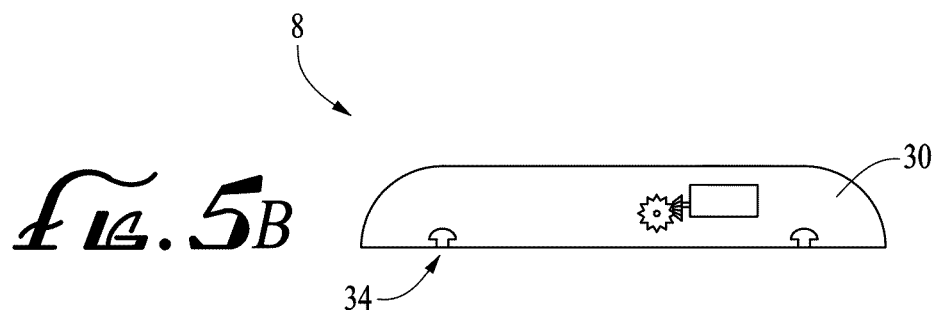
FIG. 5B illustrates a section view of a durable portion of a delivery device in accordance with an embodiment of the present invention.
Figure 5C:
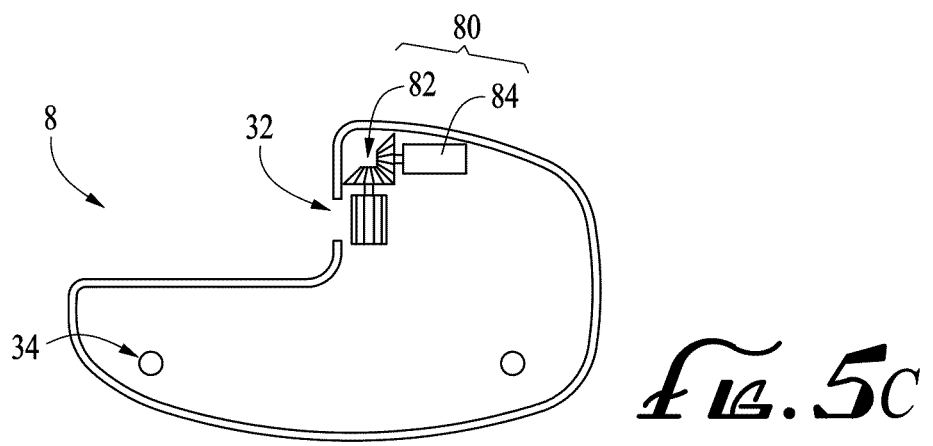
FIG. 5C illustrates a section view of a durable portion of a delivery device in accordance with an embodiment of the present invention.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82.

In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger arm 60 (refer to FIG. 3). Also, in various embodiments, the durable housing 30 may include one or more connection members 34, such as tabs, insertion holes, or the like, for connecting with the base 21 of the disposable housing 20 (refer to FIG. 3).

Figure 6A:
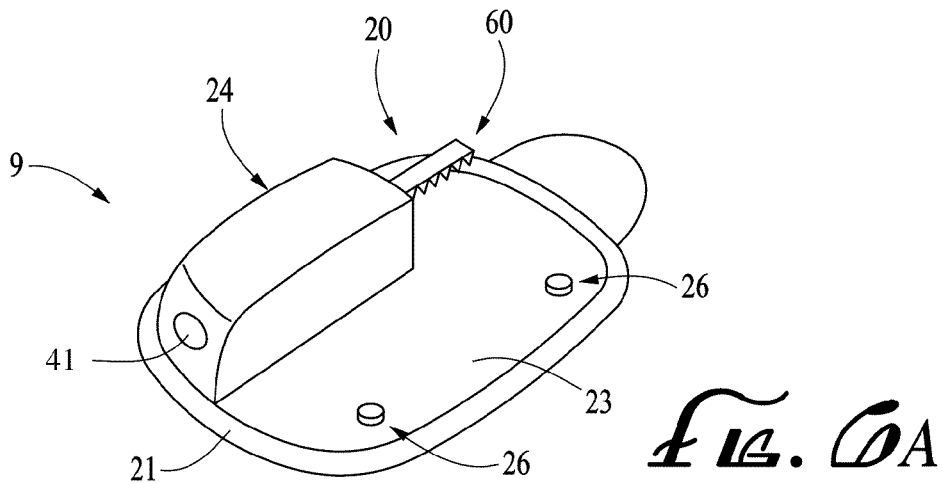
FIG. 6A illustrates a disposable portion of a delivery device in accordance with an embodiment of the present invention.
Figure 6B:
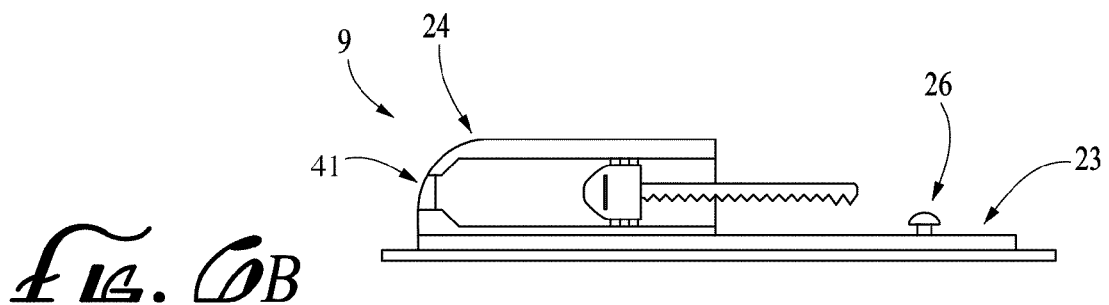
FIG. 6B illustrates a section view of a disposable portion of a delivery device in accordance with an embodiment of the present invention.
Figure 6C:
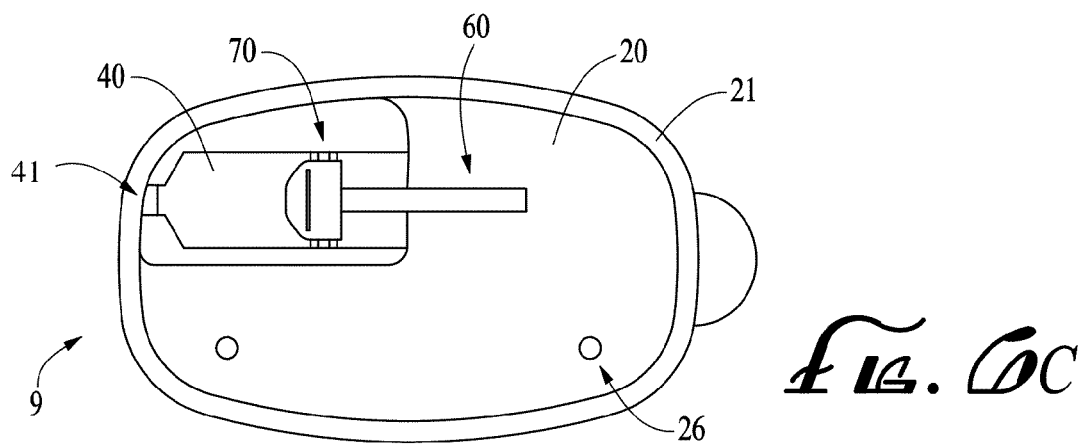
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir system 40, the plunger arm 60, and a plunger head 70. In some embodiments, the disposable housing 20 includes the base 21 and the reservoir retaining portion 24. In various embodiments, the base 21 includes a top surface 23 having one or more connection members 26, such as tabs, grooves, or the like, for allowing connections with the one or more connection members 34 of embodiments of the durable housing 30 (refer to FIG. 5B).

In various embodiments, the reservoir system 40 is housed within the reservoir retaining portion 24 of the disposable housing 20, and the reservoir system 40 is configured to hold fluidic media. Also, in various embodiments, the plunger head 70 is disposed at least partially within the reservoir system 40 and is moveable within the reservoir system 40 to allow fluidic media to fill into the reservoir system 40 and to force fluidic media out of the reservoir system 40. In some embodiments, the plunger arm 60 is connected to or is connectable to the plunger head 70.

Also, in some embodiments, a portion of the plunger arm 60 extends to outside of the reservoir retaining portion 24 of the disposable housing 20. In various embodiments, the plunger arm 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger arm 60.

When the durable housing 30 and the disposable housing 20 are fitted together with the drive device linkage portion 82 engaging or mating with the plunger arm 60, the motor 84 may be controlled to drive the drive device linkage portion 82 and, thus, move the plunger arm 60 to cause the plunger head 70 to move within the reservoir system 40. When the interior volume of the reservoir system 40 is filled with fluidic media and an infusion path is provided from the reservoir system 40 to the body of a user-patient, the plunger head 70 may be moved within the reservoir system 40 to force fluidic media from the reservoir system 40 and into the infusion path, so as to deliver fluidic media to the body of the user-patient.

In various embodiments, once the reservoir system 40 has been sufficiently emptied or otherwise requires replacement, a user-patient may simply remove the durable housing 30 from the disposable housing 20, and replace the disposable portion 9, including the reservoir system 40, with a new disposable portion having a new reservoir. The durable housing 30 may be connected to the new disposable housing of the new disposable portion, and the delivery device including the new disposable portion may be secured to the skin of a user-patient, or otherwise attached to the user-patient.

In various other embodiments, rather than replacing the entire disposable portion 9 every time the reservoir system 40 is emptied, the reservoir system 40 may be refilled with fluidic media. In some embodiments, the reservoir system 40 may be refilled while remaining within the reservoir retaining portion 24 (refer to FIG. 6B) of the disposable housing 20. Also, in various embodiments, the reservoir system 40 may be replaced with a new reservoir (not shown), while the disposable housing 20 may be re-used with the new reservoir. In such embodiments, the new reservoir may be inserted into the disposable portion 9.

With reference to FIGS. 3, 5A, 6B, and 6C, in various embodiments, the delivery device 12 includes reservoir status circuitry (not shown), and the reservoir system 40 includes reservoir circuitry (not shown). In various embodiments, the reservoir circuitry stores information such as, but not limited to, at least one of (i) an identification string identifying the reservoir system 40; (ii) a manufacturer of the reservoir system 40; (iii) contents of the reservoir system 40; and (iv) an amount of contents in the reservoir system 40. In some embodiments, the delivery device 12 includes the reservoir status circuitry (not shown), and the reservoir status circuitry is configured to read data from the reservoir circuitry when the reservoir system 40 is inserted into the disposable portion 9.

In various embodiments, the reservoir status circuitry is further configured to store data to the reservoir circuitry after at least some of the contents of the reservoir system 40 have been transferred out of the reservoir system 40, so as to update information in the reservoir circuitry related to an amount of contents still remaining in the reservoir system 40. In some embodiments, the reservoir status circuitry is configured to store data to the reservoir circuitry, so as to update information in the reservoir circuitry related to an amount of contents still remaining in the reservoir system 40, when the reservoir system 40 is inserted into the disposable portion 9. In some embodiments, the delivery device 12 includes the reservoir status circuitry (not shown) and the reservoir system 40 includes the reservoir circuitry (not shown), and the reservoir status circuitry selectively inhibits use of the delivery device 12 or selectively provides a warning signal based on information read by the reservoir status circuitry from the reservoir circuitry.

FIGS. 7-10 illustrate a system 100 for transferring fluidic media in accordance with an embodiment of the present invention. The system 100 may include, but is not limited to, a first housing portion 102, a second housing portion 122, a vial 140, a reservoir 180, a plunger head 190, a plunger arm 194, a handle 196, and a transfer guard 160. The first housing portion 102 and the second housing portion 122 may be configured such that the second housing portion 122 is moveable relative to a latitudinal dimension of the first housing portion 102. For example, the first housing portion 102 and the second housing portion 122 may be slideably connected such that the second housing portion 122 may slide into the first housing portion 102 when a user pushes the second housing portion 122 into the first housing portion 102.

The second housing portion 122 may have a portion 125 substantially extending into the first housing portion 102. The portion 125 of the second housing portion 122 may have a recess 127 located on a distal end of the portion 125 of the second housing portion 122. The recess 127 may be for receiving the handle 196 when the transfer guard 160 is installed on the first housing portion 102. The handle 196 and the recess 127 may be configured such that the handle 196 is able to fit within or snap together with the recess 127 to fit the handle 196 within the recess 127. The system 100 may include a base 104 located on a bottom surface of the first housing portion 102 for standing the system 100 vertically on a suitable surface, such as a table top, countertop, or the like. In some embodiments, the base 104 may have an adhesive bottom 106 for attaching the system 100 to the suitable surface. In some embodiments, the base 104 may include a friction pad (not shown), which may be made of rubber, or the like located on the bottom surface of the base 104 to prevent the system 100 from slipping during use of the system 100.

The vial 140 may include a septum 144 located at a port 142 of the vial 140. The vial 140 may be for containing fluidic media. The reservoir 180 may have an interior volume 185 for containing fluidic media. The plunger head 190 may be located within the reservoir 180 and may be moveable within the reservoir 180 to expand or contract the interior volume 185 of the reservoir 180. The plunger head 190 may be connected to the plunger arm 194. The handle 196 may be connected to an end of the plunger arm 194 opposite from the end connected to the plunger head 190. The reservoir 180 may include a septum 184 located at a port 182 of the reservoir 180. The plunger head 190 may include at least one seal member 199, such as an o-ring, or the like to facilitate movement within the reservoir 180 and/or to substantially prevent fluidic media from flowing between the plunger head 190 and the reservoir 180.

The transfer guard 160 may include a needle 165 for providing a fluid path from an interior volume 145 of the vial 140 to the interior volume 185 of the reservoir 180. The transfer guard 160 may be configured such that when the vial 140 is attached to the transfer guard 160, the needle 165 pierces the septum 144 of the vial 140. The transfer guard 160 may be further configured such that when the reservoir 180 is attached to the transfer guard 160, the needle 165 pierces the septum 184 of the reservoir 180. Thus, the transfer guard 160 may allow for establishing the fluid path from the vial 140 to the reservoir 180 through the needle 165.

In some embodiments, the transfer guard 160 may include a second needle 169. The second needle 169 may be able to pierce the septum 144 of the vial 140 when the vial 140 is connected to the transfer guard 160. An end of the second needle 169 may be located within a headspace 147 of the vial 140 above fluidic media within the interior volume 145 of the vial 140 in a case where the transfer guard 160 is connected to the vial 140. In other embodiments, the end of the second needle 169 may be in contact with fluidic media within the interior volume 145 of the vial 140 in a case where the transfer guard 160 is connected to the vial 140. Another end of the second needle 169 may be connected to a check valve 167, such as a one-way valve, or the like. The check valve 167 may allow air to enter the interior volume 145 of the vial 140 through the second needle 169. In some embodiments, the check valve 167 may substantially prevent liquid from coming out of the vial 140 through the second needle 169 and/or the check valve 167. In various embodiments, the second needle 169 may allow for venting the headspace 147 or the interior volume 145 of the vial 140 to atmosphere to facilitate the transfer of fluidic media from the vial 140 to the reservoir 180.

The transfer guard 160 may have a first end 150 for supporting the vial 140. The port 142 of the vial 140 may be insertable into the first end 150 of the transfer guard 160. As described above, the septum 144 of the vial 140 may be pierced by the needle 165 of the transfer guard 160 when the vial 140 is inserted into the first end 150 of the transfer guard 160. The first end 150 of the transfer guard 160 may include a tab 152 for securing the vial 140 within the first end 150 of the transfer guard 160 once the vial 140 is inserted in the first end 150 of the transfer guard 160. The first end 150 of the transfer guard 160 may be configured to include multiple tabs 152 or one or more annular ribs for example, to secure the vial 140 in the first end 150 of the transfer guard 160.

The transfer guard 160 may have a second end 170 for supporting the reservoir 180. The port 182 of the reservoir 180 may be insertable into the second end 170 of the transfer guard 160. The septum 184 of the reservoir 180 may be pierced by the needle 165 of the transfer guard 160 when the reservoir 180 is inserted into the second end 170 of the transfer guard 160.

In some embodiments, as shown in FIGS. 10 and 27-29, the second end 170 of the transfer guard 160 may include depressions or apertures 176 located within the second end 170 of the transfer guard 160. The port 182 of the reservoir 180 may include one or more tabs 186 for inserting into the apertures 176 located in the second end 170 of the transfer guard 160. The port 182 of the reservoir 180 may further include a second tab 188 attached to each of the tabs 186. The reservoir 180 and port 182 may be configured to be rotatable, at least partially, about the second end 170 of the transfer guard 160. The second end 170 of the transfer guard 160 may further include one or more depressions 178 for receiving the second tabs 188 when the reservoir 180 and port 182 are rotated to secure the reservoir 180 to the transfer guard 160. As a result, the port 182 of the reservoir 180 may be inserted into the second end 170 of the transfer guard 160 so that the tabs 186 fit into the apertures 176 and then rotated slightly until the second tabs 188 fit into place within the depressions 178 to lock the reservoir 180 into the second end 170 of the transfer guard 160.

In some embodiments, the first end 150 and the vial 140 may be configured in the same manner as described above so that the tabs 186 fit into the apertures 176 and then rotate slightly until the second tabs 188 fit into place within the depressions 178. In some embodiments, the second end 170 of the transfer guard 160 may be configured to include a tab 152 for securing the reservoir 180 within the second end 170 of the transfer guard 160 similar to what was described above with respect to the first end 150 of the transfer guard 160.

Referring back to FIGS. 7-10, once the vial 140 and the reservoir 180 have been inserted in the first end 150 and the second end 170 of the transfer guard 160 respectively, the transfer guard 160 may be ready to be installed to the first housing portion 102. For example, in some embodiments, the first housing portion 102 may include a mating piece 105 for connecting the transfer guard 160 to the first housing portion 102. The transfer guard 160 may include one or more apertures 163. The mating piece 105 of the first housing portion 102 may be insertable within the one or more apertures 163 to connect the transfer guard 160 to the first housing portion 102. The handle 196 may be fitted within the recess 127 after the transfer guard 160 is affixed to the first housing portion 102. Alternatively, the handle 196 may be fitted within the recess 127 before or concurrently with the transfer guard 160 being affixed to the first housing portion 102. In other embodiments, at least one of the reservoir 180 and the vial 140 may be connected to the transfer guard 160 after the transfer guard 160 has been installed to the first housing portion 102. In various embodiments, the transfer guard 160 may be attachable to the first housing portion 102 by other means, such as, but not limited to, screwing the transfer guard 160 to the first housing portion 102, or the like.

In some embodiments, the plunger arm 194 and the handle 196 may be connected to the portion 125 of the second housing portion 122 and connected to the plunger head 190 when the transfer guard 160 is installed to the first housing portion 102. For example, the plunger arm 194 may have a threaded end (not shown) opposite from the handle 196 for engaging a threaded recess 192 or portion within the plunger head 190. The reservoir 180 or the plunger head 190 could then be rotated to engage the plunger head 190 with the threaded end (not shown) of the plunger arm 194.

In some embodiments, the first housing portion 102 and the second housing portion 122 may be connected to doors 110a, 110b, respectively. For example, the doors 110a, 110b may be pivotally connected to the first housing portion 102 and the second housing portion 122 with hinges 112. The doors 110a, 110b may be held closed against the first housing portion 102 and the second housing portion 122 with clasps 116. The system 100 may initially have both doors 110a, 110b closed. The doors 110a, 110b may be opened by the user. Once the doors 110a, 110b are open, the transfer guard 160 along with the vial 140 and the reservoir 180 may be connected to the first housing portion 102 by way of the mating piece 105 as shown in FIG. 7, and/or as described above. The handle 196 may be fitted into the recess 127 of the second housing portion 122 when the transfer guard 160 along with the vial 140 and the reservoir 180 are connected to the first housing portion 102. Thereafter, one or both of the doors 110a, 110b may be closed so that the user can use the system 100, as shown in FIG. 8.

Referring to FIGS. 7-10, the system 100 may allow for simplifying a filling process of the reservoir 180 with fluidic media from the vial 140. The user may push the second housing portion 122 against the first housing portion 102. For example, the user may push on a top surface 126 of the second housing portion 122 against the first housing portion 102 or grip the second housing portion 122 and door 110*b* and advance the second housing portion 122 and the door 110*b* toward the first housing portion 102. This may cause the portion 125 of the second housing portion 122 and the recess 127 of the second housing portion 122 to slide or otherwise move further along the first housing portion 102 toward the base 104 of the first housing portion 102. As a result, the handle 196 fitted within the recess 127 may be pulled away from the reservoir 180. As the handle 196 moves away from the reservoir 180, the attached plunger arm 194 and plunger head 190 may be moved within the reservoir 180 to increase the interior volume 185 of the reservoir 180. The movement of the plunger head 190 may draw fluidic media within the vial 140 through the transfer guard 160, for example through the needle 165, to the interior volume 185 of the reservoir 180, thus filling the reservoir 180. In some embodiments, the plunger head 190 may be substantially advanced within the reservoir 180 toward the port 182 of the reservoir 180 before starting the filling process of the reservoir 180.

The system 100 may be used to fill the interior volume 185 of the reservoir 180, or a portion thereof. The system 100 may be configured such that the interior volume 185 of the reservoir 180 is completely filled or sufficiently filled when the second housing portion 122 is pushed completely into the first housing portion 102.

Once the user has finished using the system 100 during the filling process, for example once the interior volume 185 of the reservoir 180 is sufficiently filled, one or both of the doors 110*a*, 110*b* may be opened to remove the transfer guard 160 along with the reservoir 180 and vial 140. Alternatively, the user may remove one or more of those components, such as only the reservoir 180, while leaving the other components in the system 100 for future use.

In some embodiments, the system 100 may include textured areas 118 or the like on one or more of the first housing portion 102, the second housing portion 122, and the doors 110*a*, 110*b*. The textured areas 118 may allow for increased handling or gripping of the system 100. The textured areas 118 may be, for example, a series of annular ribs that surround the system 100 or a portion thereof as exemplified in FIGS. 7-9.

FIGS. 11-16 illustrate a system 200 for transferring fluidic media and a portion thereof in accordance with an embodiment of the present invention. The system 200 may include, but is not limited to, a first housing portion 202, a second housing portion 222, a vial 240, a reservoir 280, a plunger head 290, a plunger arm 294, a handle 296, and a transfer guard 260. The first housing portion 202 and the second housing portion 222 may be configured such that the second housing portion 222 is moveable relative to a latitudinal dimension of the first housing portion 202. For example, the first housing portion 202 and the second housing portion 222 may be slideably connected such that the second housing portion 222 may slide over the first housing portion 202 when a user pushes the second housing portion 222 into the first housing portion 202.

The second housing portion 222 may be disposed around the first housing portion 202 to at least substantially envelop an outer surface 202*a* and an inner surface 202*b* of the first housing portion 202. The second housing portion 222 may have a portion 225 located near the inner surface 202*b*. The portion 225 of the second housing portion 222 may have a recess 227 located on a distal end of the portion 225 of the second housing portion 222 for receiving the handle 296 when the transfer guard 260 is installed to the first housing portion 202. The handle 296 and the recess 227 may be configured such that the handle 296 is able to fit within or snap together within the recess 227 to fit the handle 296 in the recess 227. The system 200 may include a base 204 located on a bottom surface of the first housing portion 202 for standing the system 200 vertically on a suitable surface, such as a table top, countertop, or the like. In some embodiments, the base 204 may have an adhesive bottom 206 for attaching the system 200 to the suitable surface. In some embodiments, the base 204 may include a friction pad (not shown), which may be made of rubber, or the like located on the bottom surface of the base 204 to prevent the system 200 from slipping during use of the system 100.

The vial 240 may include a septum 244 located at a port 242 of the vial 240, and the vial 240 may be for containing fluidic media. The reservoir 280 may have an interior volume 285 for containing fluidic media. The plunger head 290 may be located within the reservoir 280 and may be moveable within the reservoir 280 to expand or contract the interior volume 285 of the reservoir 280. The plunger head 290 may be connected to the plunger arm 294. The handle 296 may be connected to an end of the plunger arm 294 opposite from the end connected to the plunger head 290. The reservoir 280 may include a septum 284 located at a port 282 of the reservoir 280. The plunger head 290 may include at least one seal member 299, such as an o-ring, or the like to facilitate movement within the reservoir 280 and/or to substantially prevent fluidic media from flowing between the plunger head 290 and the reservoir 280.

The transfer guard 260 may include a needle 265 for providing a fluid path from an interior volume 245 of the vial 240 to the interior volume 285 of the reservoir 280. The transfer guard 260 may be configured such that when the vial 240 is attached to the transfer guard 260, the needle 265 pierces the septum 244 of the vial 240. The transfer guard 260 may be further configured such that when the reservoir 280 is attached to the transfer guard 260, the needle 265 pierces the septum 284 of the reservoir 280. Thus, the transfer guard 260 may allow for establishing the fluid path from the vial 240 to the reservoir 280 through the needle 265.

In some embodiments, the transfer guard 260 may include a second needle 269. The second needle 269 may be able to pierce the septum 244 of the vial 240 when the vial 240 is connected to the transfer guard 260. An end of the second needle 269 may be located within a headspace 247 of the vial 240 above fluidic media within the interior volume 245 of the vial 240 in a case where the transfer guard 260 is connected to the vial 240. In other embodiments, the end of the second needle may be in contact with fluidic media within the interior volume 245 of the vial 240 in a case where the transfer guard 260 is connected to the vial 240. Another end of the second needle 269 may be connected to a check valve 267, such as a one-way valve, or the like. The check valve 267 may allow air to enter the interior volume 245 of the vial 240 through the second needle 269. In some embodiments, the check valve 267 may substantially prevent liquid from coming out of the vial 240 through the second needle 269 and/or the check valve 267. In various embodiments, the second needle 269 may allow for venting the headspace 247 or the interior volume 245 of the vial 240 to atmosphere to facilitate the transfer of fluidic media from the vial 240 to the reservoir 280.

The transfer guard 260 may have a first end 250 for supporting the vial 240. The port 242 of the vial 240 may be insertable into the first end 250 of the transfer guard 260. As mentioned, the septum 244 of the vial 240 may be pierced by the needle 265 of the transfer guard 260 when the vial 240 is inserted into the first end 250 of the transfer guard 260. The first end 250 of the transfer guard 260 may include a tab 252 for securing the vial 240 within the first end 250 of the transfer guard 260 once the vial 240 is inserted in the first end 250 of the transfer guard 260. The first end 250 of the transfer guard 260 may be configured to include multiple tabs 252 or one or more annular ribs for example, to secure the vial 240 within the first end 250 of the transfer guard 260.

The transfer guard 260 may have a second end 270 for supporting the reservoir 280. The port 282 of the reservoir 280 may be insertable into the second end 270 of the transfer guard 260. The septum 284 of the reservoir 280 may be pierced by the needle 265 of the transfer guard 260 when the reservoir 280 is inserted into the second end 270 of the transfer guard 260.

In some embodiments, the second end 270 of the transfer guard 260 may include depressions or apertures (such as 176 in FIG. 28) located within the second end 270 of the transfer guard 260. The port 282 of the reservoir 280 may include one or more tabs (such as 186 in FIG. 29) for inserting into the apertures (176 in FIG. 28) located in the second end 270 of the transfer guard 260. The port 282 of the reservoir 280 may further include a second tab (such as 188 in FIG. 29) attached to each of the tabs (186 in FIG. 29). The reservoir 280 and port 282 may be configured to be rotateable, at least partially, about the second end 270 of the transfer guard 260. The second end 270 of the transfer guard 260 may further include one or more depressions (such as 178 in FIG. 28) for receiving the second tabs (188 in FIG. 29) when the reservoir 280 and port 282 are rotated to secure the reservoir 280 to the transfer guard 260. As a result, the port 282 of the reservoir 280 may be inserted into the second end 270 of the transfer guard 260 so that the tabs (186 in FIG. 29) fit into the apertures (176 in FIG. 28) and then rotated slightly until the second tabs (188 in FIG. 29) fit into place within the depressions (178 in FIG. 28) to lock the reservoir 280 into the second end 270 of the transfer guard 260.

Figure 28:
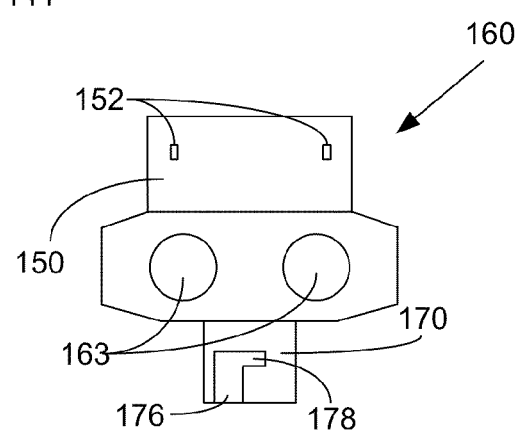
FIG. 28 illustrates a cross-sectional view of a transfer guard for use with a system for transferring fluidic media in accordance with an embodiment of the present invention.
Figure 29:
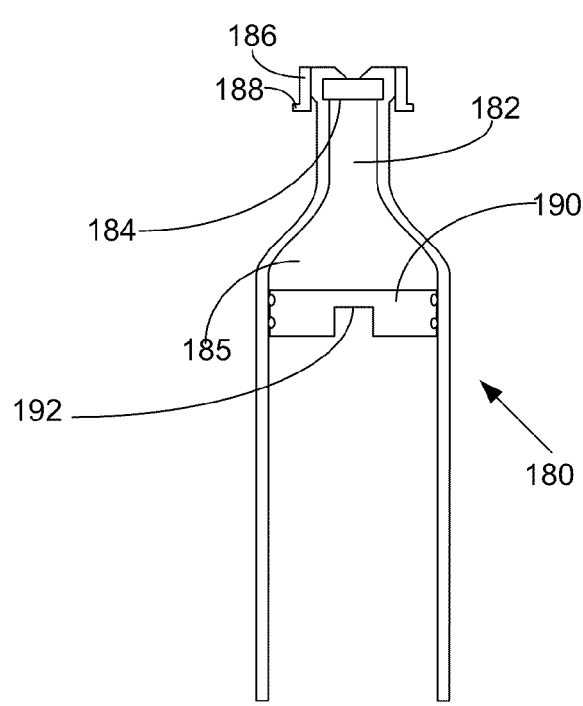
FIG. 29 illustrates a cross-sectional view of a reservoir for use with a system for transferring fluidic media in accordance with an embodiment of the present invention.

In some embodiments, the first end 250 of the transfer guard 260 and the vial 240 may be configured in the same manner as described above so that the tabs (186 in FIG. 29) fit into the apertures (176 in FIG. 28) and then rotate slightly until the second tabs (188 in FIG. 29) fit into place within the depressions (178 in FIG. 28). In some embodiments, the second end 270 of the transfer guard 260 may be configured to include a tab 252 for securing the reservoir 280 within the second end 270 of the transfer guard 260 similar to what was described above with respect to the first end 250 of the transfer guard 260.

Once the vial 240 and the reservoir 280 have been inserted in the first end 250 and the second end 270 of the transfer guard 260 respectively, the transfer guard 260 may be ready to be installed to the first housing portion 202. For example, in some embodiments, the first housing portion 202 may include a mating piece 205 for connecting the transfer guard 260 to the first housing portion 202. The transfer guard 260 may include one or more apertures 263. The mating piece 205 of the first housing portion 202 may be insertable within the one or more apertures 263 to connect the transfer guard 260 to the first housing portion 202. The handle 296 may be fitted within the recess 227 after the transfer guard 260 is affixed to the first housing portion 202. Alternatively, the handle 296 may be fitted within the recess 227 before or concurrently with the transfer guard 260 being affixed to the first housing portion 202. In other embodiments, at least one of the reservoir 280 and the vial 240 may be connected to the transfer guard 260 after or before the transfer guard 260 has been installed to the first housing portion 202. In various embodiments, the transfer guard 260 may be attachable to the first housing portion 202 by other means, such as, but not limited to, screwing the transfer guard 260 to the first housing portion 202, or the like.

In some embodiments, the plunger arm 294 and the handle 296 may be connected to the portion 225 of the second housing portion 222 and connected to the plunger head 290 when the transfer guard 260 is installed to the first housing portion 202. For example, the plunger arm 294 may have a threaded end (not shown) opposite from the handle 296 for engaging a threaded recess 292 or portion within the plunger head 290. The reservoir 280 or the plunger head 290 could then be rotated to engage the plunger head 290 with the threaded end (not shown) of the plunger arm 294.

Figure 11:
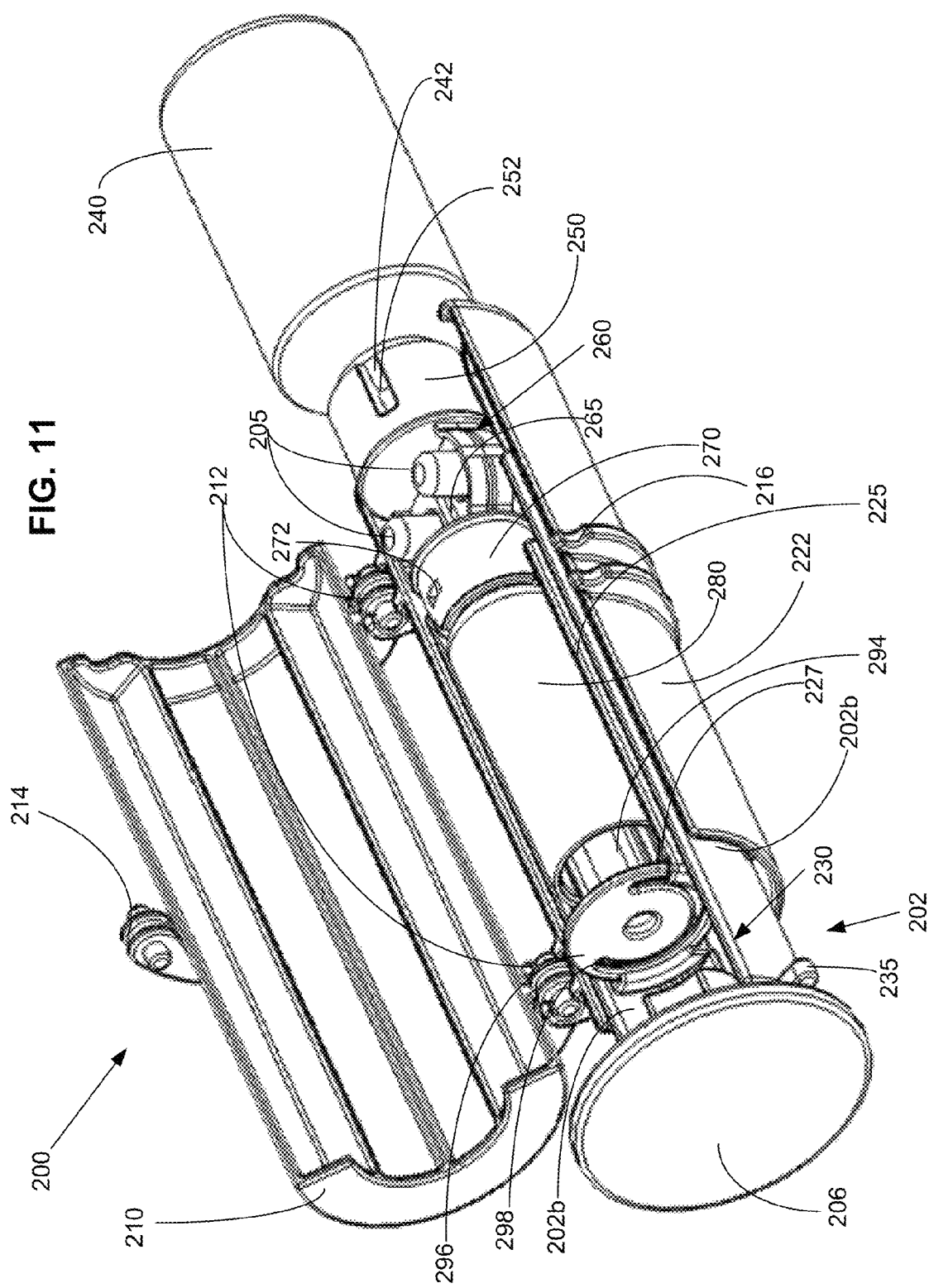
FIG. 11 illustrates a system for transferring fluidic media in accordance with an embodiment of the present invention.
Figure 12:
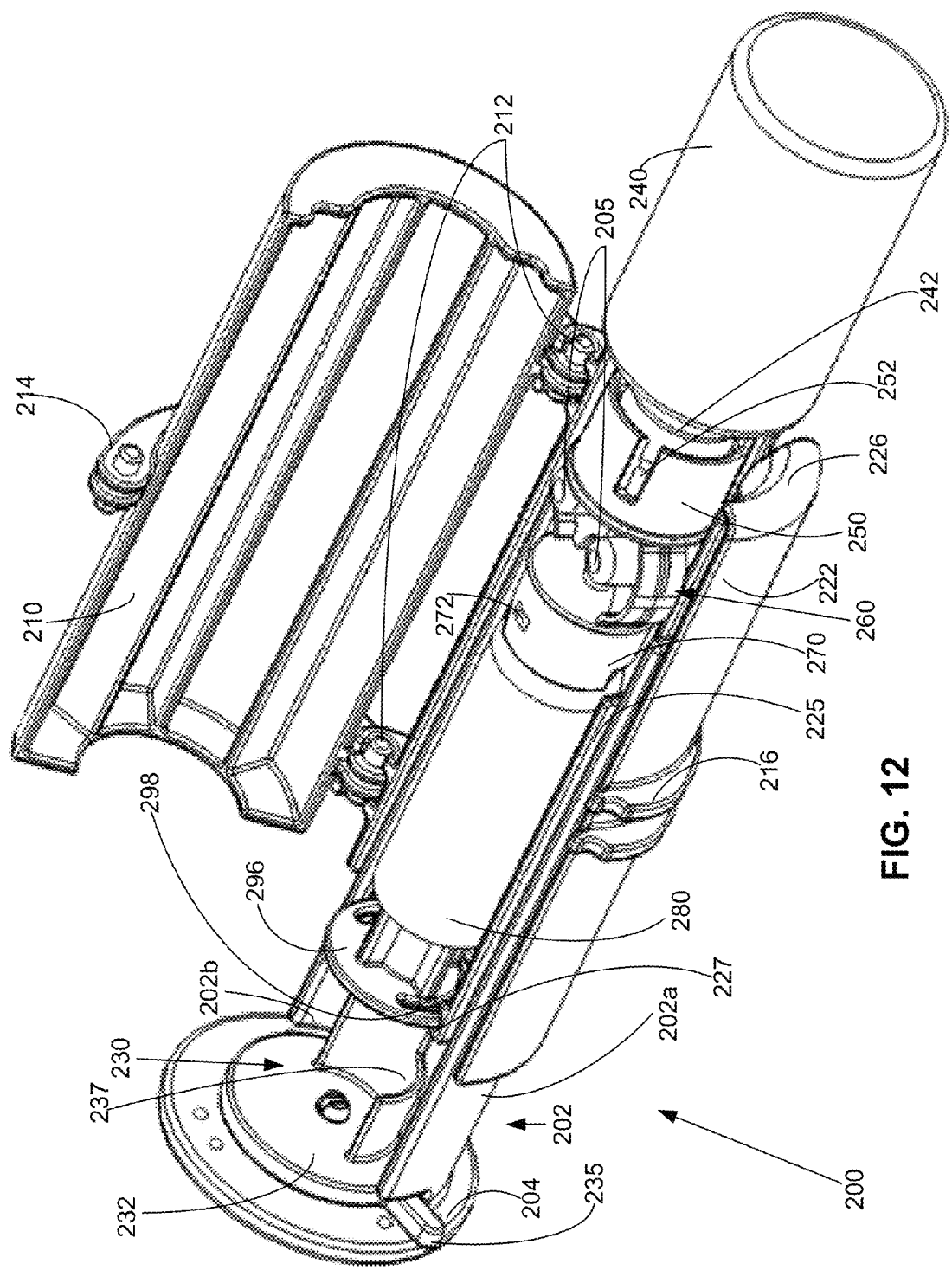
FIG. 12 illustrates a system for transferring fluidic media in accordance with an embodiment of the present invention.
Figure 13:
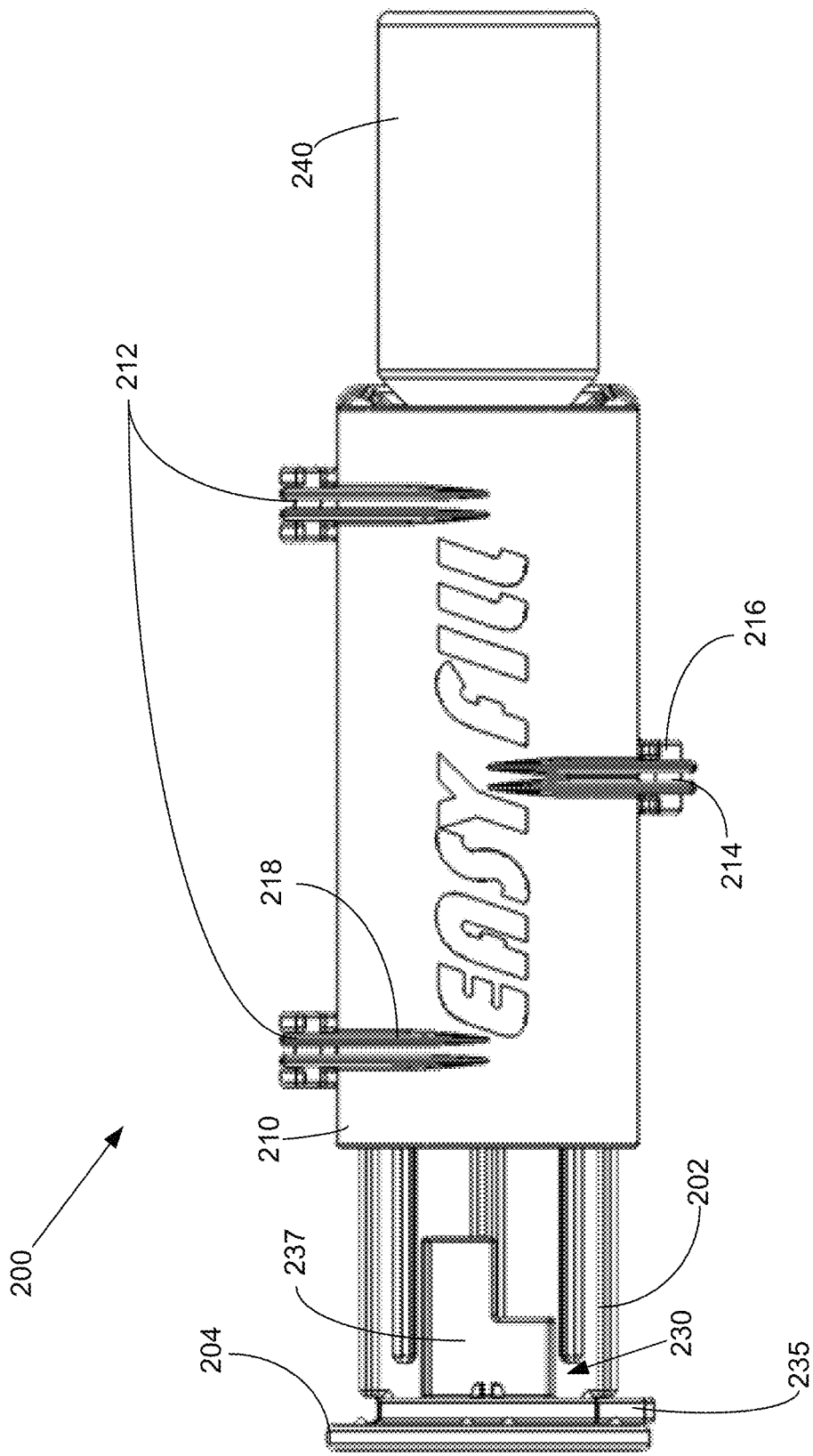
FIG. 13 illustrates a system for transferring fluidic media in accordance with an embodiment of the present invention.
Figure 14:
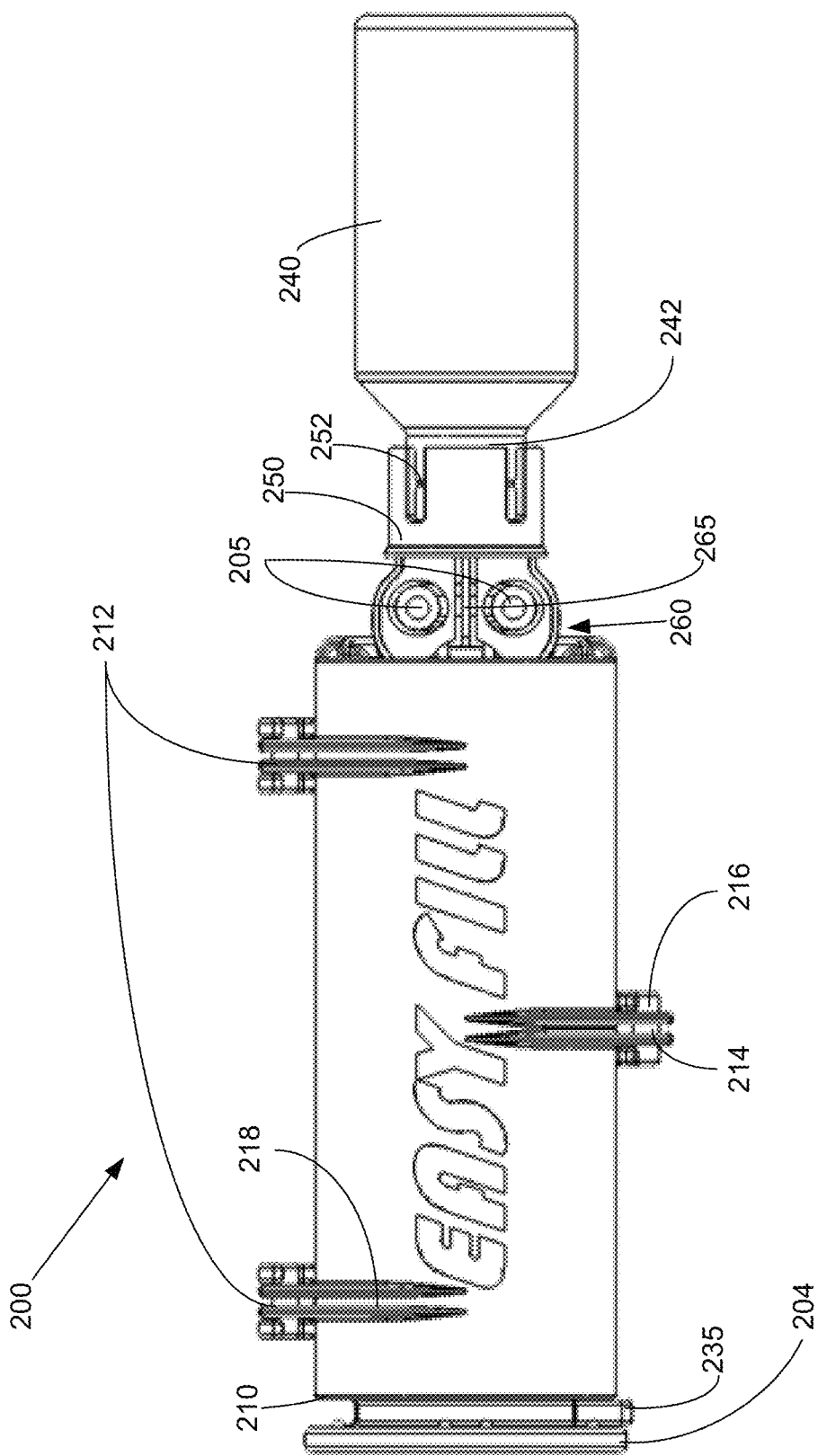
FIG. 14 illustrates a system for transferring fluidic media in accordance with an embodiment of the present invention.
Figure 15:
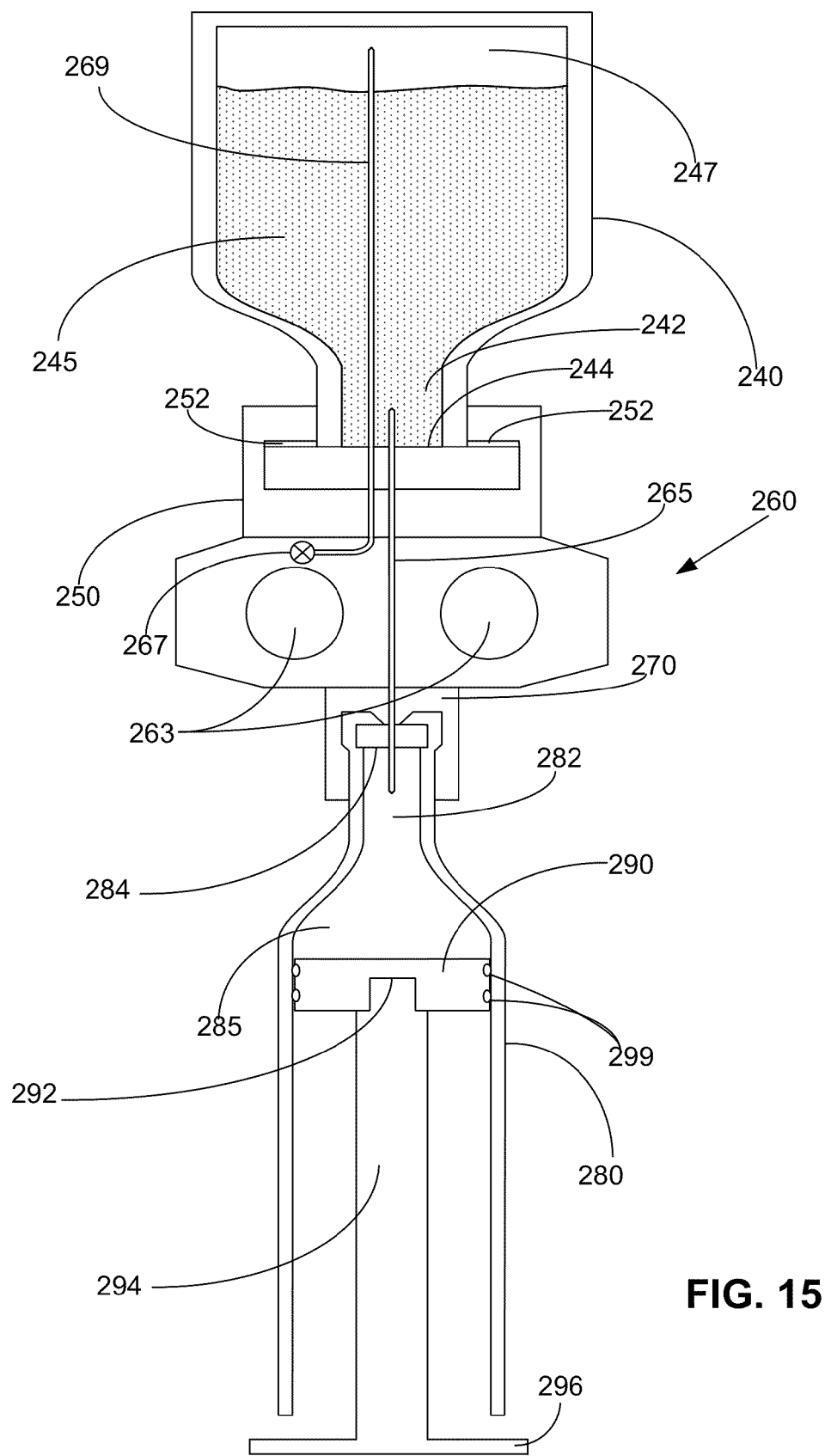
FIG. 15 illustrates a cross-sectional view of a transfer guard, a vial, and a reservoir for use with a system for transferring fluidic media in accordance with an embodiment of the present invention.
Figure 16:
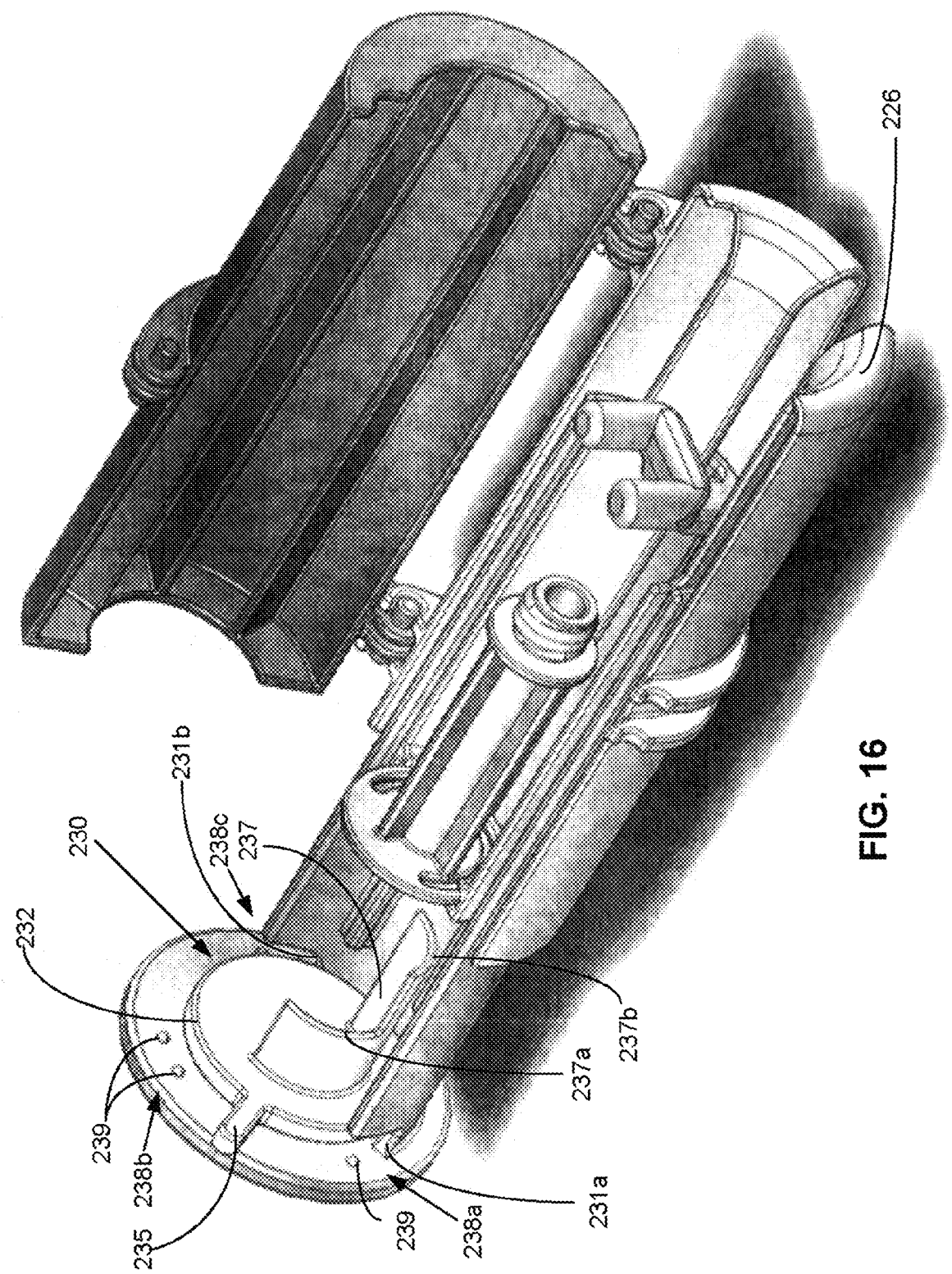
FIG. 16 illustrates a system for transferring fluidic media in accordance with an embodiment of the present invention.
Figure 17:
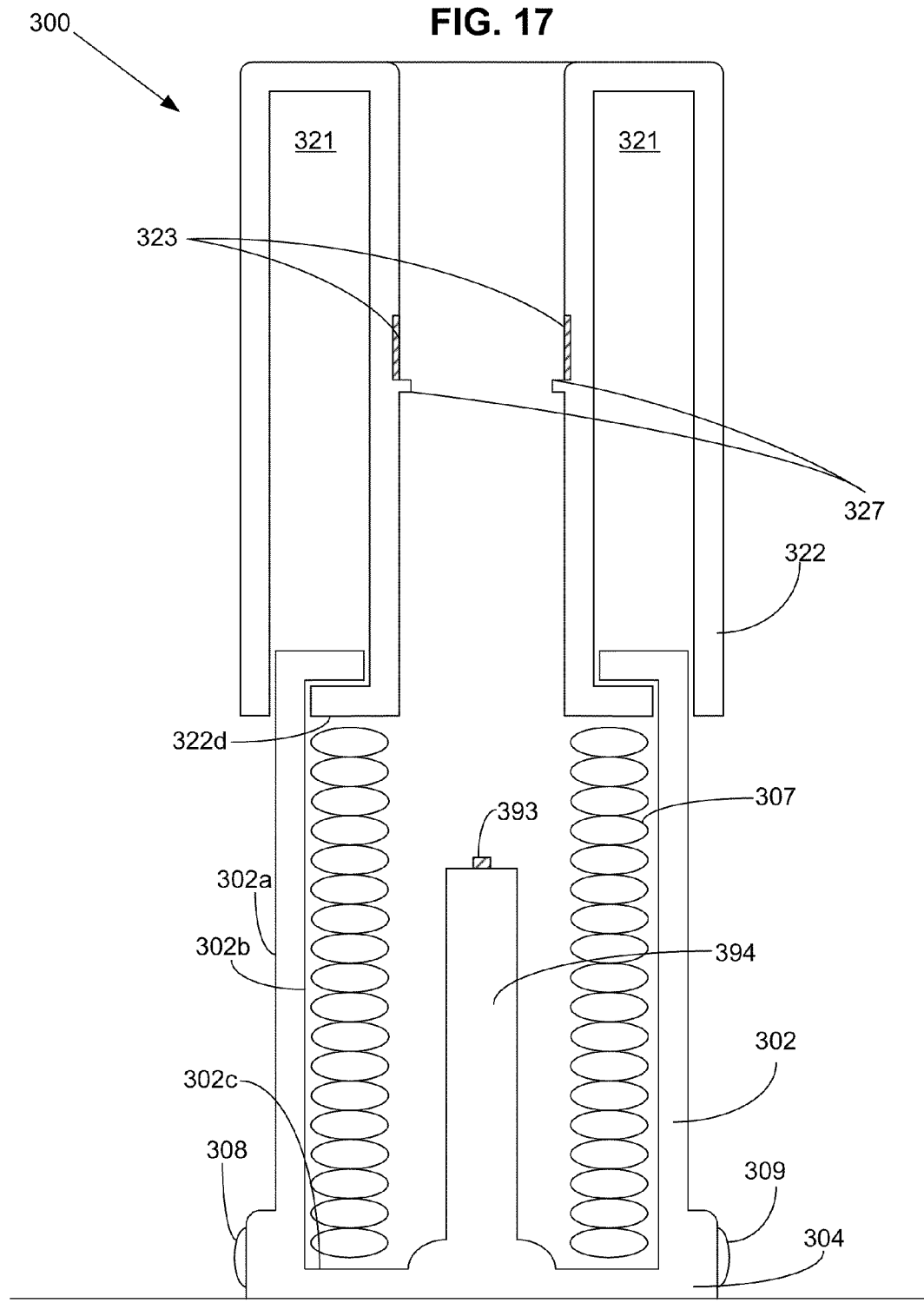
FIG. 17 illustrates a cross-sectional view of a system for transferring fluidic media in accordance with an embodiment of the present invention.
Figure 18:
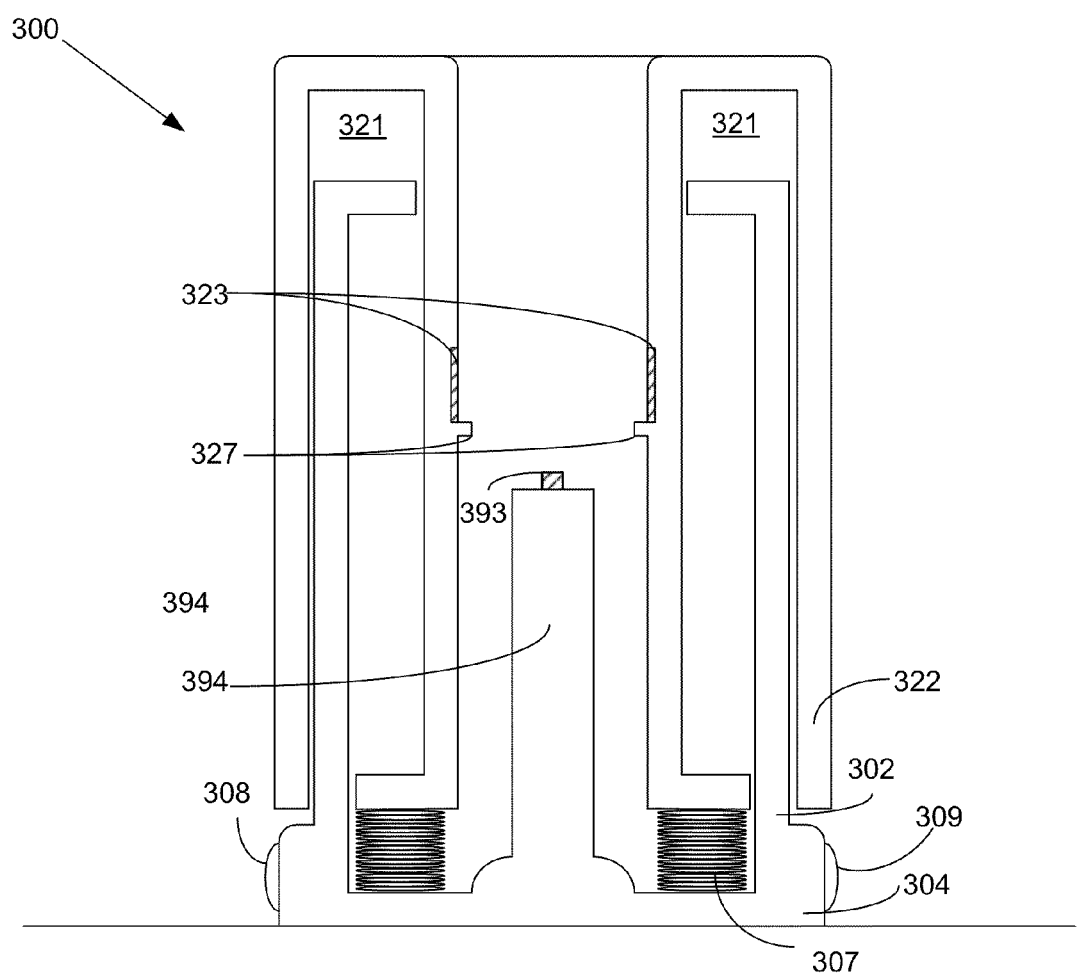
FIG. 18 illustrates a cross-sectional view of a system for transferring fluidic media in accordance with an embodiment of the present invention.
Figure 19:
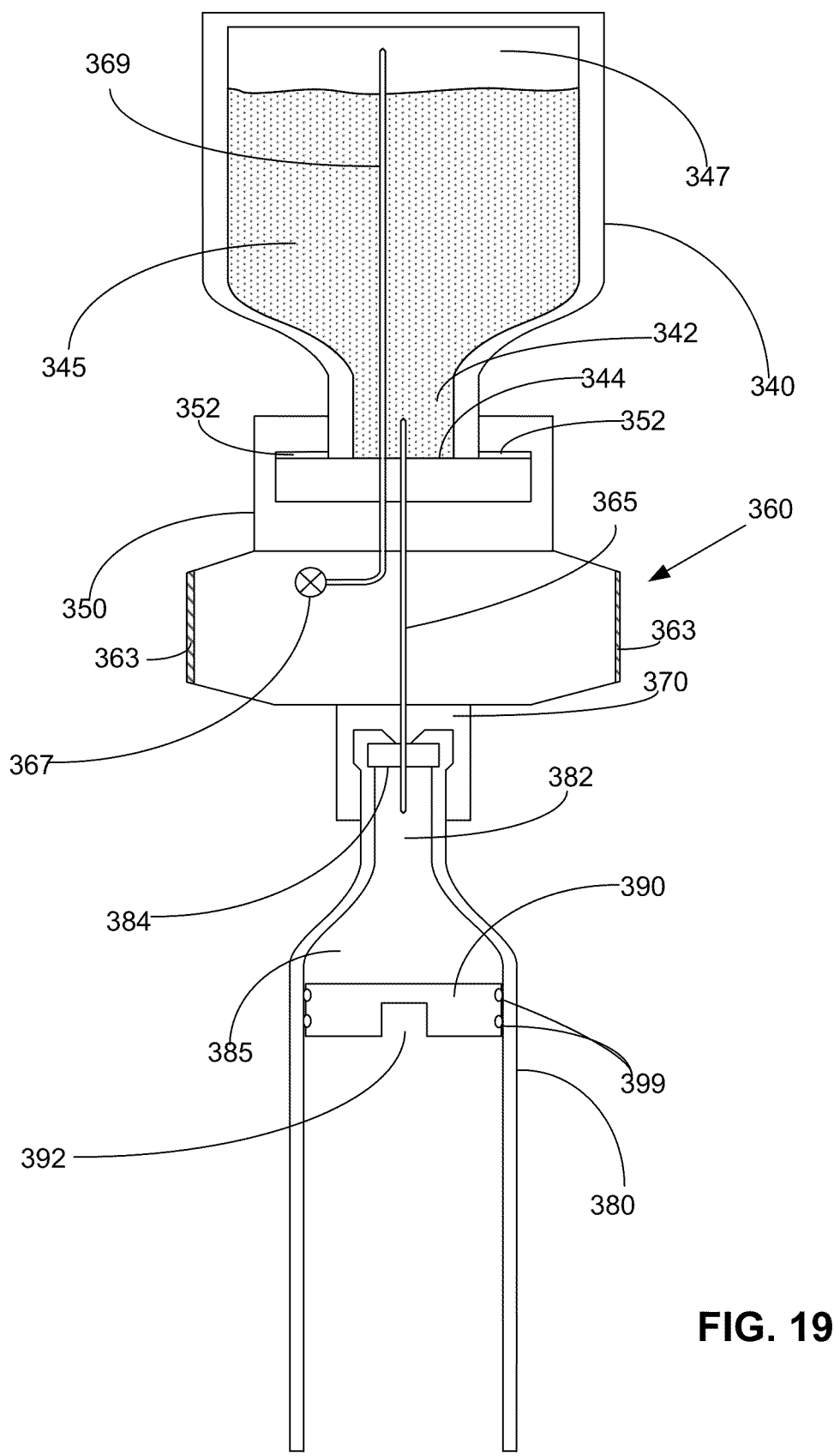
FIG. 19 illustrates a cross-sectional view of a transfer guard, a vial, and a reservoir for use with a system for transferring fluidic media in accordance with an embodiment of the present invention.
Figure 20:
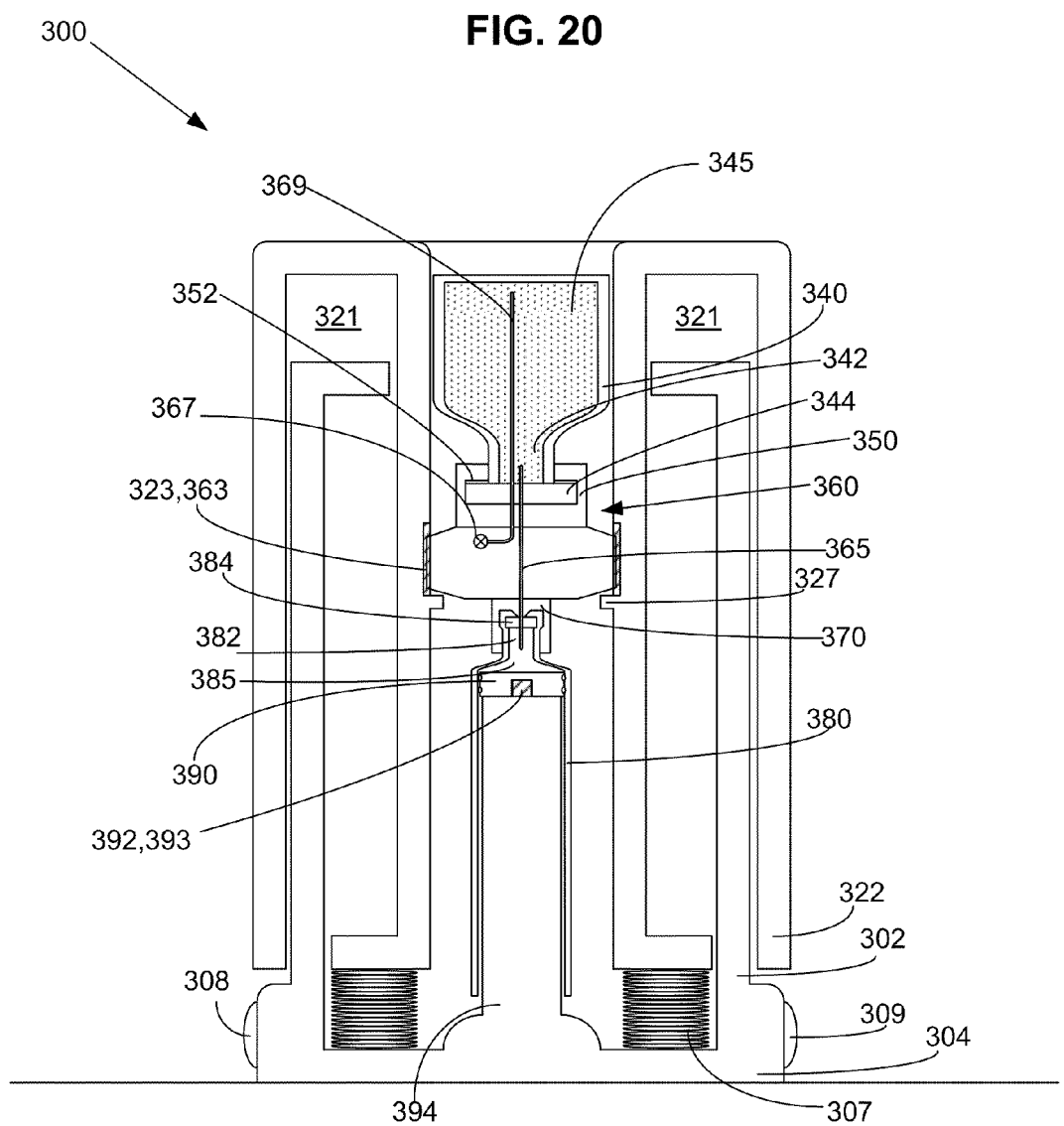
FIG. 20 illustrates a cross-sectional view of a system for transferring fluidic media in accordance with an embodiment of the present invention.
Figure 21:
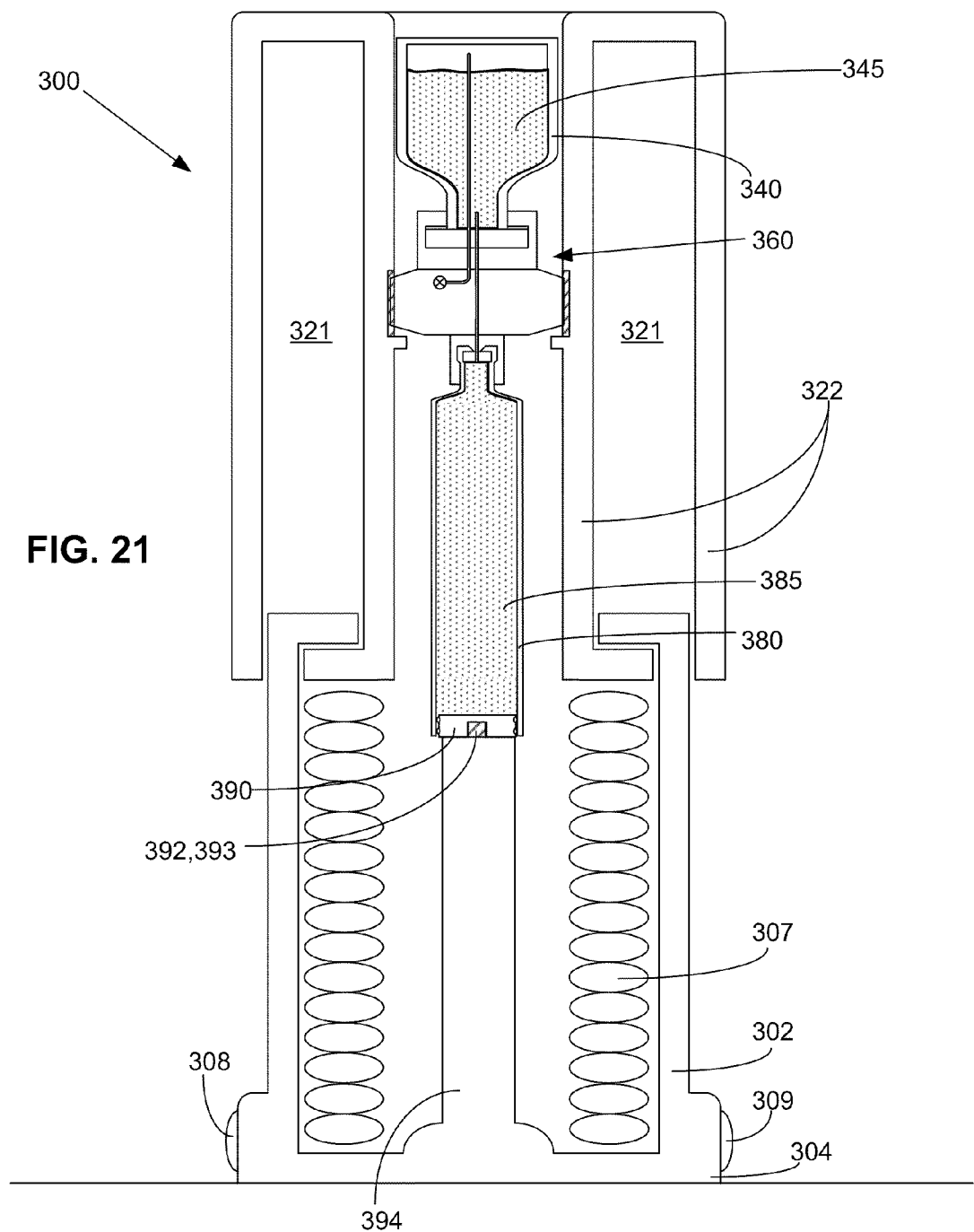
FIG. 21 illustrates a cross-sectional view of a system for transferring fluidic media in accordance with an embodiment of the present invention.

In some embodiments, the second housing portion 222 may be connected to a door 210. For example, the door 210 may be pivotally connected to the second housing portion 222 with a hinge 212. The door 210 may be held closed against the second housing portion 222 with a clasp 216. The system 200 may initially have the door 210 closed. The door 210 may be opened by the user. Once the door 210 is open, the transfer guard 260 along with the vial 240 and the reservoir 280 may be connected to the first housing portion 202 by way of the mating piece 205 as shown in FIGS. 11-12, and/or as described above. The handle 296 may be fitted into the recess 227 of the second housing portion 222 when the transfer guard 260 along with the vial 240 and the reservoir 280 are connected to the first housing portion 202. Thereafter, the door 210 may be closed so that the user can use the system 200, as shown in FIG. 13.

Referring back to FIGS. 11-16, the system 200 may allow for simplifying a filling process of the reservoir 280 with fluidic media from the vial 240. The user may push the second housing portion 222 against the first housing portion 202. For example, the user may grip the second housing portion 222 and door 210 and advance the second housing portion 222 and the door 210 along the first housing portion 202 toward the base 204. This may cause the portion 225 of the second housing portion 222 and the recess 227 therein to slide or otherwise move further along the first housing portion 202 toward the base 204 of the first housing portion 202. As a result, the handle 296 fitted within or otherwise connected to the recess 227 may be pulled away from the reservoir 280. As the plunger arm end 296 moves away from the reservoir 280, the attached plunger arm 294 and plunger head 290 may be moved within the reservoir 280 to increase the interior volume 285 of the reservoir 280. Movement of the plunger head 290 may draw fluidic media within the vial 240 through the transfer guard 260, for example through the needle 265, to the interior volume 285 of the reservoir 280, thus filling the interior volume 285 of the reservoir 280. In some embodiments, the plunger head 290 may be substantially advanced within the reservoir 280 toward the port 282 of the reservoir 280 before starting the filling process of the reservoir 280.

The system 200 may be used to fill the interior volume 285 of the reservoir 280, or a portion thereof. The system 200 may be configured such that the interior volume 285 of the reservoir 280 is completely filled or sufficiently filled when the second housing portion 222 is pushed completely into the first housing portion 202.

Once the user has finished using the system 200 during the filling process, for example once the interior volume 285 of the reservoir 280 is sufficiently filled, the doors 210 may be opened to remove the transfer guard 260 along with the reservoir 280 and vial 240. Alternatively, the user may remove one or more of those components, such as only the reservoir 280, while leaving the other components in the system 200 for future use.

In some embodiments, the system 200 may include textured areas 218 or the like on one or more of the second housing portion 222 and the door 210. The textured areas 218 may allow for increased handling or gripping of the system 200. The textured areas 218 may be, for example, a series of annular ribs surround the system 200 or a portion thereof as exemplified in FIGS. 13 and 14.

With reference to FIGS. 11-14 and 16, in various embodiments, the system 200 may include a fill volume control 230, an example of which is illustrated in FIGS. 11-14 and 16. The fill volume control 230 may be for allowing the user to select an amount of fluidic media to be transferred from the vial 240 to the reservoir 280 during the filling process. The fill volume control 230 may be configured for providing the user with a plurality of fixed positions that may be selectable by the user. The fill volume control 230 may be further configured such that each of the plurality of fixed positions may correspond to a fixed volume of fluidic media to be transferred from the vial 240 to the reservoir 280 during the filling process.

In various embodiments, the fill volume control 230 may include a base 232, a fill volume control handle 235, and a stop 237. The base 232 of the fill volume control 230 may be at least partially rotatable about the first housing portion 202. In some embodiments, the base 232 of the fill volume control 230 may be connected to the base 204 of the first housing portion 202. In such embodiments, the base 232 of the fill volume control 230 may be at least partially rotatable about the base 204 of the first housing portion 202. The base 232 of the fill volume control 230 may be rotatable to a plurality of fixed positions, which may correspond to a fixed volume of fluidic media to be transferred from the vial 240 to the reservoir 280 during the filling process.

The fill volume control handle 235 may be connected to the base 232 of the fill volume control 230 such that the base 232 of the fill volume control 230 can be rotated when the fill volume control handle 235 is moved. The fill volume control handle 235 may be configured to move between a plurality of fixed positions to rotate the base 232 of the fill volume control 230 to one of the plurality of fixed positions to select a corresponding volume of fluidic media to be transferred from the vial 240 to the reservoir 280 during the filling process.

The stop 237 may be attached to the base 232 of the fill volume control 230. The stop 237 may extend away from the base 232 of the fill volume control 230 toward the top surface 226 of the second housing portion 222. The stop 237 may be configured such that the distance between the stop 237 and the reservoir 280 corresponds to a volume of fluidic media to be transferred from the vial 240 to the reservoir 280 during the filling process. The stop 237 may be for preventing the second housing portion 222 from advancing toward the base 204 of the first housing portion 202 beyond a point where the stop 237 contacts the bottom of the handle 296. Accordingly, the plunger head 290 and the handle 296 may be moveable within the reservoir 280 until the stop 237 contacts the bottom of the handle 296. Therefore, fluidic media may be transferred from the vial 240 to the reservoir 280 until the stop 237 prevents further movement of the handle 296 and the plunger head 290.

In various embodiments, the stop 237 may have one or more stop surfaces, such as a first stop surface 237a, located on an end of the stop 237 extending away from the base 232 of the fill volume control 230. The stop 237 may be configured such that the distance between the first stop surface 237a and the reservoir 280 corresponds to a first volume of fluidic media to be transferred from the vial 240 to the reservoir 280. The first stop surface 237a may be for preventing the second housing portion 222 from advancing toward the base 204 of the first housing portion 202 beyond a point where the first stop surface 237a contacts the bottom of the handle 296. Accordingly, the plunger head 290 and the handle 296 may be moveable within the reservoir 280 until the first stop surface 237a contacts the bottom of the handle 296. Therefore, fluidic media may be transferred from the vial 240 to the reservoir 280 until the first stop surface 237a prevents further movement of the handle 296 and the plunger head 290.

In various embodiments, the stop 237 may include a second stop surface 237b. The stop 237 may be configured such that the second stop surface 237b may be located on an end of the stop 237 further from the base 232 of the fill volume control 230 than the first stop surface 237a. The stop 237 may be further configured such that the distance between the second stop surface 237b and the reservoir 280 corresponds to a second volume of fluidic media to be transferred from the vial 240 to the reservoir 280. The second stop surface 237b may be for preventing the second housing portion 222 from advancing toward the base 204 of the first housing portion 202 beyond a point where the second stop surface 237b contacts the bottom of the handle 296. Accordingly, the plunger head 290 and the handle 296 may be moveable within the reservoir 280 until the second stop surface 237b contacts the bottom of the handle 296. Therefore, fluidic media may be transferred from the vial 240 to the reservoir 280 until the second stop surface 237b prevents further movement of the handle 296 and the plunger head 290.

In various embodiments, the stop 237 may further include additional stop surfaces, such as a third stop surface (not shown), a fourth stop surface (not shown), and so on. The stop 237 may be configured such that each of the additional stop surfaces may be located on an end of the stop 237 further from the base 232 of the fill volume control 230 than the previous stop surface. The stop 237 may be further configured such that the distance between the additional stop surfaces and the reservoir 280 corresponds to volumes of fluidic media to be transferred from the vial 240 to the reservoir 280 during the filling process. For example, in a case where a stop 237 has four stop surfaces, the third stop surface (not shown) may be located further from the base 232 of the fill volume control 230 than the second stop surface 237b. Meanwhile, the fourth stop surface (not shown) may be located further from the base 232 of the fill volume control 230 than the third stop surface (not shown).

One of the additional stop surfaces may be for preventing the second housing portion 222 from advancing toward the base 204 of the first housing portion 202 beyond a point where the one of the additional stop surfaces contacts the bottom of the handle 296. Accordingly, the plunger head 290 and the handle 296 may be moveable within the reservoir 280 until the one of the additional stop surfaces contact the bottom of the handle 296. Therefore, fluidic media may be transferred from the vial 240 to the reservoir 280 until the one of the additional stop surfaces prevent further movement of the handle 296 and the plunger head 290. For example, in a case where a stop 237 has four stop surfaces, the third stop surface (not shown) may prevent the second housing portion 222 from advancing toward the base 204 of the first housing portion 202 beyond the third stop surface (not shown) in a case where the third stop surface (not shown) contacts the bottom of the handle 296.

In some embodiments, the fill volume control 230 may include a plurality of stops 237. Each of the plurality of stops 237 may be of varying lengths, such that each of the plurality of stops 237 extends varying lengths away from the base 232 of the fill volume control 230. Each of the plurality of stops 237 may be configured such that the distance between each of the plurality of stops 237 and the reservoir 280 corresponds to volumes of fluidic media to be transferred from the vial 240 to the reservoir 280 during the filling process.

One of the plurality of stops 237 may be for preventing the second housing portion 222 from advancing toward the base 204 of the first housing portion 202 beyond a point where the one of the plurality of stops 237 contacts the bottom of the handle 296. Accordingly, the plunger head 290 and the handle 296 may be moveable within the reservoir 280 until the one of the plurality of stops 237 contacts the bottom of the handle 296. Therefore, fluidic media may be transferred from the vial 240 to the reservoir 280 until the one of the plurality of stops 237 prevents further movement of the handle 296 and the plunger head 290.

In some embodiments, the stop 237 of the fill volume control 230 may have an angled surface (not shown) angled relative to the base 232 of the fill volume control 230, for example angled at a 45° angle. The angled surface (not shown) of the stop 237 may extend away from the base 232 of the fill volume control 230. The distances between various locations on the angled surface (not shown) of the stop 237 may be configured such that the distance between each of the various locations and the reservoir 280 corresponds to volumes of fluidic media to be transferred from the vial 240 to the reservoir 280 during the filling process.

One of the various locations on the angled surface (not shown) of the stop 237 may be for preventing the second housing portion 222 from advancing toward the base 204 of the first housing portion 202 beyond a point where the one of the various locations on the angled surface (not shown) of the stop 237 contacts the bottom of the handle 296. Accordingly, the plunger head 290 and the handle 296 may be moveable within the reservoir 280 until the one of the various locations on the angled surface (not shown) of the stop 237 contacts the bottom of the handle 296. Therefore, fluidic media may be transferred from the vial 240 to the reservoir 280 until the one of the various locations on the angled surface (not shown) of the stop 237 prevents further movement of the handle 296 and the plunger head 290.

In some embodiments, the handle 296 connected to the plunger arm 294 may include an aperture 298. The stop 237 may be configured to be insertable into the aperture 298 in a case where the stop 237 and the aperture 298 are aligned prior to the filling process and the handle 296 is advanced beyond at least a portion of the stop 237 during the filling process. While the stop 237 is aligned with the aperture 298, the stop 237 may slide or otherwise fit into the aperture 298 to allow the handle 296 to advance toward the base 204 of the first housing portion 202 during the filling process.

In some embodiments, the stop 237 may be configured such that stop surfaces (e.g., 237a, 237b) aligned with the aperture 298 prior to the filling process may be insertable in the aperture 298 during the filling process. Each of the stop surfaces aligned with the aperture 298 prior to the filling process may slide or otherwise fit into the aperture 298 and allow the second housing portion 222, which is supporting the handle 296, to advance toward the base 204 of the first housing portion 202 during the filling process. Because the aperture 298 is located on the handle 296, the handle 296 may slide along the stop 237 and the stop surfaces that were aligned with the aperture 298 prior to the filling process as the handle 296 is moved toward the base 204.

The plunger head 290 and the handle 296 may be moved to a final position where either at least one of the stop surfaces not aligned with the aperture 298 prior to the filling process contacts the handle 296 or the base 232 of the fill volume control 230 (i.e., the second housing portion 222 is advanced completely towards the base 232 of the fill volume control 230). Accordingly, the second housing portion 222 may be moveable to the final position. Therefore, fluidic media may be transferred from the vial 240 to the reservoir 280 until the at least one of the stop surfaces not aligned with the aperture 298 prior to the filling process or the base 232 of the fill volume control 230 prevents further movement of the handle 296 and the plunger head 290.

For example, according to an embodiment exemplified in FIGS. 11-14 and 16, the fill volume control handle 235 may have three selectable positions, such as a first position 238a, a second position 238b, and a third position 238c, corresponding to three fixed volumes of fluidic media, such as 3 ml, 2 ml, and 1 ml, respectively, selectable by the user to be transferred from the vial 240 to the reservoir 280 during the filling process. The stop 237 may be further configured such that the distance between the stop surfaces 237a, 237b and the reservoir 280 also corresponds to the volumes of fluidic media to be transferred from the vial 240 to the reservoir 280 during the filling process, such as 2 ml and 1 ml, respectively. While the distance between the base 232 of the fill volume control 230 and the reservoir 280 may correspond to 3 ml.

Therefore, if the reservoir 280 is to be filled with 1 ml of fluidic media, the fill volume control handle 235 may be moved to the third position 238c. In the third position 238c, the first stop surface 237a and the second stop surface 237b are not aligned with the aperture 298 of the handle 296 prior to the filling process. Thus during the filling process, the handle 296 and the plunger head 290 are only advanceable until the handle 296 contacts the second stop surface 237b. Accordingly, because the stop 237 may be configured such that the distance between the second stop surface 237b and the reservoir 280 corresponds to 1 ml, 1 ml of fluidic media may be transferred from the vial 240 to the reservoir 280 during the filling process.

Continuing with the previous example, if the reservoir 280 is to be filled with 2 ml of fluidic media, the fill volume control handle 235 may be moved to the second position 238b. In the second position 238b, the second stop surface 237b is aligned with the aperture 298 of the handle 296 prior to the filling process, while the first stop surface 237a is not aligned with the aperture 298 of the handle 296. Thus during the filling process, the handle 296 and the plunger head 290 are advanceable past the second stop surface 237b to a point where the handle 296 contacts the first stop surface 237a. Accordingly, because the stop 237 is configured such that the distance between the first stop surface 237a and the reservoir 280 corresponds to 2 ml, 2 ml of fluidic media may be transferred from the vial 240 to the reservoir 280 during the filling process.

Again continuing with the previous example, if the reservoir 280 is to be filled with 3 ml of fluidic media, the fill volume control handle 235 may be moved to the first position 238a. In the first position 238a, the first stop surface 237a and the second stop surface 237b are aligned with the aperture 298 of the handle 296 prior to the filling process. Thus during the filling process, the handle 296 and the plunger head 290 are advanceable past the first stop surface 237a and the second stop surface 237b to a point where the handle 296 contacts the base 232 of the fill volume control 230. Accordingly, because the fill volume control 230 may be configured such that the distance between the base 232 of the fill volume control 230 and the reservoir 280 corresponds to 3 ml, 3 ml of fluidic media may be transferred from the vial 240 to the reservoir 280 during the filling process.

In some embodiments, the fill volume control 230 may further include abutments 231a, 231b to prevent the fill volume control handle 235 from moving beyond the abutments 231a, 231b. Accordingly, the abutments 231a, 231b may allow for restricting the rotation of the base 232 of the fill volume control 230 about the first housing portion 202. The abutments 231a, 231b may be part of the first housing portion 202. Using the previous example, the abutments 231a, 231b may prevent the rotation of the fill volume control handle 235 of the fill volume control 230 beyond the first position 238a and the third position 238c, respectively.

In some embodiments, the fill volume control 230 may further include protrusions 239 located in front and/or behind of each of the plurality of selectable positions of the fill volume control handle 235. The protrusions 239 may be located on the base 204 of the first housing portion 202 or the base 232 of the fill volume control 230. The protrusions 239 may be for inhibiting accidental movement of the fill volume control handle 235 beyond each set of the protrusions 239. The fill volume control handle 235 may be moveable beyond each set of the protrusions 239 when a sufficient force is applied to the fill volume control handle 235. In some embodiments, the set of protrusions may serve to designate each of the plurality of selectable positions for the fill volume control handle 235.

FIGS. 17-21 illustrate a system 300 for transferring fluidic media and a portion thereof in accordance with an embodiment of the present invention. The system 300 may include, but is not limited to, a first housing portion 302, a second housing portion 322, a vial 340, a reservoir 380, a plunger head 390, a plunger arm 394, and a transfer guard 360. The first housing portion 302 and the second housing portion 322 may be configured such that the second housing portion 322 is moveable relative to a latitudinal dimension of the first housing portion 302. For example, the first housing portion 302 and the second housing portion 322 may be slideably connected such that the second housing portion 322 may slide over the first housing portion 302 when a user pushes the second housing portion 322 into the first housing portion 302.

The second housing portion 322 may be disposed around the first housing portion 302 to envelop a portion of an outer surface 302a and a portion of an inner surface 302b of the first housing portion 302. An end of the plunger arm 394 may be connected to the first housing portion 302. Another end of the plunger arm 394 opposite from the end connected to the first housing portion 302 may have a portion 393 for connecting with the plunger head 390. The system 300 may include a base 304 located on a bottom end of the bottom portion 302 for standing the system 300 vertically on a suitable surface, such as a table top, countertop, or the like. In some embodiments, the base 304 may have an adhesive bottom (not shown) for attaching the system 300 to the suitable surface. In some embodiments, the base 304 may include a friction pad (not shown), which may be made of rubber, or the like located on the bottom surface of the base 304 to prevent the system 300 from slipping during usage of the system 300.

The vial 340 may include a septum 344 located at a port 342 of the vial 340, and the vial 340 may be for containing fluidic media. The reservoir 380 may have an interior volume 385 for containing fluidic media. The plunger head 390 may be located within the reservoir 380 and may be moveable within the reservoir 380 to expand or contract the interior volume 385 of the reservoir 380. The plunger head 390 may be connectable to the plunger arm 394. The reservoir 380 may include a septum 384 located at a port 382 of the reservoir 380. The plunger head 390 may include at least one seal member 399, such as an o-ring, or the like to facilitate movement within the interior volume 385 of the reservoir 380 and/or to substantially prevent fluidic media from flowing between the plunger head 390 and the reservoir 380.

The transfer guard 360 may include a needle 365 for providing a fluid path from the interior volume 345 of the vial 340 to the interior volume 385 of the reservoir 380. The transfer guard 360 may be configured such that when the vial 340 is attached to the transfer guard 360, the needle 365 pierces the septum 344 of the vial 340. The transfer guard 360 may be further configured such that when the reservoir 380 is attached to the transfer guard 360, the needle 365 pierces the septum 384 of the reservoir 380. Thus, the transfer guard 360 may allow for establishing the fluid path from the vial 340 to the reservoir 380 through the needle 365.

In some embodiments, the transfer guard 360 may include a second needle 369. The second needle 369 may be able to pierce the septum 344 of the vial 340 when the vial 340 is connected to the transfer guard 360. An end of the second needle 369 may be located within a headspace 347 of the vial 340 above fluidic media within the interior volume 345 of the vial 340 in a case where the transfer guard 360 is connected to the vial 340. In other embodiments, the end of the second needle 369 may be in contact with fluidic media within the interior volume 345 of the vial 340 in a case where the transfer guard 360 is connected to the vial 340. Another end of the second needle 369 may be connected to a check valve 367, such as a one-way valve, or the like. The check valve 367 may allow air to enter the interior volume 345 of the vial 340 through the second needle 369. In some embodiments, the check valve 367 may substantially prevent liquid from coming out of the vial 340 through the second needle 369 and/or the check valve 367. In various embodiments, the second needle 369 may allow for venting the headspace 347 or the interior volume 345 of the vial 340 to atmosphere to facilitate the transfer of fluidic media from the vial 140 to the reservoir 180.

The transfer guard 360 may have a first end 350 for supporting the vial 340. The port 342 of the vial 340 may be insertable into the first end 350 of the transfer guard 360. As mentioned, the septum 344 of the vial 340 may be pierced by the needle 365 of the transfer guard 360 when the vial 340 is inserted into the first end 350 of the transfer guard 360. The first end 350 of the transfer guard 360 may include a tab 352 for securing the vial 340 within the first end 350 of the transfer guard 360 once the vial 340 is inserted in the first end 350 of the transfer guard 360. The first end 350 of the transfer guard 360 may be configured to include multiple tabs 352 or one or more annular ribs for example, to secure the vial 340 within the first end 350 of the transfer guard 360.

The transfer guard 360 may have a second end 370 for supporting the reservoir 380. The port 382 of the reservoir 380 may be insertable into the second end 370 of the transfer guard 360. The septum 384 of the reservoir 380 may be pierced by the needle 365 of the transfer guard 360 when the reservoir 380 is inserted into the second end 370 of the transfer guard 360.

In some embodiments, the second end 370 of the transfer guard 360 may include depressions or apertures (such as 176 in FIG. 28) located within the second end 370 of the transfer guard 360. The port 382 of the reservoir 380 may include one or more tabs (such as 186 in FIG. 29) for inserting into the apertures (176 in FIG. 28) located in the second end 370 of the transfer guard 360. The port 382 of the reservoir 380 may further include a second tab (such as 188 in FIG. 29) attached to each of the tabs (186 in FIG. 29). The reservoir 380 and port 382 may be configured to be rotatable, at least partially, about the second end 370 of the transfer guard 360. The second end 370 of the transfer guard 360 may further include one or more depressions (such as 178 in FIG. 28) for receiving the second tabs (188 in FIG. 29) when the reservoir 380 and port 382 are rotated to secure the reservoir 380 to the transfer guard 360. As a result, the port 382 of the reservoir 380 may be inserted into the second end 370 of the transfer guard 360 so that the tabs (186 in FIG. 29) fit into the apertures (176 in FIG. 28) and then rotated slightly until the second tabs (188 in FIG. 29) fit into place within the depressions (178 in FIG. 28) to lock the reservoir 280 into the second end 270 of the transfer guard 260.

In some embodiments, the first end 350 of the transfer guard 360 and the vial 340 may be configured in the same manner as described above so that the tabs (186 in FIG. 29) fit into the apertures (176 in FIG. 28) and then rotates slightly until the second tabs (188 in FIG. 29) fit into place within the depressions (178 in FIG. 28). In some embodiments, the second end 370 of the transfer guard 360 may be configured to include a tab 352 for securing the reservoir 380 within the second end 370 of the transfer guard 360 similar to what was described above with respect to the first end 350 of the transfer guard 360.

Once the vial 340 and the reservoir 380 have been inserted in the first end 350 and the second end 370 of the transfer guard 360 respectively, the transfer guard 360 may be ready to be installed to the first housing portion 302. In some embodiments, the transfer guard 360 may have threaded sides 363. The second housing portion 322 may have a threaded area 323 for engaging the threaded sides 363 of the transfer guard 360 when, for example, the transfer guard 360 is rotated into place to connect the transfer guard 360 to the second housing portion 322. In some embodiments, the plunger arm 394 may have a threaded tip 393. The plunger head 390 may have a threaded recess 392 or portion for engaging the threaded tip 393 when, for example, the reservoir 380 is rotated into place to connect the plunger head 390 to the plunger arm 394. The threaded side 363 of the transfer guard 360 and the threaded area 323 of the second housing portion 322 may be engaged approximately at the same time that the threaded tip 393 of the plunger arm 394 and the threaded recess 392 of the plunger head 390 are being engaged. As a result, only the transfer guard 360 may have to be rotated by the user to engage the threaded side 363 of the transfer guard 360 to the threaded area 323 of the second housing portion 322 and the threaded tip 393 of the plunger arm 394 to the threaded recess 392 of the plunger head 390. Alternatively, the system 300 may be configured such that the reservoir 380 or the vial 340 could be rotated by the user instead of the transfer guard 360 to secure the transfer guard 360 to the second housing portion 322.

In some embodiments, the second housing portion 322 may be connected to a door (not shown). For example, the door may be pivotally connected to the second housing portion 322 with a hinge (not shown). The door (not shown) may be held closed against the second housing portion 322 with a clasp (not shown). The system 300 may initially have the door (not shown) closed. The door (not shown) may be opened by the user. Once the door (not shown) is open, the transfer guard 360 along with the vial 340 and the reservoir 380 may be connected to the first housing portion 302 as described above. Thereafter, the door (not shown) may be closed so that the user can use the system 300.

The system 300 may allow for automating a filling process of the reservoir 380 with fluidic media from the vial 340. The system 300 may include a bias member, such as a spring 307, or the like. In some embodiments, the system 300 may further include a latch (not shown).

The spring 307 may be connected between a bottom surface 322d of the second housing portion 322 and a surface 302c of the first housing portion 302. The spring 307 may be initially biased toward an expanded position. The second housing portion 322 may be moveable along the latitudinal dimension of the first housing portion 302 between at least a first position and a second position. In the first position of the second housing portion 322, the spring 307 may be in the expanded position. In the second position of the second housing portion 322, the spring 307 may be held compressed by the second housing portion 322. The spring 307 and/or the second hosuing portion may be held in place by a latch (not shown).

The system 300 may allow for the transfer guard 360 along with the reservoir 380 and vial 340 to be connected to the second housing portion 322. In addition, the system 300 may allow for filling the reservoir 380 using a force applied by the spring 307 on the second housing portion 322 when the latch (not shown) is released to allow the spring to push up on the bottom surface 322d of the second housing portion 322. According to an embodiment of the present invention, the system 300, the first housing portion 302 may be connected to the plunger arm 394, the plunger arm 394 may be connected to the plunger head 390, and the transfer guard 360 and reservoir 380 may be supported by the second housing portion 322 such that movement of the second housing portion 322, and thus the reservoir 380, away from the first housing portion 302, and thus the plunger head 390, causes the reservoir 380 to move relative to the plunger head 390 to create a vacuum that enables a filling of the reservoir 380.

The latch (not shown) may be moveable between a locked position and an unlocked position. The latch (not shown) may be for holding the spring 307 compressed or for holding the second housing portion 322 against the spring 307 when in the locked position. In various embodiments, the system may include a button 308 for moving the latch (not shown) from the unlocked position to the locked position. The system may further include a second button 309 for moving the latch (not shown) from the locked position to the unlocked position. In other embodiments, the button 308 may be for moving the latch (not shown) from the locked position to the unlocked position as well.

For example, the user could push the second housing portion 322 into the first housing portion 302 (i.e., move the second housing portion 322 to the second position) and then press the button 308 to move the latch (not shown) to the locked position to keep the second housing portion 322 at the second position. The transfer guard 360 along with the reservoir 380 and the vial 340 may be connected to the second housing portion 322 as described above. Once installed, the second button 309 may be pressed to release the latch (not shown) allowing the spring 307 to expand and thus return the second housing portion 322 to the first position. In returning to the first position, fluidic media may be drawn into the interior volume 385 of the reservoir 380 from the interior volume 345 of the vial 340 as described above.

In various embodiments, a tension of the spring 307 may be selected so as to allow for the reservoir 380 to fill at different rates when the spring 307 expands depending on the tension of the spring 307. Thus, various embodiments of the present invention allow for spring loaded automatic filling of a reservoir, and for drawing a fluid or drug from an inverted vial into a reservoir.

The system 300 may be used to fill the interior volume 385 of the reservoir 380, or a portion thereof. The system 300 may be configured such that the interior volume 385 of the reservoir 380 is completely filled or sufficiently filled in a case where the spring 307 forces the second housing portion 322 substantially away from the first housing portion 302.

Once the user has finished using the system 300 during the filling process, for example once the interior volume 385 of the reservoir 380 is sufficiently filled, the door (not shown) may be opened to remove the transfer guard 360 along with the reservoir 380 and vial 340. Alternatively, the user may remove one or more of those components, such as only the reservoir 380, while leaving the other components in the system 300 for future use.

In some embodiments, the system 300 may include textured areas (such as 218 in FIGS. 13 and 14), or the like, on one or more of the second housing portion 322 and the door (not shown). The textured areas (218 in FIGS. 13 and 14) may allow for increased handling or gripping of the system 300. The textured areas (218 in FIGS. 13 and 14) may be, for example, a series of annular ribs that surround the system 300 or a portion thereof as exemplified in FIGS. 13 and 14.

Figure 22:
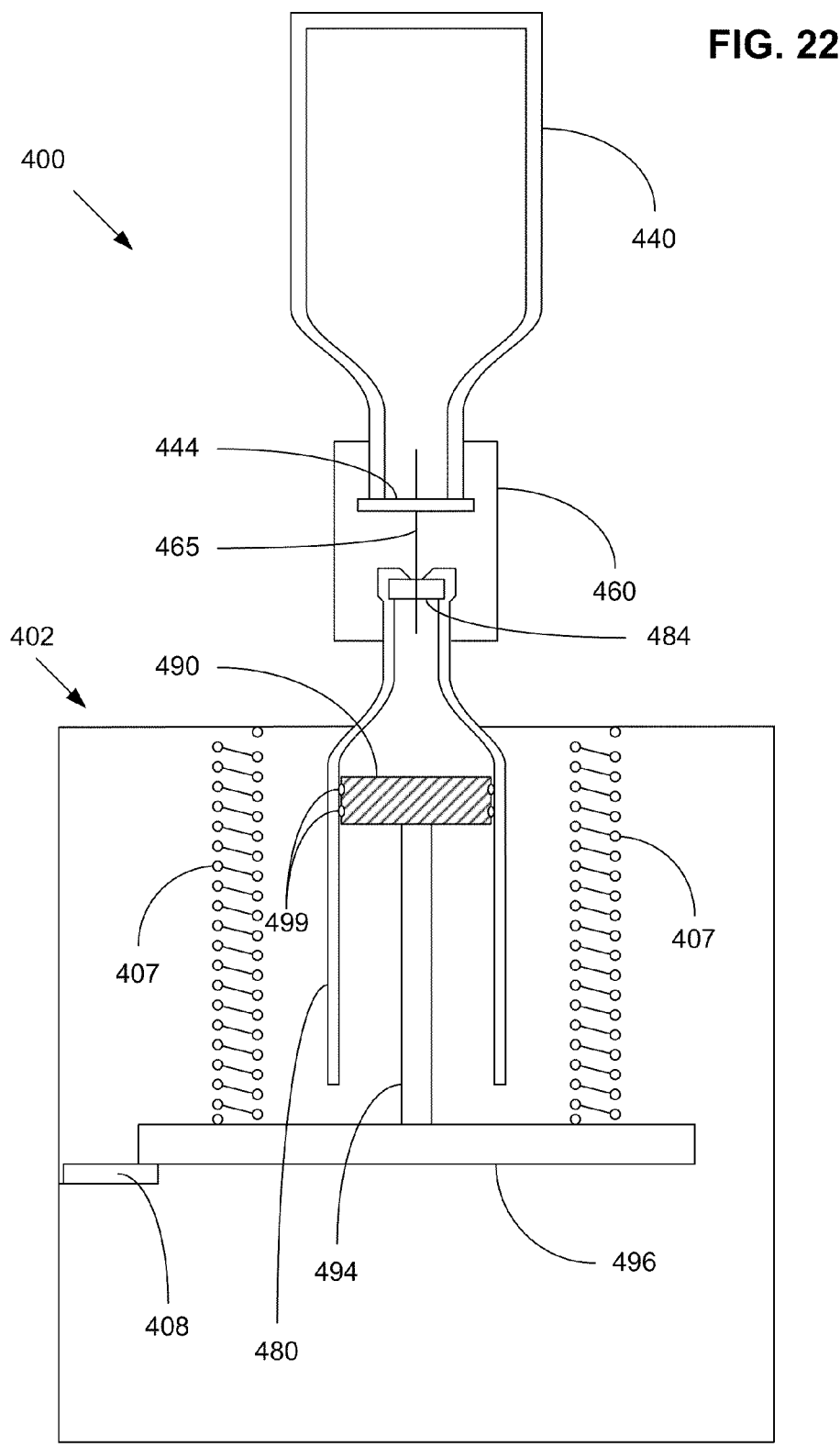
FIG. 22 illustrates a cross-sectional view of a system for transferring fluidic media in accordance with an embodiment of the present invention.
Figure 23:
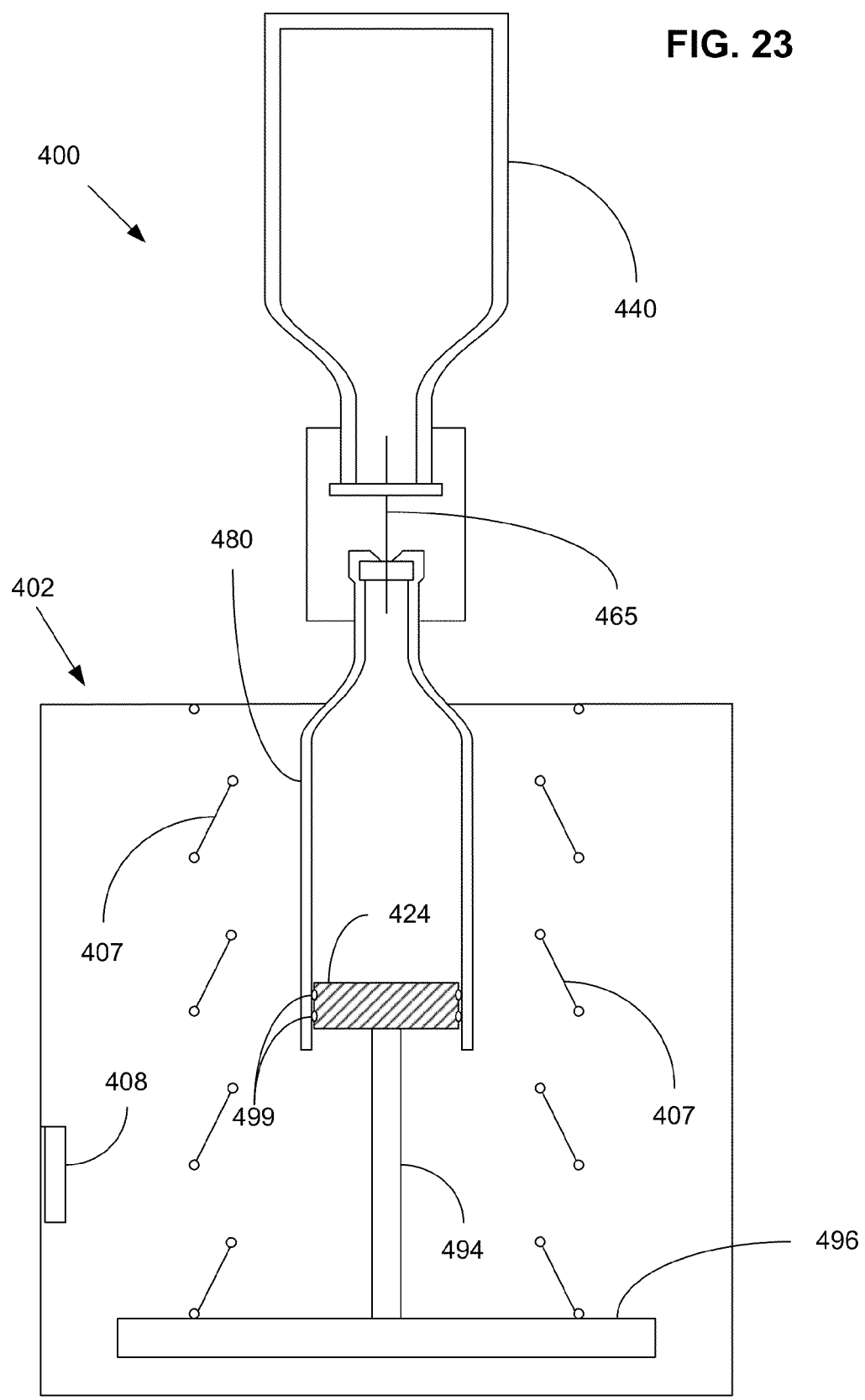
FIG. 23 illustrates a cross-sectional view of a system for transferring fluidic media in accordance with an embodiment of the present invention.

FIGS. 22-23 illustrate a cross-sectional view of a system 400 in accordance with an embodiment of the present invention. The system 400 may include, but is not limited to, a vial 440, a reservoir 480, a plunger head 490, a plunger arm 494, a transfer guard 460, and a housing portion 402. The vial 440 may include a septum 444. The vial 440 may be for containing fluidic media. The reservoir 480 may have an interior volume for containing fluidic media. The plunger head 490 may be located within the reservoir 480 and may be moveable within the reservoir 480 to expand or contract the interior volume of the reservoir 480. The plunger head 490 may be connected to the plunger arm 494. The reservoir 480 may include a septum 484 located at a port of the reservoir 480. The transfer guard 460 may include a needle 465 for providing a fluid path from an interior volume of the vial 440 to the interior volume of the reservoir 480. The needle 465 of the transfer guard 460 may be able to pierce the septum 444 of the vial 440 and the septum 484 of the reservoir 480, so as to provide a fluid path from the vial 440 to the reservoir 480 through the needle 465. The plunger head 490 may include at least one seal member 499, such as an o-ring, or the like to facilitate movement within the interior volume of the reservoir 480 and/or to substantially prevent fluidic media from flowing between the plunger head 490 and the reservoir 480.

The system 400 may allow for automating a filling process of the reservoir 480 with fluidic media from the vial 440. The system 400 may include a bias member such as a spring 407 and a handle 496. In various embodiments, the system 400 may further include a latch 408. In various embodiments, the plunger arm 494 and the handle 496 may be configured such that the plunger arm 494 is able to snap together with the handle 496 to connect the plunger arm 494 to the handle 496. In various other embodiments, the plunger arm 494 and the handle 496 may be configured to be connected in other ways, such as by screwing the plunger arm 494 into the handle 496. In some embodiments, the handle 486 may be part of the plunger arm 494, and the handle 496 may be connectable to the spring 407.

The spring 407 may be connected between a top surface of the housing portion 402 and the handle 496. The spring 407 may be initially biased toward an expanded position, but may be held compressed by the handle 496, which may be held in place by the latch 408. The system 400 may allow for the reservoir 480 to be snapped or otherwise connected in place within the housing portion 402. The system 400 may allow for filling the reservoir 480 using a force applied by the spring 407 on the handle 496 when the latch 408 is released to allow the spring 407 to push down on the handle 496. According to one embodiment of the system 400, the handle 496 may be connected to the plunger arm 494, and the plunger arm 494 may be connected to the plunger head 490. In such an embodiment, movement of the handle 486 away from the reservoir 480 may cause the plunger head 490 to move within the reservoir 480 to create a vacuum that enables a filling of the reservoir 480 by drawing fluid from the vial 440.

In various embodiments, a tension of the spring 407 may be selected so as to allow for the reservoir 480 to fill at different rates when the spring 407 expands depending on the tension of the spring 407. Thus, various embodiments of the present invention allow for spring loaded automatic filling of a reservoir, and for drawing a fluid or drug from an inverted vial into a reservoir. In some embodiments, a lead screw (not shown) may be used in place of the spring 407 to move the plunger arm 494 for an automated filling of the reservoir 480.

Figure 24:
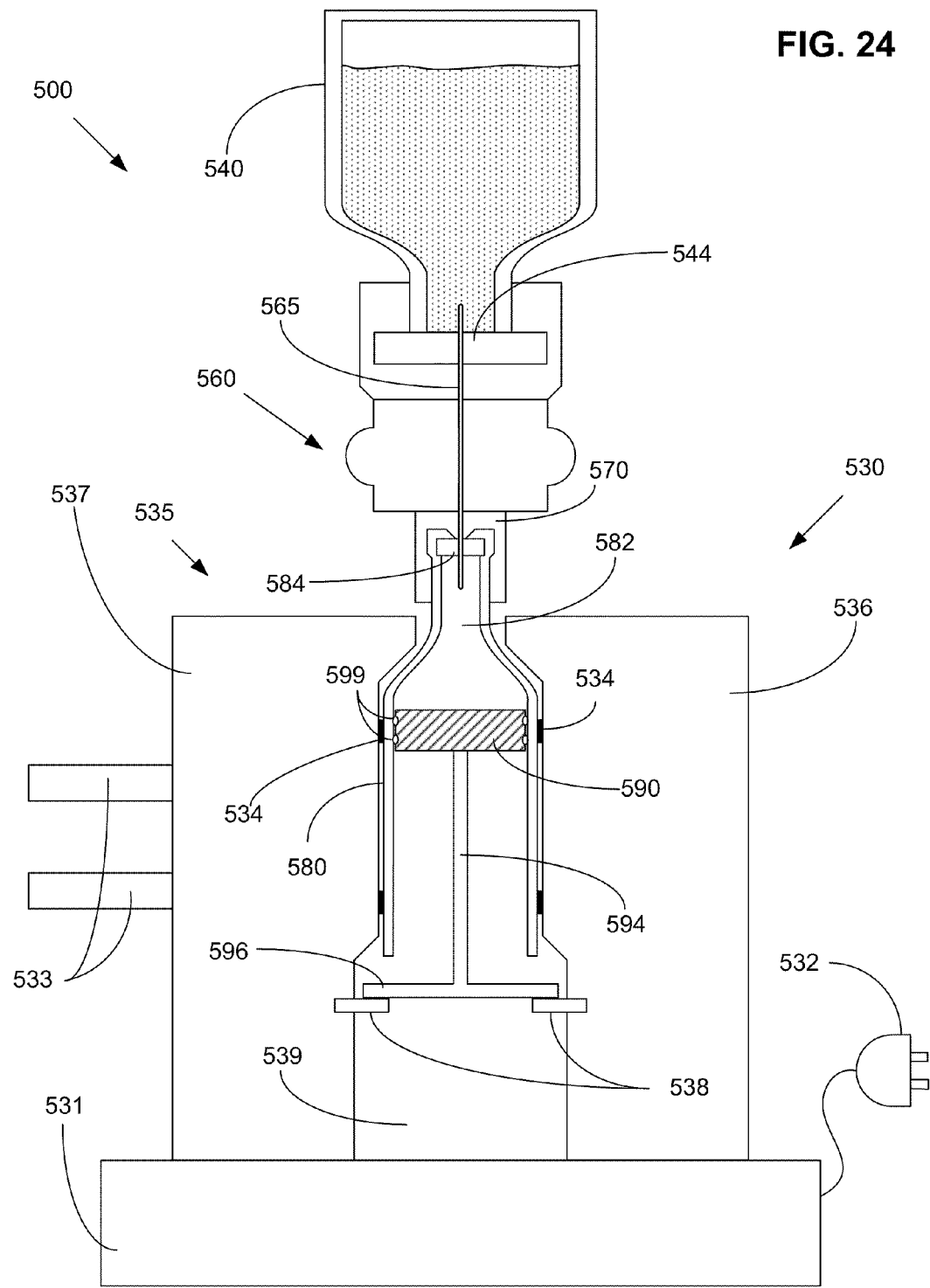
FIG. 24 illustrates a cross-sectional view of a system for transferring fluidic media in accordance with an embodiment of the present invention.
Figure 25:
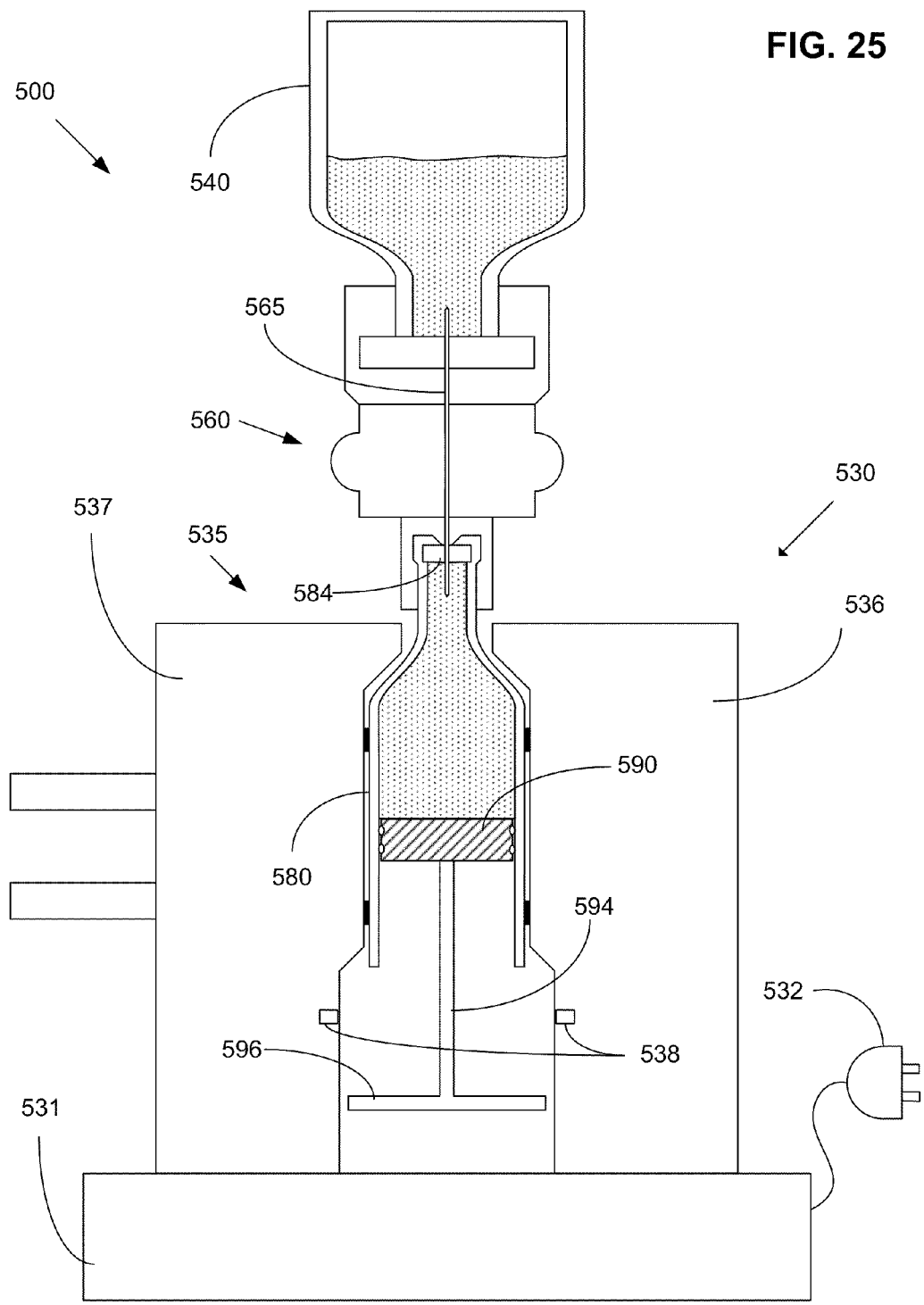
FIG. 25 illustrates a cross-sectional view of a system for transferring fluidic media in accordance with an embodiment of the present invention.

FIGS. 24-25 illustrate a cross-sectional view of a system 500 in accordance with an embodiment of the present invention. The system 500 may include, but is not limited to, a reservoir 580, a plunger head 590, a plunger arm 594, a transfer guard 560, a vial 540, and a vibrating apparatus 530. The vial 540 may be for containing fluidic media. The transfer guard 560 may include a needle 565 for transferring fluidic media between the vial 540 and the reservoir 580. The vial 540 may include a septum 544 pierceable by the needle 565. The reservoir 580 may include a septum 584 pierceable by the needle 565. The system 500 may include a handle 596 connected to the plunger arm 594. The vibrating apparatus 530 may include a holding unit 535 and a vibrator 531.

In various embodiments, the vibrating apparatus 530 may further include a power source 532. The power source 532 may comprise, for example, an electrical plug for plugging the vibrator 531 into an electrical socket, a battery for powering the vibrator 531, or the like. In various embodiments, the vibrator 531 is an electric vibrator, or the like.

The holding unit 535 may allow for holding the reservoir 580. In various embodiments, the holding unit 535 may include a first holder 536 and a second holder 537 for holding the reservoir 580. The holding unit 535 may be configured such that the plunger arm 594 that is connected to the plunger head 590 located within the reservoir 580 is moveable in a case where the holding unit 535 is holding the reservoir 580 and the reservoir 580 is being filled with fluidic media.

The vibrator 531 may allow for vibrating the holding unit 535 such that the reservoir 580 is vibrated. In various embodiments, the vibrator 531 may be configured to vibrate the holding unit 535 in a case where the holding unit 535 is holding the reservoir 580 and the reservoir 580 is being filled with fluidic media, so as to vibrate the reservoir 580 and degas or otherwise cause air bubbles contained in fluidic media in the reservoir 580 to travel upwards within the reservoir 580. Additionally, in various embodiments, the vibrator 531 may be configured to shake the holding unit 535 sufficiently in a case where the holding unit 535 is holding the reservoir 580 and the reservoir 580 is being filled with fluidic media such that air bubbles are shaken free from fluidic media contained in the reservoir 580.

In various embodiments, the holding unit 535 may include the first holder 536 and the second holder 537. The plunger arm 594 may be moveable within a space 539 between the first holder 536 and the second holder 537 in a case where the reservoir 580 is being held by the first holder 536 and the second holder 537 and the reservoir 580 is being filled with fluidic media. In various embodiments, the first holder 536 and the second holder 537 may be connected to the vibrator 531. In addition, in various embodiments, the space 539 may be at least partially between the plunger arm 594 and the vibrator 531.

In some embodiments, one or both of the first holder 536 and the second holder 537 may be attached to the vibrator 531 with hinges or doors (not shown) or the like. The doors (not shown) may be configured to swing open to allow for placing the reservoir 580 at least partially between the first holder 536 and the second holder 537. The doors (not shown) may be further configured to swing closed and lock so that the reservoir 580 is held tightly between the first holder 536 and the second holder 537. Additionally, in some embodiments, the holding unit 535 may further include cushions 534 between the first holder 536 and the reservoir 580, and between the second holder 537 and the reservoir 580. In various embodiments, the holding unit 535 may be a single member into which the reservoir 580 is inserted and held securely.

In various embodiments, the holding unit 535 may be configured such that, in a case where the holding unit 535 is holding the reservoir 580, fluidic media is able to be drawn into the reservoir 580 through a port 582 of the reservoir 580 that is located to an opposite side of the plunger head 590 from the plunger arm 594. Additionally, in various embodiments, the holding unit 535 may be configured such that the plunger arm 594 is moveable in a direction toward the vibrator 531 in a case where the holding unit 535 is holding the reservoir 580 and the reservoir 580 is being filled with fluidic media.

In various embodiments, the vibrating apparatus 530 may include one or more supports 533 for supporting the holding unit 535. The one or more supports 533 may be attached to a stand (not shown), or the like.

In various embodiments, the system 500 may include the transfer guard 560. The transfer guard 560 may allow for transferring fluidic media from the vial 540 to the reservoir 580 in a case where the holding unit 535 is holding the reservoir 580. In some embodiments, the transfer guard 560 may include an end 570 for supporting the reservoir 580. The port 582 of the reservoir 580 may be insertable into the end 570 of the transfer guard 560. The septum 584 of the reservoir 580 may be pierced by the needle 565 of the transfer guard 560 when the reservoir 580 is inserted into the end 570 of the transfer guard 560.

In some embodiments, the vibrating apparatus 530 may include one or more latches 538. The one or more latches 538 may allow for preventing the plunger arm 594 from being moved when the holding unit 535 is holding the reservoir 580 prior to a time when the reservoir 580 is being filled with fluidic media. As a result, the plunger head 590 that is connected to the plunger arm 594 is not moveable within the reservoir 580 when the holding unit 535 is holding the reservoir 580 prior to the time when the reservoir 580 is being filled with fluidic media. In various embodiments, the one or more latches 538 may clasp or otherwise hold onto one or both of the plunger arm 594 and the handle 596. In such embodiments, the one or more latches 538 may be operable to swing open, retract, or otherwise release one or both of the plunger arm 594 and the handle 596 to allow the plunger arm 594 to move within the space 539, such that the plunger head 590 can be moved within the reservoir 580. Thus, the reservoir 580 may be filled with fluidic media drawn from the vial 540.

The holding unit 535 may be configured such that the handle 596 connected to the plunger arm 594 is moveable within the space 539 between the reservoir 538 and the vibrator 531 in a case where the holding unit 535 is holding the reservoir 580 and the reservoir 580 is being filled with fluidic media. In some embodiments, the handle 596 may be disconnectable from the plunger arm 594, such that the handle 596 may be disconnected from the plunger arm 594 after the reservoir 580 has been sufficiently filled with fluidic media.

In some embodiments, the handle 596 may be able to be pulled by a user while the vibrator 531 is vibrating the reservoir 580. In various other embodiments, the handle 596 may be connected to a bias member (not shown), such as a spring to move the handle 596 so as to move the plunger head 590 when the one or more latches 538 are opened to release one or both of the plunger arm 594 and the handle 596. In some embodiments, the system may further include a motor (not shown) for moving one or both of the plunger arm 594 and the handle 596 such that the plunger head 590 is moveable within the reservoir 580 while the holding unit 535 is holding the reservoir 580.

According to an embodiment exemplified in FIGS. 24 and 25, during a filling process, the needle 565 of the transfer guard 560 may establish a fluid path between the vial 540 and the reservoir 580. The one or more latches 580 may be released from the handle 596 to allow the plunger head 590 to move to allow fluidic media to flow from the vial 540 into the reservoir 580. While the reservoir 580 is filling with fluidic media, the vibrator 531 may vibrate the reservoir 580 such that air bubbles in fluidic medium contained in the reservoir 580 travel upwards toward the port 582 of the reservoir 580. Thus, in various embodiments, the vibrator 531 may allow for shaking the reservoir 580 to degas fluidic media being filled into the reservoir 580. In various embodiments, once the filling process has completed in the system 500, the vial 540 may be disconnected from the transfer guard 560. Air in the reservoir 580 may be subsequently pushed out of the reservoir 580, for example, by pressing on the handle 596.

Figure 26:
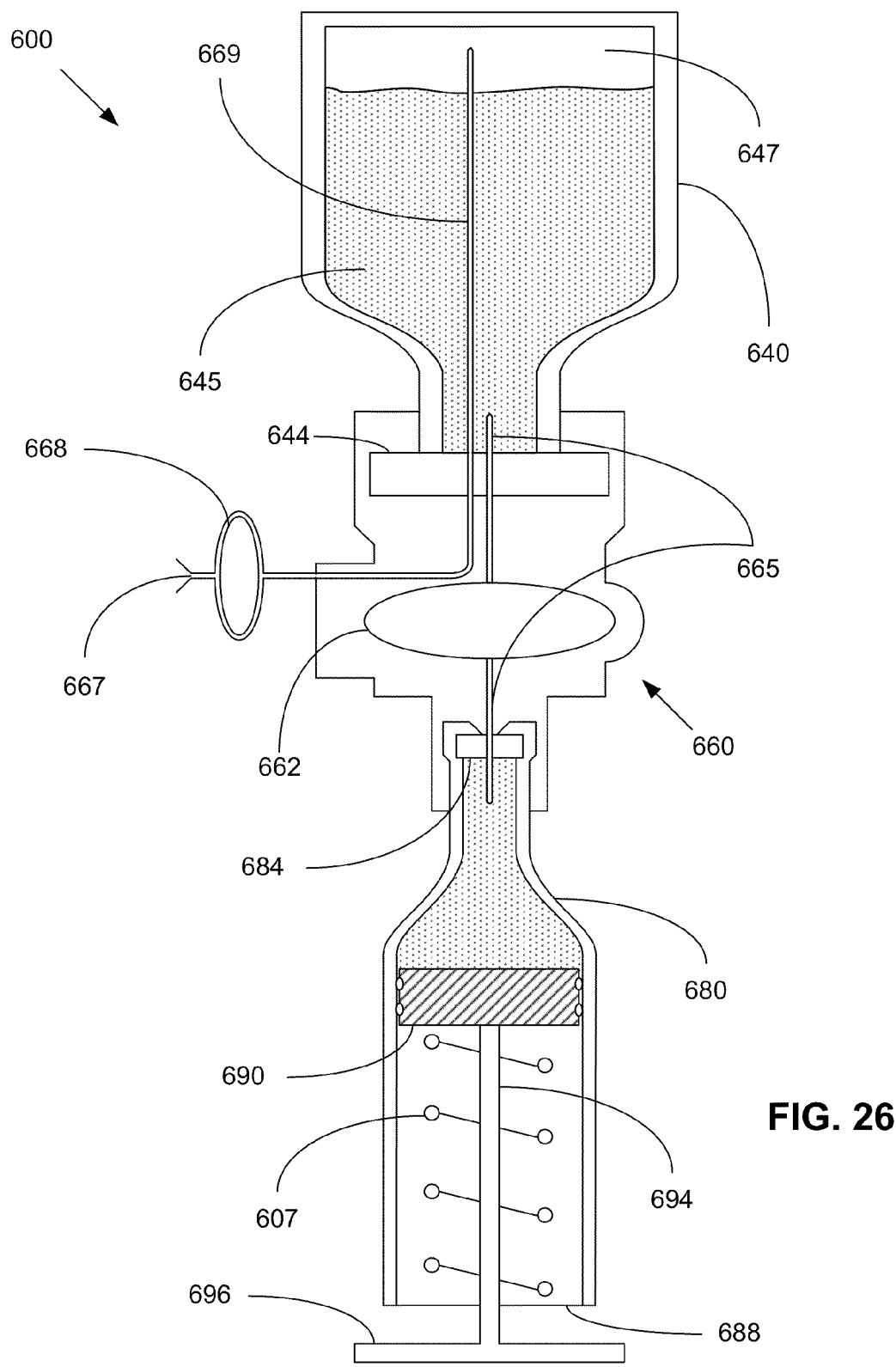
FIG. 26 illustrates a cross-sectional view of a system for transferring fluidic media in accordance with an embodiment of the present invention.
Figure 27:
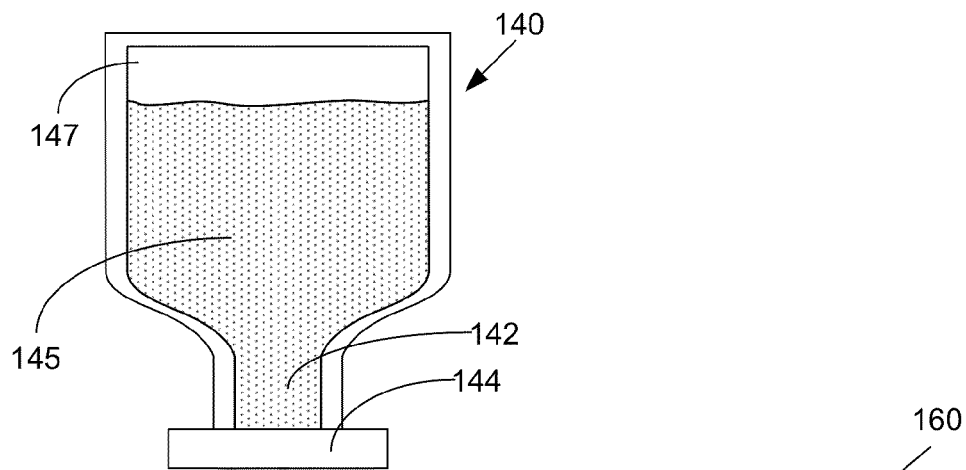
FIG. 27 illustrates a cross-sectional view of a vial for use with a system for transferring fluidic media in accordance with an embodiment of the present invention.

FIG. 26 illustrates a cross-sectional view of a system 600 in accordance with an embodiment of the present invention. The system 600 may include, but is not limited to, a reservoir 680, a plunger head 690, a plunger arm 694, a handle 696, a bias member 607, a first needle 665, a second needle 669, a membrane 668, an air inlet 667, a vial 640, a transfer guard 660, and a filter 662. The reservoir 680 may have a septum 684. The vial 640 may have a septum 644. The system 600 may be configured such that in a case where the vial 640 is inverted and the second needle 669 is inserted into the vial 640, the second needle 669 vents to atmosphere from the air inlet 667 to a headspace 647 in the vial 640 above an area 645 of the vial 640 that contains fluidic media. Thus, by using the second needle 669 to vent the headspace 647 of the vial 640 to atmosphere, there may be substantially no percolation of air through fluidic media in the vial 640.

In various embodiments, the system 600 may be configured such that in a case where the vial 640 is inverted and the second needle 669 is inserted into the vial 640, the second needle 669 vents to atmosphere from the air inlet 667 to the area 645 of the vial 350 that contains fluidic media. Thus, the second needle 669 in the vial 640 may provide for atmospheric pressure in the vial 640.

The membrane 668 may be a hydrophobic membrane. The hydrophobic membrane 668 may substantially reduce an addition of water vapor through the second needle 669 to the vial 640. The system 600 may be configured such that as fluidic media is drawn into the reservoir 680, it passes through the filter 662, which may comprise a membrane, such as a hydrophobic membrane or a hydrophilic membrane, to filter out air bubbles and/or degas the fluidic media drawn into the reservoir 680. Additionally, water vapor may be restricted from entering the vial 640 through the second needle 669 by the hydrophobic membrane 668. In various embodiments, equalizing a pressure of the vial 640 with an atmospheric pressure may help to prime the vial 640. In other embodiments, the membrane 668 may be a hydrophilic membrane.

In various embodiments, the plunger arm 694 and the handle 696 may be configured such that the plunger arm 694 is able to snap together or otherwise connect with the handle 696 to connect the plunger arm 694 to the handle 696. In various other embodiments, the plunger arm 694 and the handle 696 may be configured to be connected in other ways, such as by screwing the plunger arm 694 into the handle 696. In some embodiments, the handle 696 may be part of the plunger arm 694, and the handle 696 may be connectable to the bias member 607. According to some embodiments of the system 600, the handle 696 may be connected to the plunger arm 694, and the plunger arm 694 may be connected to the plunger head 690. In such an embodiment, movement of the handle 696 away from the reservoir 680 may cause the plunger head 690 to retract within the reservoir 680 to create a vacuum that enables a filling of the reservoir 680 by drawing fluidic media from the vial 640.

In some embodiments, the bias member 607 may be a spring, or the like. The bias member 607 may be located between the plunger head 690 and an end 688 of the reservoir 680. The bias member 607 may be initially in an expanded position. The bias member 607 may provide a retaining force behind the plunger head 690 in the reservoir 680 as the plunger head 690 is moved within the reservoir 680. Movement of the handle 696 away from the reservoir 680 may move the plunger head 690 within the reservoir 680 and compress the bias member 607 to a compressed position.

In various embodiments, a tension of the bias member 607 may be selected so as to allow for the reservoir 680 to fill at different rates when the bias member 607 compresses depending on the tension of the bias member 607. Thus, the system 600 may allow for a vial pressure equalizer using the second needle 669, with a bias member 607 to assist movement of the plunger head 690, and a filter 662 to filter air bubbles out of fluidic media as the fluidic media is filled into the reservoir 680.

In various embodiments, the fill volume control 230 (FIGS. 11-14 and 16) may be used with embodiments of the systems described above, and/or may be provided at various locations of those embodiments. For example, with reference to FIGS. 17-21, a fill volume control, such as the fill volume control 230 (FIGS. 11-14 and 16) described above, may be provided in an area 321 of the system 300 such that the fill volume control is positioned between the first housing portion 302 and the second housing portion 322. In such an example, the fill volume control may allow for the system 300 to transfer fixed volumes of fluidic media during a filling process as previously described.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system for transferring fluidic media, the system comprising:
   a first housing portion having an elongated dimension; and
   a second housing portion operatively connected to the first housing portion, the second housing portion for moving relative to the elongated dimension of the first housing portion;
   one of the first and second housing portions removably connectable to a transfer guard, the one of the first and second housing portions having an interior volume configured to receive a reservoir, the transfer guard providing a fluid path from a vial to the reservoir when the transfer guard is connected to the one of the first and second housing portions and the reservoir is received in the interior volume of the one of the first and second housing portions;
   the other of the first and second housing portions operatively engageable to a plunger head positioned in the reservoir;
   the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion.

2. The system of claim 1, wherein the other of the first and second housing portions has a connecting portion configured to operatively connect to the plunger head.

3. The system of claim 1, wherein the one of the first and second housing portions has a connecting portion configured to engage with and connect to the transfer guard.

4. The system of claim 3, wherein the connecting portion comprises at least one projection configured to be received within an aperture in the transfer guard.

5. The system of claim 3, wherein the connecting portion is arranged within the interior volume of the one of the first and second housing portions.

6. The system of claim 1, wherein the first and second housing portions are configured such that, when the reservoir is received in the one of the first and second housing portions and the other of the first and second housing portions is operatively engaged to the plunger head, movement of the second housing portion along the elongated dimension of the first housing portion causes the plunger head to move within the reservoir to transfer fluidic media between the reservoir and the vial.

7. A method for transferring fluidic media, the method comprising:
   providing a first housing portion having an elongated dimension; and
   locating a second housing portion operatively connected to the first housing portion, the second housing portion for moving relative to the elongated dimension of the first housing portion;
   configuring one of the first and second housing portions to be removably connectable to a transfer guard, the transfer guard for providing a fluid path from a vial to a reservoir;
   configuring the other of the first and second housing portions to be operatively engageable to a plunger head positioned in the reservoir; and
   configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the elongated dimension of the first housing portion.

8. The method of claim 7, further comprising providing the one of the first and second housing portions with a connecting portion configured to engage with and connect to the transfer guard.

9. The method of claim 8, wherein the connecting portion comprises at least one projection configured to be received within an aperture in the transfer guard.

10. The method of claim 8, further comprising arranging the connecting portion within the interior volume of the one of the first and second housing portions.

11. The system of claim 7, wherein configuring the first and second housing portions comprises configuring the first and second housing portions such that, when the reservoir is received in the one of the first and second housing portions and the other of the first and second housing portions is operatively engaged to the plunger head, movement of the second housing portion along the elongated dimension of the first housing portion causes the plunger head to move within the reservoir to transfer fluidic media between the reservoir and the vial.

12. A system for transferring fluidic media, the system comprising:
   a first housing portion having an elongated dimension;
   a second housing portion operatively connected to the first housing portion, the second housing portion for moving relative to the elongated dimension of the first housing portion;
   one of the first and second housing portions removably connectable to a transfer guard, the one of the first and second housing portions having an interior volume configured to receive the reservoir, the transfer guard providing a fluid path from a vial to the reservoir when the transfer guard is connected to the one of the first and second housing portions and the reservoir is received in the interior volume of the one of the first and second housing portions;
   the other of the first and second housing portions operatively engageable to a plunger head positioned in the reservoir;
   the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion; and
   a threaded member supported by the other of the first and second housing portions, the threaded member configured to engage a threaded portion of the plunger when the reservoir is received in the one of the first and second housing portions.

13. A system for transferring fluidic media, the system comprising:
   a first housing portion having an elongated dimension;
   a second housing portion operatively connected to the first housing portion, the second housing portion for moving relative to the elongated dimension of the first housing portion;
   one of the first and second housing portions removably connectable to a transfer guard, the one of the first and second housing portions having an interior volume configured to receive the reservoir, the transfer guard providing a fluid path from a vial to the reservoir when the transfer guard is connected to the one of the first and second housing portions and the reservoir is received in the interior volume of the one of the first and second housing portions;
   the other of the first and second housing portions operatively engageable to a plunger head positioned in the reservoir;
   the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion; and
   the other of the first and second housing portions extending at least partially within the one of the first and second housing portions.

14. A system for transferring fluidic media, the system comprising:
   a first housing portion having an elongated dimension;
   a second housing portion operatively connected to the first housing portion, the second housing portion for moving relative to the elongated dimension of the first housing portion;
   one of the first and second housing portions removably connectable to a transfer guard, the one of the first and second housing portions having an interior volume configured to receive the reservoir, the transfer guard providing a fluid path from a vial to the reservoir when the transfer guard is connected to the one of the first and second housing portions and the reservoir is received in the interior volume of the one of the first and second housing portions;
   the other of the first and second housing portions operatively engageable to a plunger head positioned in the reservoir;
   the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion; and
   the other of the first and second housing portions extending at least partially within the one of the first and second housing portions and is arranged for sliding motion within the one of the first and second housing portions.

15. A system for transferring fluidic media, the system comprising:
   a first housing portion having an elongated dimension;
   a second housing portion operatively connected to the first housing portion, the second housing portion for moving relative to the elongated dimension of the first housing portion;
   one of the first and second housing portions removably connectable to a transfer guard, the one of the first and second housing portions having an interior volume configured to receive the reservoir, the transfer guard providing a fluid path from a vial to the reservoir when the transfer guard is connected to the one of the first and second housing portions and the reservoir is received in the interior volume of the one of the first and second housing portions;
   the other of the first and second housing portions operatively engageable to a plunger head positioned in the reservoir;

the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion;

the other of the first and second housing portions has a connecting portion configured to operatively connect to the plunger head; and the connecting portion has a receptacle for receiving a handle of a plunger arm that extends from the plunger head.

16. A system for transferring fluidic media, the system comprising:

a first housing portion having an elongated dimension;

a second housing portion operatively connected to the first housing portion, the second housing portion for moving relative to the elongated dimension of the first housing portion;

one of the first and second housing portions removably connectable to a transfer guard, the one of the first and second housing portions having an interior volume configured to receive the reservoir, the transfer guard providing a fluid path from a vial to the reservoir when the transfer guard is connected to the one of the first and second housing portions and the reservoir is received in the interior volume of the one of the first and second housing portions;

the other of the first and second housing portions operatively engageable to a plunger head positioned in the reservoir;

the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion;

the one of the first and second housing portions has a connecting portion configured to engage with and connect to the transfer guard;

the connecting portion is arranged within the interior volume of the one of the first and second housing portions; and the one of the first and second housing portions has a side surface with an opening into the interior volume, the one of the one of the first and second housing portions further has a door arranged to selectively open and close the opening, wherein the interior volume of the one of the first and second housing portions is exposed to allow a user to insert the reservoir into the interior volume and to connect the transfer guard to the connecting portion within the interior volume, when the door is arranged to open the opening.

17. A system for transferring fluidic media, the system comprising:

a first housing portion having an elongated dimension;

a second housing portion operatively connected to the first housing portion, the second housing portion for moving relative to the elongated dimension of the first housing portion;

one of the first and second housing portions removably connectable to a transfer guard, the one of the first and second housing portions having an interior volume configured to receive the reservoir, the transfer guard providing a fluid path from a vial to the reservoir when the transfer guard is connected to the one of the first and second housing portions and the reservoir is received in the interior volume of the one of the first and second housing portions;

the other of the first and second housing portions operatively engageable to a plunger head positioned in the reservoir;

the first and second housing portions configured such that fluidic media is transferred from the vial to the reservoir in a case where the reservoir is received in the one of the first and second housing portions, the other of the first and second housing portions is operatively engaged to the plunger head, and the second housing portion is moved relative to the elongated dimension of the first housing portion; and the one of the first and second housing portions has a side surface with an opening into the interior volume, the one of the one of the first and second housing portions further has a door arranged to selectively open and close the opening, wherein the interior volume of the one of the first and second housing portions is exposed to allow a user to insert the reservoir into the interior volume when the door is arranged to open the opening.

18. A method for transferring fluidic media, the method comprising:

providing a first housing portion having an elongated dimension; and locating a second housing portion operatively connected to the first housing portion, the second housing portion for moving relative to the elongated dimension of the first housing portion;

configuring one of the first and second housing portions to be removably connectable to a transfer guard, the transfer guard for providing a fluid path from a vial to a reservoir;

configuring the other of the first and second housing portions to be operatively engageable to a plunger head positioned in the reservoir; and configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the elongated dimension of the first housing portion; and supporting a threaded member by the other of the first and second housing portions, the threaded member configured to engage a threaded portion of the plunger when the reservoir is received in the one of the first and second housing portions.

19. A method for transferring fluidic media, the method comprising:

providing a first housing portion having an elongated dimension; and locating a second housing portion operatively connected to the first housing portion, the second housing portion for moving relative to the elongated dimension of the first housing portion;

configuring one of the first and second housing portions to be removably connectable to a transfer guard, the transfer guard for providing a fluid path from a vial to a reservoir;

configuring the other of the first and second housing portions to be operatively engageable to a plunger head positioned in the reservoir; and configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the elongated dimension of the first housing portion; and locating the second housing portion further comprises arranging the first and second housing portions such that the other of the first and second housing portions extends at least partially within the one of the first and second housing portions.

20. A method for transferring fluidic media, the method comprising:

providing a first housing portion having an elongated dimension; and locating a second housing portion operatively connected to the first housing portion, the second housing portion for moving relative to the elongated dimension of the first housing portion;

configuring one of the first and second housing portions to be removably connectable to a transfer guard, the transfer guard for providing a fluid path from a vial to a reservoir;

configuring the other of the first and second housing portions to be operatively engageable to a plunger head positioned in the reservoir; and configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the elongated dimension of the first housing portion; and locating the second housing portion further comprises arranging the first and second housing portions such that the other of the first and second housing portions extends at least partially within the one of the first and second housing portions and is arranged for sliding motion within the one of the first and second housing portions.

21. A method for transferring fluidic media, the method comprising;

providing a first housing portion having an elongated dimension; and locating a second housing portion operatively connected to the first housing portion, the second housing portion for moving relative to the elongated dimension of the first housing portion;

configuring one of the first and second housing portions to be removably connectable to a transfer guard, the transfer guard for providing a fluid path from a vial to a reservoir;

configuring the other of the first and second housing portions to be operatively engageable to a plunger head positioned in the reservoir; and configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the elongated dimension of the first housing portion;

providing the one of the first and second housing portions with a connecting portion configured to engage with and connect to the transfer guard;

arranging the connecting portion within the interior volume of the one of the first and second housing portions; and providing the one of the first and second housing portions with a side surface having an opening into the interior volume, and arranging a door to selectively open and close the opening, wherein the interior volume of the one of the first and second housing portions is exposed to allow a user to insert the reservoir into the interior volume and to connect the transfer guard to the connecting portion within the interior volume, when the door is open.

22. A method for transferring fluidic media, the method comprising:

providing a first housing portion having an elongated dimension; and locating a second housing portion operatively connected to the first housing portion, the second housing portion for moving relative to the elongated dimension of the first housing portion;

configuring one of the first and second housing portions to be removably connectable to a transfer guard, the transfer guard for providing a fluid path from a vial to a reservoir;

configuring the other of the first and second housing portions to be operatively engageable to a plunger head positioned in the reservoir; and configuring the first and second housing portions such that fluidic media is transferred from the vial to the reservoir in a case where the one of the first and second housing portions is connected to the transfer guard, and the other of the first and second housing portions is operatively engaged to the plunger head, and the second housing portion is moved relative to the elongated dimension of the first housing portion; and providing the one of the first and second housing portions with a side surface having an opening into the interior volume, arranging a door to selectively open and close the opening, wherein the interior volume of the one of the first and second housing portions is exposed to allow a user to insert the reservoir into the interior volume when the door is arranged to open the opening.

* * * * *